US009309325B2

(12) United States Patent
Craik et al.

(10) Patent No.: US 9,309,325 B2
(45) Date of Patent: Apr. 12, 2016

(54) ANTIBODIES AND METHODS OF USE THEREOF

(75) Inventors: Charles S. Craik, San Francisco, CA (US); Eric L. Schneider, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1126 days.

(21) Appl. No.: 13/319,036

(22) PCT Filed: May 4, 2010

(86) PCT No.: PCT/US2010/033624
§ 371 (c)(1),
(2), (4) Date: Jan. 3, 2012

(87) PCT Pub. No.: WO2010/129609
PCT Pub. Date: Nov. 11, 2010

(65) Prior Publication Data
US 2012/0141373 A1 Jun. 7, 2012

Related U.S. Application Data

(60) Provisional application No. 61/176,461, filed on May 7, 2009.

(51) Int. Cl.
C07K 16/40 (2006.01)
A61K 51/10 (2006.01)
C12Q 1/37 (2006.01)
G01N 33/574 (2006.01)
A61K 38/00 (2006.01)
A61K 39/00 (2006.01)

(52) U.S. Cl.
CPC ............. *C07K 16/40* (2013.01); *A61K 51/1075* (2013.01); *C12Q 1/37* (2013.01); *G01N 33/574* (2013.01); *A61K 38/00* (2013.01); *A61K 2039/505* (2013.01); *C07K 2317/21* (2013.01); *C07K 2317/55* (2013.01); *C07K 2317/56* (2013.01); *C07K 2317/565* (2013.01); *C07K 2317/76* (2013.01); *G01N 2333/95* (2013.01); *G01N 2500/04* (2013.01)

(58) Field of Classification Search
None
See application file for complete search history.

(56) References Cited

U.S. PATENT DOCUMENTS

| 7,329,737 | B2 | 2/2008 | Sexton et al. | |
| 2003/0027981 | A1 | 2/2003 | Dano et al. | |
| 2003/0050251 | A1 | 3/2003 | Semple et al. | |
| 2003/0092752 | A1 | 5/2003 | Lin et al. | |
| 2003/0166514 | A1 | 9/2003 | Jones et al. | |
| 2004/0186060 | A1* | 9/2004 | Duncan et al. | 514/19 |
| 2006/0024300 | A1 | 2/2006 | Adams et al. | |
| 2006/0171884 | A1 | 8/2006 | Foltz et al. | |
| 2006/0246071 | A1 | 11/2006 | Green et al. | |
| 2008/0025913 | A1 | 1/2008 | Bowdish et al. | |
| 2008/0051559 | A1 | 2/2008 | Craik et al. | |
| 2008/0226630 | A1 | 9/2008 | Lantto et al. | |
| 2009/0181017 | A1 | 7/2009 | Hass et al. | |
| 2010/0260762 | A1 | 10/2010 | Moe et al. | |

FOREIGN PATENT DOCUMENTS

| WO | 01/29056 | 4/2001 |
| WO | 2004/003183 | 1/2004 |
| WO | 2006/050177 | 5/2006 |
| WO | 2007075921 | 5/2007 |

OTHER PUBLICATIONS

Farady et al. (J. Mol. Biol., 369: 1041-1051, 2007).*
Bylund et al. (Am. J. Physiol. 265: L421-L429, 1993).*
Mariuzza et al. (Annu. Rev. Biophys. Biophys. Chem. 1987; 16: 139-159).*
Bhatt et al. "Quantitation of membrane type serine protease 1 (MT-SP1) in transformed and normal cells" Biol Chem 2003, 384(2):257-266.
Collaborative Computational Project, No. 4 "The CCP4 suite: programs for protein crystallography" Acta Crystallogr D Biol Crystallogr 1994, 50(Pt. 5):760-763.
De Haard et al. "A large non-immunized human Fab fragment phage library that permits rapid isolation and kinetic analysis of high affinity antibodies" J Biol Chem 1999, 274(26):18218-18230.
Evrard GX et al. "Assessment of automatic ligand building in ARP/wARP" Acta Crystallogr D Biol Crystallogr 2007, 63(Pt. 1):108-117.
Farady et al. "Structure of an Fab-protease complex reveals a highly specific non-canonical mechanism of inhibition" J Mol Biol 2008, 380(2):351-360.
Farady et al. "The mechanism of inhibition of antibody-based inhibitors of membrane-type serine protease 1 (MT-SP1)" J Mol Biol 2007, 369(4):1041-1051.
Foltz et al. American Society of Hematology Annual Meeting Abstracts 2005, 106: Abstract 4816.
Krissinel & Henrick "Inference of macromolecular assemblies from crystalline state" J Mol Biol 2007, 372(3):774-97.
Krowarsch et al. "Interscaffolding additivity: binding of P1 variants of bovine pancreatic trypsin inhibitor to four serine proteases" J Mol Biol 1999, 289(1):175-86.

(Continued)

*Primary Examiner* — Brad Duffy
*Assistant Examiner* — Nelson B Moseley, II
(74) *Attorney, Agent, or Firm* — Carol L. Francis; Brian E. Davy; Bozicevic, Field & Francis LLP

(57) ABSTRACT

The disclosure relates to protease-binding agent specific for a protease. The agent may be an antibody capable of specifically binding and inhibiting a protease, such as a P1-Arg-specific protease. The disclosure also provides methods of producing, and compositions comprising the subject agent. Methods and kits related to the protease-binding agent find use in protection against, detection, diagnosing, treating cancer and infections due to pathogens containing active proteases.

16 Claims, 17 Drawing Sheets

(56) References Cited

OTHER PUBLICATIONS

Lovell et al. "Structure validation by Cα geometry: φ, ψ and Cβ deviation" Proteins 2003, 50(3):437-450.

McGrath et al. "The sequence and reactive site of ecotin. A general inhibitor of pancreatic serine proteases from *Escherichia coli*" J Biol Chem 1991, 266(10):6620-6625.

Murshudov et al. "Efficient anisotropic refinement of macromolecular structures using FFT" Acta Crystallogr D Biol Crystallogr 1999, 55(Pt. 1):247-255.

Ozawa et al. "The reactive site of trypsin inhibitors" J Biol Chem 1966, 241(17):3955-3961.

Perona et al. "Evolutionary divergence of substrate specificity within the chymotrypsin-like serine protease fold" J Biol Chem 1997, 272(48):29987-29990.

Read "Pushing the boundaries of molecular replacement with maximum likelihood" Acta Crystallogr D Biol Crystallogr 2001, 57(Pt. 10):1373-1382.

Sun et al. "Potent and selective inhibition of membrane-type serine protease 1 by human single-chain antibodies" Biochemistry 2003, 42(4):892-900.

Takeuchi et al. "Reverse biochemistry: use of macromolecular protease inhibitors to dissect complex biological processes and identify a membrane-type serine protease in epithelial cancer and normal tissue" Proc Natl Acad Sci USA 1999, 96(20):11054-11061.

Uhland "Matriptase and its putative role in cancer" Cell. Mol. Life Sci. 2006, 63(24):2968-2978.

Wu et al. "Length distribution of CDRH3 in antibodies" Proteins 1993, 16(1):1-7.

Zemlin et al. "Expressed murine and human CDR-H3 intervals of equal length exhibit distinct repertoires that differ in their amino acid composition and predicted range of structures" J Mol Biol 2003, 334(4):733-749.

Copeland, et al. Uniprot ID A3DAI5, Mar. 20, 2007, http://www.uniprot.org/uniprot.org/uniprot/A3DAI5.

Abcam—product overview "Anti-uPA antibody [U-16] (ab131433)" URL: http://www.abcam.com/uPA-antibody-U-16-ab131433.html, (2013) 2 pages.

Ahmad et al., "Inactivation of uPA and its receptor uPAR by 3,3'-Diindolylmethane (DIM) leads to the inhibition of Prostate Cancer Cell growth and migration" (2009) J. Cell. Biochem, 107(3):516-27.

Anderson and Piwnica-Worms "AACR/SNMMI State-of-the-Art Molecular Imaging in Cancer Biology and Therapy: Abstracts." (2013) J. Nuclear Medicine, 54(Suppl 1):3A-35.

Blouse et al. "A Novel Mode of Intervention with Serine Protease Activity" (2009) J. Biol Chem, 284(7):4647-4657.

Botkjaer et al. "Targeting the autolysis loop of urokinase-type plasminogen activator with conformation-specific monoclonal antibodies" (2011) J. Biol Chem, 438:39-51.

Dass et al. "Evolving role of uPA/uPAR system in human cancers" (2008) Cancer Treat Rev, 34:122-136.

Declerck et al. "A Monoclonal Antibody Specific for Two-Chain Urokinase-Type Plasminogen Activator. Application to the Study of the Mechanism of Clot Lysis With Single-Chain Urokinase-Type Plasminogen Activator in Plasma" (1990) Blood, 75(9):1794-800.

Duriseti et al. "Antagonistic Anti-urokinase Plasminogen Activator Receptor (uPAR) Antibodies Significantly Inhibit uPAR-mediated Cellular Signaling and Migration," (2010) J. Biol Chem, 285(35):26878-26888.

GenWay Biotech, Inc.—Product overview "UPA [SPM457], Antibody" (2013), 3 pages.

Harvey et al. "Evaluation of Urinary Plasminogen Activator, Its Receptor, Matrix Metalloproteinase-9, and von Willebrand Factor in Pancreatic Cancer" (2003) Clinical Cancer Res, 9:4935-4943.

Katz et al. "Engineering inhibitors highly selective for the S1 sites of Ser190 trypsin-like serine protease drug targets" (2001) Chemistry and Biology, 8:1107-1121.

Ke et al. "Distinguishing the specificities of closely related proteases" (1997) J. Biol Chem, 272:16603-16609.

Knappik et al. (2000) "Fully Synthetic Human Combinatorial Antibody Libraries (HuCAL) Based on Modular Consensus Frameworks and CDRs Randomized with Trinucleotides" J Mol Biol 296(1):57-86.

Kobayashi et al. "Inhibition of in Vitro Ovarian Cancer Cell Invasion by Modulation of Urokinasetype Plasminogen Activator and Cathepsin B" (1992) Cancer Res, 52:3610-3614.

Lebeau et al. "Targeting uPAR with Antagonistic Recombinaht Human Antibodies in Aggressive Breast Cancer," (2013) Cancer Res, 73:2070-2081.

Lee et al. "Activation of Hepatocyte Growth Factor and Urokinase/Plasminogen Activator by Matriptase, an Epithelial Membrane Serine Protease" J. Biol Chem, 2000, 275(47):36720-36725.

Lin et al. "Structural basis for recognition of urokinase-type plasminogen activator by plasminogen activator inhibitor-1" (2011) J. Biol. Chem, 286(9):7027-7032.

List et al. "Matriptase: Potent Proteolysis on the Cell Surface" Mol Med, 2006 12(1-3):1-7.

Liu et al. "The inhibitory effect of HKa in endothelial cell tube formation is mediated by disrupting the uPA-uPAR complex and inhibiting its signaling and internalization." (2008) Am. J. Physiology-Cell Physiology, 295:C257-C267.

Nelson et al. "Epigenetic alterations in human prostate cancers" (2009) Endocrinology, 150:3991-4002.

Ossowski et al. "Inhibition of urokinase-type plasminogen activator by antibodies: the effect on dissemination of a human tumor in the nude mouse." (1991) Cancer Res, 51:274-281.

Pakneshan et al. "Methylation status of uPA promoter as a molecular mechanism regulating prostate cancer invasion and growth in vitro and in vivo" (2003) FASEB J, 17:1081-1088.

Pakneshan et al. "Hypomethylation of urokinase (uPA) promoter in breast and prostate cancer: prognostic and therapeutic implications" (2005) Curr Cancer Drug Targets, 5:471-488.

Petersen et al. "Localization of epitopes for monoclonal antibodies to urokinase-type plasminogen activator Relationship between epitope localization and effects of antibodies on molecular interactions of the enzyme" (2001) Eur. J. Biochem., 268:4430-4439.

Pittman et al. "Neuronal Plasminogen Activators: Cell Surface Binding Sites and Involvement in Neurite Outgrowth" (1989) J. Neuroscience, 9(12):4269-4286.

Schneider et al. "A reverse binding motif that contributes to specific protease inhibition by antibodies" (2012) J. Mol Biol, 415:699-715.

Sgier et al. "Isolation and characterization of an inhibitory human monoclonal antibody specific to the urokinase-type plasminogen activator, uPA" (2010) Protein Eng Des Sel, 23:261-269.

Shukeir et al. "Alteration of the methylation status of tumor-promoting genes decreases prostate cancer cell invasiveness and turmorigenesis in vitro and in vivo" (2006) Cancer Res, 66:9202-9210.

Sperl et al. "(4-Aminomethyl)phenylguanidine derivatives as nonpeptidic highly selective inhibitors of human urokinase" (2000) PNAS, 97(10):511.-5118.

Spraggon et al. "The crystal structure of the catalytic domain of human urokinase-type plasminogen activator" (1995) Structure, 3:681-691.

Stewart et al. "The relevance of a hypoxic tumour microenvironment in prostate cancer" (2010) BJU Int, 105:8-13.

Takeuchi et al. "Cellular Localization of Membrane-type Serine Protease 1 and Identification of Protease-activated Receptor-2 and Single-chain Urokinase-type Plasminogen Activator as Substrates" J. Biol Chem., (2000) 275(34):26333-26342.

Thermo Scientific—Product data sheet "Urokinase Plasminogen Activator Monoclonal Antibody (SPM457)" (Date not available) 1 page.

Ulisse et al. "The urokinase plasminogen activator system: A target for anti-cancer therapy" (2009) Curr. Cancer Drug Targets, 9:32-71.

Ulmert et al. "Imaging Androgen Receptor Signaling with a Radiotracer Targeting Free Prostate-Specific Antigen" (2012) Cancer Discov, 2:320-327.

Usher et al. "Expression of urokinase plasminogen activator, its receptor and type-1 inhibitor in malignant and benign prostate tissue" (2005) Int J Cancer, 113:870-880.

(56) References Cited

OTHER PUBLICATIONS

Yamamoto et al. "Expression and Localization of Urokinase-Type Plasminogen Activator in Human Astrocytomas in Vivo" (1994) Cancer Res, 54:3556-3661.

Zeslawska et al. "Crystals of the Urokinase Type Plasminogen Activator Variant bc-uPA in Complex with Small Molecule Inhibitors Open the Way towards Structure-based Drug Design" (2000) J. Mol Biol, 301:465-475.

\* cited by examiner

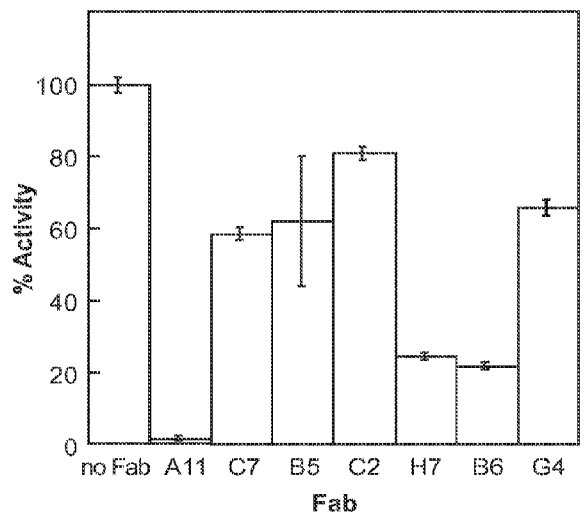

FIG. 1

A11 amino acid sequence
Light Chain
EIVLTQSPGTLSLSPGERATLSCRASQSVSSSYLAWYQQKPGQAPRLLIYGASTRATGIPARFSG
SGSGTDFTLTINSLEPEDFAVYYCQQRSNWPPGYTFGQGTKVEIKRTVAAPSVFIFPPSDEQLKS
GTASVVCLLNNFYPREAKVQWKVDNALQSGNSQESVTEQDSKDSTYSLSSTLTLSKADYEKHKVY
ACEVTHQGLSSPVTKSFNRGEC    (SEQ ID NO: 1)

Heavy Chain
EVQLVQSGGGLVKPGGSLRLSCAASGFTFSSYAMSWVRQAPGKGLEWVSAISGSGGSTYYADSVK
GRFTISRDNSKNTLYLQMSSLRAEDTAVYYCVKDLGIAARRFVSGAFDIWGQGTMVTVSSASTKG
PSVFPLAPSSKSTSGGTAALGCLVKDYFPEPVTVSWNSGALTSGVHTFPAVLQSSGLYSLSSVVT
VPSSSLGTQTYICNVNHKPSNTKVDKKVEPKSCAAA    SEQ ID NO: 3)

E2 amino acid sequence
Light Chain
DIQMTQSPSSLSASVGDRVTITCRASQGISSYLAWYQQKPGKAPKLLIYAASSLQSGVPSRFSGS
GSGTDFTLTISSLQPEDFAVYYCQQHGNLPYTFGDGTKVEIKRTVAAPSVFIFPPSDEQLKSGTA
SVVCLLNNFYPREAKVQWKVDNALQSGNSQESVTEQDSKDSTYSLSSTLTLSKADYEKHKVYACE
VTHQGLSSPVTKSFNRGEC    (SEQ ID NO: 5)

Heavy Chain
MAQVQLVQSGGGLVKPGGSLRLSCAASGFTFSSYAMSWVRQAPGKGLEWVSAISGSGGSTYYADS
VKGRFTISRDNSKNTLYLQMSSLRAEDTAVYYCARPYLTYPQRRGPQNVSPFDNWGQGTMVTVSS
ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCAAA    (SEQ ID NO: 7)

FIG. 2A

A11 nucleic acid sequences
Light Chain
GAAATTGTGTTGACGCAGTCTCCAGGCACCCTGTCTTTGTCTCCAGGGGAAAGAGCCACCCTCTCCTGCAG
GGCCAGTCAGAGTCTTAGCAGCAGTGTTAGCAGCAGCTACTTAGCCTGGTACCAGCAGAAACCTGGCCAGGCTCCC
TCATCTATGGTGCATCCACCAGGGCCACTGGTATCCCAGCCAGGTTCAGTGGCAGTGGGTCTGGGACAGAC
TTCACTCTCACCATCAACAGCCTAGAGCCTGAAGATTTTGCAGTTTATTACTGTCAGCAGCGTAGCAACTG
GCCTCCGGGTACACTTTTGGCCAGGGGACCAAGGTGGAGATCAAACGAACTGTGGCTGCACCATCTGTCT
TCATCTTCCCGCCATCTGATGAGCAGTTGAAATCTGGAACTGCCTCTGTTGTGTGCCTGCTGAATAACTTC
TATCCCAGAGAGGCCAAAGTACAGTGGAAGGTGGATAACGCCCTCCAATCGGGTAACTCCCAGGAGAGTGT
CACAGAGCAGGACAGCAAGGACAGCACCTACAGCCTCAGCAGCACCCTGACGCTGAGCAAAGCAGACTACG
AGAAACACAAAGTCTACGCCTGCGAAGTCACCCATCAGGGCCTGAGCTCGCCCGTCACAAAGAGCTTCAAC
AGGGGAGAGTGTTAA  (SEQ ID NO: 2)

Heavy Chain
GAGGTCCAGCTGGTGCAGTCTGGGGGAGGCCTGGTCAAGCCTGGGGGGTCCCTGAGACTCTCCTGTGCAGC
CTCTGGATTCACCTTTAGCAGCTATGCCATGAGCTGGGTCCGCCAGGCTCCAGGGAAGGGGCTGGAGTGGG
TCTCAGCTATTAGTGGTAGTGGTAGTAGCACATACTACGCAGACTCCGTGAAGGGCCGGTTCACCATCTCC
AGAGACAATTCCAAGAACACACTGTATCTCAAATGAGCAGTCTGAGAGCTGAGGACACGGCTGTGTATTA
CTGTGTGAAAGATCTCGGTATAGCAGCTCGGTTCCGTCGGGTGCTTTTGATATCTGGGGCCAAGGGA
CAATGGTCACCGTCTCAAGCGCCTCCACCAAGGGCCCATCGGTCTTCCCCCTGGCACCCTCCTCCAAGAGC
ACCTCTGGGGGCACAGCGGCCCTGGGCTGCCTGGTCAAGGACTACTTCCCCGAACCGGTGACGGTGTCGTG
GAACTCAGGCGCCCTGACCAGCGGCGTGCACACCTTCCCGGCTGTCCTACAGTCCTCAGGACTCTACTCCC
TCAGCAGCGTAGTGACCGTGCCCTCCAGCAGCTTGGGCACCCAGACCTACATCTGCAACGTGAATCACAAG
CCCAGCAACACCAAGGTGGACAAGAAAGTTGAGCCCAAATCTTGTGCGCCGCACATCATCATCACCATCA
CGGGCCGCAACAAAAACTCATCTNAGAAGAGGATCTGAATGGGGCCGCATAG
(SEQ ID NO: 4)

FIG. 2B

E2 nucleic acid sequences
Light Chain
GATATCCAGATGACCCAGAGCCCGTCTAGCCTGAGCGCGAGCGTGGGTGATCGTGTGACCATTACCTGCAG
AGCGAGCCAGGGCCATTAGCAGCTATCTGGCGTGGTACCAGCAGAAACCAGGTAAAGCACCGAAACTATTAA
TTTATGCAGCCAGCAGCTTTGCAAAGCGGGGTCCCGTCCGTTTTTAGCGGCTCTGGATCCGCACTGATTTT
ACCCTGACCATTAGCAGCCTGCAACCTGAAGACTTTGCGGTTTATTATTGCCAGCAGCAATGGTAATCTTCC
TTATACCTTTGGCGACGGGACCAAGGTGGAGATCAAACGAACTGTGGCTGCACCATCTGTCTTCATCTTCC
CGCCATCTGATGAGCAGTTGAAATCTGGAACTGCCTCTGTTGTGTGCCTGCTAATAACTTCTATCCCAGA
GAGGCCAAAGTACAGTGGAAGGTGGATAACGCCCTCCAATGGGTAACTCCCAGGAGAGTGTCACAGAGCA
GGACAGCAAGGACAGCACCTACAGCCTCAGCAGCACCCTGACGCTGAGCAAAGCAGACTACGAGAAACA
AAGTCTACGCCTGCGAAGTCACCCATCAGGGCCTGAGCTCGCCCGTCACAAAGAGCTTCAACAGGGGAGAG
TGT (SEQ ID NO: 6)

Heavy Chain
ATGGCCCAGGTGCAGTCGGTGCAGTCTGGGGGAGGCCTGGTCAAGCCTGGGGGGTCCCTGAGACTCTCCTG
TGCAGCCTCTGGATTCACCTTTAGCAGCTATGCCATGAGCTGGGTCCGCCAGGCTCCAGGGAAGGGGCTGG
AGTGGGTCTCAGCTATTAGTGGTAGTGGTAGCACATACTACGCAGACTCCGTGAAGGGCCGGTTCACC
ATCTCCAGAGACAATTCCAAGAACACTCTGTATCTTCAAATGAGCAGTCTGAGAGCTGAGGACACGGCTGT
GTATTACTGTGCGCGTCCTTTATCTTACTTATCCTCAGCGTCCTGGTCGTCAGAATGTTTCTCCTTTTGATA
ATTGGGGCCAAGGGACAATGGTCACCGTCTCGAGCGCCTCCACCAAGGGCCCATCGGTCTTCCCCCTGGCA
CCCTCCTCCAAGAGCACCTCTGGGGGCACAGCGGCCCTGGGCTGCCTGGTCAAGGACTACTTCCCCGAACC
GGTGACGGTGTCGTGGAACTCAGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTGGGCACCCAGACCTACATCTGC
AACGTGAATCACAAGCCCAGCAACACCAAGGTGGACAAGAAAGTTGAGCCCAAATCTTGTGCGCCACA
TCATCATCACCATCACGGGCCGCAGAACAAAAACTCATCTCAGAAGAGGATCTGAATGGGGCCGCA
(SEQ ID NO: 8)

FIG. 2B (Cont.)

| Point Mutant / Inhibitor Ki Values | | |
|---|---|---|
|  | $K_i$ (pM) | Fold Difference |
| MT-SP1 | 392 |  |
| Q38A | 383 | 0.98 |
| I41A | 989 | 2.5 |
| I60A | 2055 | 5.2 |
| D60aA | 2176 | 5.6 |
| D60bA | 1369 | 3.5 |
| R60CA | 172 | 0.44 |
| F60eA | 1053 | 2.7 |
| R60fA | 615 | 1.6 |
| Y60gA | 942 | 2.4 |
| R87A | 592 | 1.5 |
| F94A | 280 | 0.71 |
| N95A | 1590 | 4.1 |
| D96A | >1uM | 10000 |
| F97A | >1uM | 10000 |
| T98A | 226 | 0.58 |
| H143A | 369 | 0.94 |
| Q145A | 336 | 0.86 |
| Y146A | 3119 | 8.0 |
| T150A | 206 | 0.53 |
| L153A | 563 | 1.4 |
| E169A | 1376 | 3.5 |
| Q174A | 614 | 1.6 |
| Q175A | 711 | 1.8 |
| D217A | 98658 | 252 |
| Q221aA | 289 | 0.74 |
| R222A | 744 | 1.9 |
| K224A | 2052 | 5.2 |

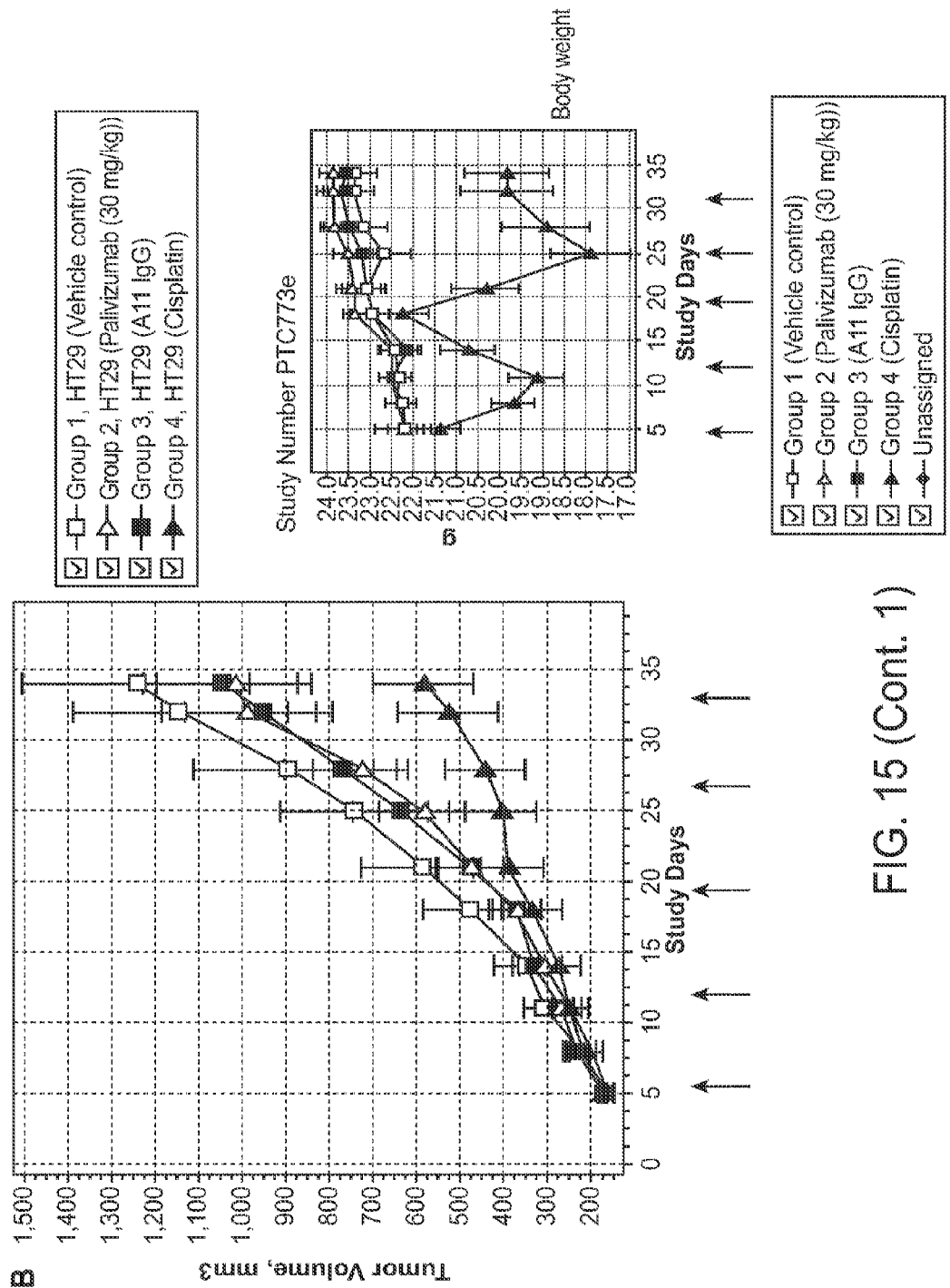
FIG. 15 (Cont. 1)

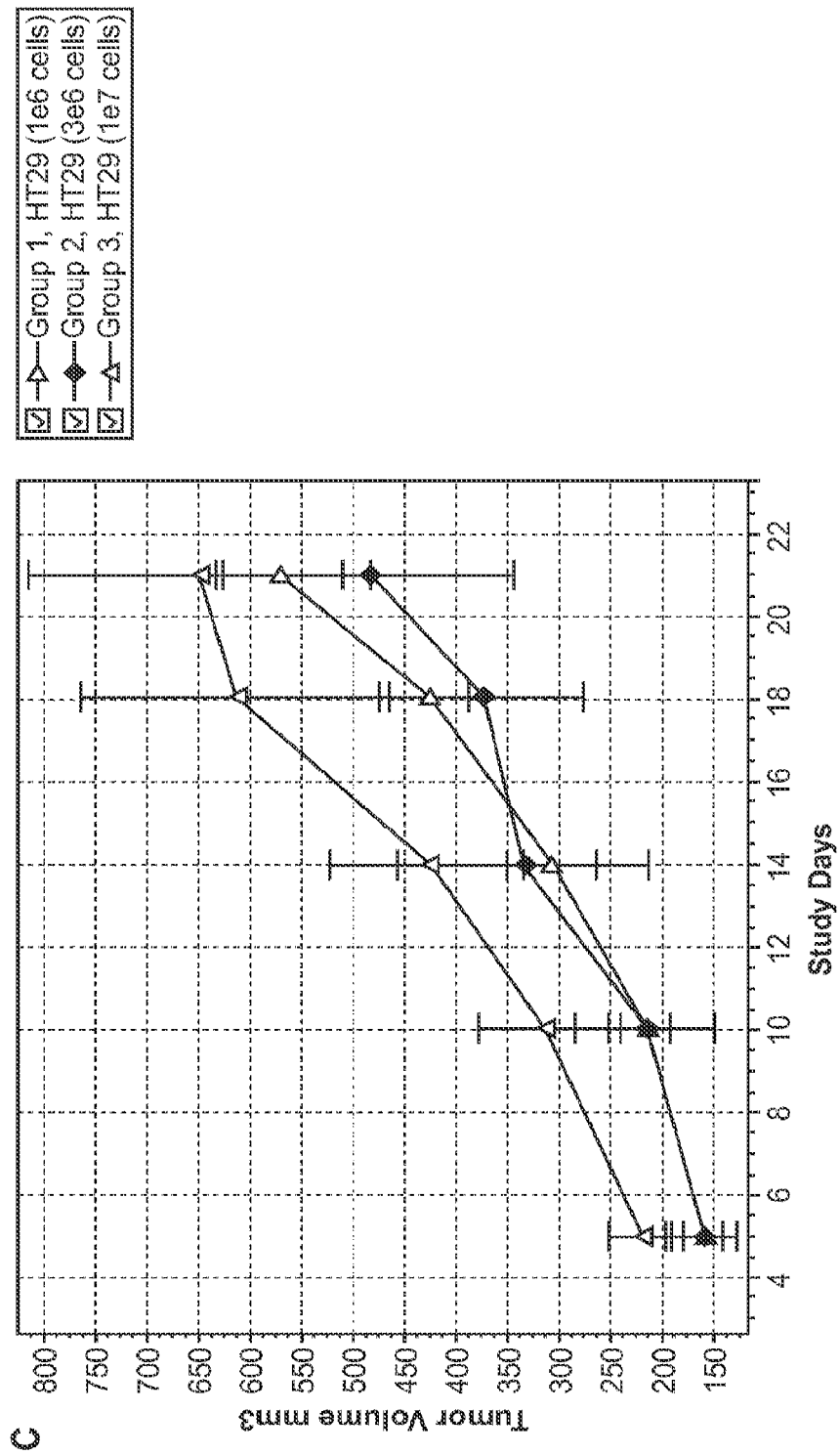
FIG. 15 (Cont. 2)

SEQUENCE LISTING

<160> NUMBER OF SEQ ID NOS: 42

<210> SEQ ID NO 1
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 1

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Thr Arg Ala Thr Gly Ile Pro Ala Arg Phe Ser
     50                  55                  60

Gly Ser Gly Ser Gly Thr Asp Phe Thr Leu Thr Ile Asn Ser Leu Glu
 65                  70                  75                  80

Pro Glu Asp Phe Ala Val Tyr Tyr Cys Gln Gln Arg Ser Asn Trp Pro
                 85                  90                  95

Pro Gly Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 2
<211> LENGTH: 654
<212> TYPE: DNA
<213> ORGANISM: Artificial Sequence
<220> FEATURE:
<223> OTHER INFORMATION: Synthetic oligonucleotide

<400> SEQUENCE: 2

```
gaaattgtgt tgacgcagtc tccaggcacc ctgtctttgt ctccagggga agagccacc      60 ctctcctgca gggccagtca gagtgttagc agcagctact tagcctggta ccagcagaaa   120
cctggccagg ctcccaggct cctcatctat ggtgcatcca ccagggccac tggtatccca   180
gccaggttca gtggcagtgg gtctgggaca gacttcactc tcaccatcaa cagcctagag   240
cctgaagatt ttgcagttta ttactgtcag cagcgtagca actggcctcc ggggtacact   300
tttggccagg ggaccaaggt ggagatcaaa cgaactgtgg ctgcaccatc tgtcttcatc   360
ttcccgccat ctgatgagca gttgaaatct ggaactgcct ctgttgtgtg cctgctgaat   420
aacttctatc ccagagaggc caaagtacag tggaaggtgg ataacgccct ccaatcgggt   480
```

```
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg ttaa          654
```

<210> SEQ ID NO 3
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 3

```
Glu Val Gln Leu Val Gln Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Ser Ser Leu Arg Ala Glu Asp Thr Ala Val Tyr Tyr Cys
                 85                  90                  95

Val Lys Asp Leu Gly Ile Ala Ala Arg Arg Phe Val Ser Gly Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Ala Ala Ala
225                 230
```

<210> SEQ ID NO 4
<211> LENGTH: 765
<212> TYPE: DNA
<213> ORGANISM: Artificial Sequence
<220> FEATURE:
<223> OTHER INFORMATION: Synthetic oligonucelotide
<220> FEATURE:
<221> NAME/KEY: misc_feature
<222> LOCATION: 737
<223> OTHER INFORMATION: n = A,T,C or G

<400> SEQUENCE: 4

```
gaggtccagc tggtgcagtc tgggggaggc ctggtcaagc tgggggggtc cctgagactc     60
tcctgtgcag cctctggatt cacctttagc agctatgcca tgagctgggt ccgccaggct    120
```

```
ccagggaagg ggctggagtg ggtctcagct attagtggta gtggtggtag cacatactac    180
gcagactccg tgaagggccg gttcaccatc tccagagaca attccaagaa cactctgtat    240
cttcaaatga gcagtctgag agctgaggac acggctgtgt attactgtgt gaaagatctc    300
ggtatagcag ctcgtcggtt cgtgtcgggt gcttttgata tctggggcca agggacaatg    360
gtcaccgtct caagcgcctc caccaagggc ccatcggtct tccccctggc acctcctcc     420 aagagcacct ctggggggcac agcggccctg ggctgcctgg tcaaggacta cttccccgaa    480
ccggtgacgg tgtcgtggaa ctcaggcgcc ctgaccagcg gcgtccacac cttcccggct    540
gtcctacagt cctcaggact ctactccctc agcagcgtag tgaccgtgcc ctccagcagc    600
ttgggcaccc agacctacat ctgcaacgtg aatcacaagc ccagcaacac caaggtggac    660
aagaaagttg agcccaaatc ttgtgcggcc gcacatcatc atcaccatca cggggccgca    720
gaacaaaaac tcatctnaga agaggatctg aatggggccg catag                    765
```

<210> SEQ ID NO 5
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 5

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln His Gly Asn Leu Pro Tyr
                 85                  90                  95

Thr Phe Gly Asp Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 6
<211> LENGTH: 642
<212> TYPE: DNA

<213> ORGANISM: Artificial Sequence
<220> FEATURE:
<223> OTHER INFORMATION: Synthetic oligonucleotide

<400> SEQUENCE: 6

```
gatatccaga tgacccagag cccgtctagc ctgagcgcga gcgtgggtga tcgtgtgacc    60
attacctgca gagcgagcca gggcattagc agctatctgg cgtggtacca gcagaaacca   120
ggtaaagcac cgaaactatt aatttatgca gccagcagct tgcaaagcgg ggtcccgtcc   180
cgttttagcg gctctggatc cggcactgat tttaccctga ccattagcag cctgcaacct   240
gaagactttg cggtttatta ttgccagcag catggtaatc ttccttatac ctttggcgac   300
gggaccaagg tggagatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 7
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 7

```
Met Ala Gln Val Gln Leu Val Gln Ser Gly Gly Gly Leu Val Lys Pro
  1               5                  10                  15

Gly Gly Ser Leu Arg Leu Ser Cys Ala Ala Ser Gly Phe Thr Phe Ser
             20                  25                  30

Ser Tyr Ala Met Ser Trp Val Arg Gln Ala Pro Gly Lys Gly Leu Glu
         35                  40                  45

Trp Val Ser Ala Ile Ser Gly Ser Gly Gly Ser Thr Tyr Tyr Ala Asp
     50                  55                  60

Ser Val Lys Gly Arg Phe Thr Ile Ser Arg Asp Asn Ser Lys Asn Thr
 65                  70                  75                  80

Leu Tyr Leu Gln Met Ser Ser Leu Arg Ala Glu Asp Thr Ala Val Tyr
                 85                  90                  95

Tyr Cys Ala Arg Pro Tyr Leu Thr Tyr Pro Gln Arg Arg Gly Pro Gln
            100                 105                 110

Asn Val Ser Pro Phe Asp Asn Trp Gly Gln Gly Thr Met Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220
```

```
Asp Lys Lys Val Glu Pro Lys Ser Cys Ala Ala Ala
225                 230                 235
```

```
<210> SEQ ID NO 8
<211> LENGTH: 777
<212> TYPE: DNA
<213> ORGANISM: Artificial Sequence
<220> FEATURE:
<223> OTHER INFORMATION: Synthetic oligonucleotide

<400> SEQUENCE: 8
atggcccagg tgcagctggt gcagtctggg ggaggcctgg tcaagcctgg ggggtccctg      60
agactctcct gtgcagcctc tggattcacc tttagcagct atgccatgag ctgggtccgc     120
caggctccag ggaaggggct ggagtgggtc tcagctatta gtggtagtgg tggtagcaca     180
tactacgcag actccgtgaa gggccggttc accatctcca gagacaattc caagaacact     240
ctgtatcttc aaatgagcag tctgagagct gaggacacgg ctgtgtatta ctgtgcgcgt     300
ccttatctta cttatcctca gcgtcgtggt cctcagaatg tttctccttt tgataattgg     360
ggccaaggga caatggtcac cgtctcaagc gcctccacca agggcccatc ggtcttcccc     420
ctggcaccct cctccaagag cacctctggg gcacagcgg cctggctg cctggtcaag      480 gactacttcc ccgaaccggt gacggtgtcg tggaactcag cgccctgac cagcggcgtc      540 cacaccttcc cggctgtcct acagtcctca ggactctact ccctcagcag cgtagtgacc     600
gtgccctcca gcagcttggg cacccagacc tacatctgca acgtgaatca caagcccagc     660
aacaccaagg tggacaagaa agttgagccc aaatcttgtg cggccgcaca tcatcatcac     720
catcacgggg ccgcagaaca aaaactcatc tcagaagagg atctgaatgg ggccgca        777
```

```
<210> SEQ ID NO 9
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 9

Gly Ile Ala Ala Arg Arg Phe
1               5
```

```
<210> SEQ ID NO 10
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 10

Asp Leu Gly Ile Ala Ala Arg Arg Phe Val Ser Gly Ala Phe Asp Ile
1               5                   10                  15
```

```
<210> SEQ ID NO 11
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 11

Pro Gln Arg Arg Gly Pro
1               5
```

```
<210> SEQ ID NO 12
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 12

Pro Tyr Leu Thr Tyr Pro Gln Arg Arg Gly Pro Gln Asn Val Ser Pro
1               5                   10                  15

Phe Asp Asn

<210> SEQ ID NO 13
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 13

Gly Ile Ala Arg Met Phe
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Gly Ile Ala Ala Met Arg Phe
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Gly Ile Ala Ala Met Met Phe
1               5

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide

<400> SEQUENCE: 16

Arg Ala Ser Gln Ser Val Ser Ser Ser Tyr Leu Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Gly Ala Ser Thr Arg Ala Thr
1               5
```

-continued

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18

Gln Gln Arg Ser Asn Trp Pro Pro Gly Tyr Thr
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Gly Phe Thr Phe Ser Ser Tyr Ala Met Ser
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Ala Ile Ser Gly Ser Gly Gly Ser Thr Tyr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide

<400> SEQUENCE: 21

Arg Ala Ser Gln Gly Ile Ser Ser Tyr Leu Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

Ala Ala Ser Ser Leu Gln Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Gln Gln His Gly Asn Leu Pro Tyr Thr
1               5

```
<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Gly Phe Thr Phe Ser Ser Tyr Ala Met Ser
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide

<400> SEQUENCE: 25

Ala Ile Ser Gly Ser Gly Gly Ser Thr Tyr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide

<400> SEQUENCE: 26

Gly Phe Thr Phe Ser Ser Tyr Ala Met Ser
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic peptide

<400> SEQUENCE: 27

Gly Val Thr Gly Ser Ser Tyr Ala Met Ser
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Synthetic peptide

<400> SEQUENCE: 28

Ala Ile Ser Gly Ser Gly Gly Ser Thr Tyr Tyr Ala Asp Ser Val Lys
1               5                   10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: Synthetic peptide

<400> SEQUENCE: 29

Ala Ile Ser Ser Ser Gly Val Asn Thr His Tyr Ala Asp Ser Val Lys
1               5                   10                  15
```

Gly

<210> SEQ ID NO 30
<211> LENGTH: 16
<212> TYPE: PRT
<213> ORGANISM: Artificial Sequence
<220> FEATURE:
<223> OTHER INFORMATION: Synthetic peptide

<400> SEQUENCE: 30

Ala Ile Ser Ser Gly Gly Asn Thr His Tyr Ala Asp Ser Val Lys Gly
1               5                   10                  15

<210> SEQ ID NO 31
<211> LENGTH: 13
<212> TYPE: PRT
<213> ORGANISM: Artificial Sequence
<220> FEATURE:
<223> OTHER INFORMATION: Synthetic peptide

<400> SEQUENCE: 31

Ile Ala Ser Ile Ala Leu Arg Gly Tyr Tyr Phe Asp Tyr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic peptide

<400> SEQUENCE: 32

Ile Ala Ser Ile Ala Thr Arg Gly Tyr Phe Phe Asn Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic peptide

<400> SEQUENCE: 33

Arg Ala Ser Gln Ser Val Ser Ser Tyr Leu Ala
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic peptide

<400> SEQUENCE: 34

Arg Ala Ser Gln Thr Phe Gly Ser Ser Tyr Leu Ala
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic peptide

<400> SEQUENCE: 35

Arg Ala Ser Gln Ile Phe Ser Ser Asn Ser Leu Ala

```
                1               5                    10
```

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide

<400> SEQUENCE: 36

Gly Ala Ser Ser Arg Ala Thr
 1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide

<400> SEQUENCE: 37

Gln Gln Tyr Gly Ser Ser Pro Trp Thr
 1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide

<400> SEQUENCE: 38

Gly Ile Ala Ala Arg Met Phe
 1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2
<223> OTHER INFORMATION: Xaa = Any Amino Acid

<400> SEQUENCE: 39

Pro Xaa Arg Arg Gly Pro
 1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2
<223> OTHER INFORMATION: Xaa = Any Amino Acid

<400> SEQUENCE: 40

Pro Xaa Arg Met Gly Pro
 1               5

<210> SEQ ID NO 41
<211> LENGTH: 6
<212> TYPE: PRT

```
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2
<223> OTHER INFORMATION: Xaa = Any Amino Acid

<400> SEQUENCE: 41

Pro Xaa Met Arg Gly Pro
 1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2
<223> OTHER INFORMATION: Xaa = Any Amino Acid

<400> SEQUENCE: 42

Pro Xaa Met Met Gly Pro
 1               5
```

ANTIBODIES AND METHODS OF USE THEREOF

CROSS-REFERENCE TO RELATED APPLICATIONS

This application claims priority benefit to U.S. provisional application Ser. No. 61/176,461 filed on May 7, 2009, which application is incorporated herein by reference in its entirety.

STATEMENT REGARDING FEDERALLY SPONSORED RESEARCH

This invention was made with government support under grants nos. CA072006 and T32 CA108462 awarded by the National Institutes of Health. The government has certain rights in this invention.

INTRODUCTION

Investigation into the use of antibodies as therapeutics has increased significantly over the past decade. The high specificity and tight binding characteristics inherent to antibodies give them enormous potential for use as therapeutics. Their specificity allows for precise targeting of protein functions, which may minimize side effects resulting from off-target binding. Therapeutic antibodies currently in use function through three modes of action: as inducers of the immune system cytotoxicity, as carriers of a specific cytotoxic agent, or as inhibitors of the target protein function.

To date, the majority of therapeutic antibodies have fallen into this last grouping, acting as antagonists of proteins in disease related signaling pathways such as VEGF (Avastin), EGFR (Erbitux) and TNF (Humira). By combining selectivity and a large binding footprint, antibodies have proven to be ideal for creating the steric hindrance necessary to block ligand/receptor interactions and inhibit the signaling cascade and downstream functions involved in disease progression.

Many diseases have also been found to be dependent upon misregulated enzyme function, including proteases. In particular, proteases have been implicated in a number of functions essential for cancer progression. These include extracellular matrix remodeling, release of cytokines, and loss of apoptotic response. One particular protease that has been implicated in cancer progression is the trypsin-fold serine protease MT-SP1 (membrane type-serine protease 1, matriptase) (Uhland K *Cell Mol Life Sci* 2006, 63: 2968-78). MT-SP1 is over-expressed on the surface of epithelial cells involved in a variety of cancers, including breast, colon and prostate cancers. The protease is involved in the activation of other proteases, growth factors and receptors all of which result in extracellular matrix remodeling, angiogenesis and invasive growth.

Recent studies have investigated the use of antibodies as inhibitors of protease function (Farady C J et al. *J Mol Biol* 2008, 380: 351-60; Farady C J et al. *J Mol Biol* 2007, 369: 1041-51; Sun J et al. *Biochemistry* 2003, 42, 892-900). The inhibitors were found to either block substrate binding through steric hindrance or cause conformational changes due to binding at allosteric sites. More recently, the molecular basis of three antibody inhibitors have been determined from crystal structures of the antibody/protease complexes (Farady C J et al. *J Mol Biol* 2008, 380: 351-601).

LITERATURE

Sun J et al. *Biochemistry* 2003, 42, 892-900; Farady C J et al. *J Mol Biol* 2007, 369: 1041-5; Farady C J et al. *J Mol Biol* 2008, 380: 351-601; Foltz et al. (US Patent Publication No. 2006/0171884); Foltz et al. American Society of Hematology Annual Meeting Abstracts 2005, 106:Abstract 4816.

SUMMARY

The present disclosure relates to protease-binding agents (e.g. antibodies) that bind to and modulate the activity of a protease, compositions comprising the antibodies, and methods involving use of the antibodies or compositions.

Also provided by the disclosure is an isolated protease-binding agent comprising a heavy chain variable region comprising a CDR; and a light chain variable region comprising a CDR, in which a hypervariable loop of said heavy chain variable region is capable of binding the S1 pocket of a P1-Arg-specific protease to position a scissile bond in the active site of said protease in an orientation opposite to a cleavable substrate of said protease; and in which the heavy chain variable region and the light chain variable region provide for antigen specificity so as to position the hypervariable loop for binding to said S1 pocket. Other agents can include those that bind to the protease in such a away that the scissile bond of the binding agent is positioned away from the active site of said protease, particularly away from the active site nucleophile.

Methods of the present disclosure include administering a composition comprising a protease-binding agent that inhibits a protease of interest to treat diseases, such as cancer or infection.

Methods also may employ the protease-binding agent for diagnosis of diseases.

Methods of screening are also provided to identify or engineer a protease-binding agent that specifically inhibits a protease of interest.

Kits containing one or more compositions of the present disclosure, as well as those with instructions for use in a method of the present disclosure also are provided.

Other features of the invention are described herein, and will also be readily apparent to the ordinarily skilled artisan upon reading the present disclosure.

BRIEF DESCRIPTION OF FIGURES

FIG. 1 depicts the relative inhibition of MT-SP1 by seven Fabs identified from the phage display library.

DETAILED DESCRIPTION OF EXEMPLARY EMBODIMENTS

Figure 2C:
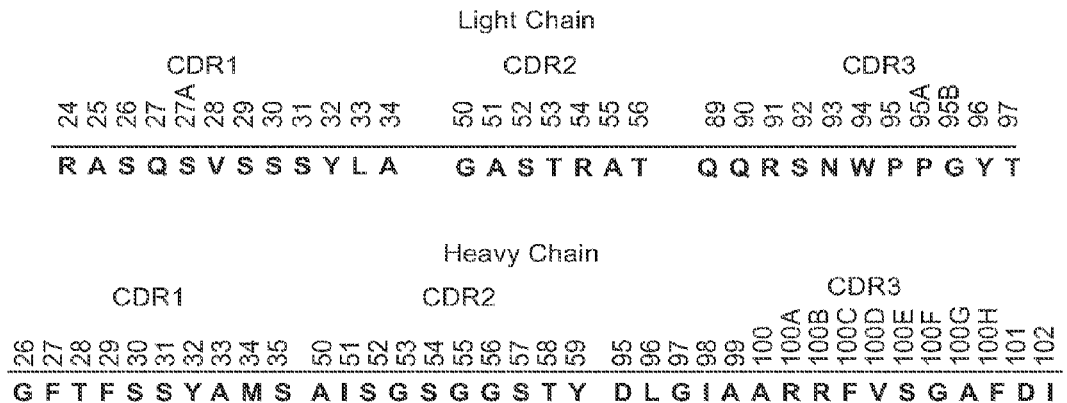
FIG. 2, panel A shows the amino acid sequences of the A11 and E2 heavy and light chain polypeptides, with the CDRs underlined in the sequences. CDRS are defined by the Kabat numbering system (Johnson et al. *Nucleic Acids Research*, 2000, 28: 214-218). Panel B shows the nucleic acid sequences that encode heavy and light chains of A11 and E2 antibodies. Nucleic acid sequences encoding the CDRs are bolded. Panel C shows the CDRs of A11 separately from the rest of the amino acid sequences.

The present disclosure relates to antibodies that bind to and modulate the activity of a protease, compositions comprising the antibodies, and methods involving use of the antibodies or compositions.

Certain of the antibodies disclosed herein were first found by screening a human Fab phage display library for inhibition of a type II transmembrane multidomain serine protease MT-SP1/matriptase. Structural studies of the complex between the antibody and the protease reveal that the antibody comprises features that enable potent inhibition of the protease as well as other features that render the antibodies specific for a protease of interest. The data presented herein support the application of the antibodies in methods and compositions, including the diagnosis and treatment of multiple types of human diseases (e.g. cancer).

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "an antigen" includes a plurality of such antigens and reference to "the peptide" includes reference to one or more peptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

When describing the compositions, pharmaceutical formulations containing such, and methods of producing and using such compositions, the following terms have the following meanings unless otherwise indicated. It should also be understood that any of the moieties defined forth below may be substituted with a variety of substituents, and that the respective definitions are intended to include such substituted moieties within their scope.

The terms "polypeptide" and "protein" are used interchangeably throughout the application and mean at least two covalently attached amino acids, which includes proteins, polypeptides, oligopeptides, peptides, and fragments thereof. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. Normally, the amino acids are in the (S) or L-configuration. If non-naturally occurring side chains are used, non-amino acid substituents may be used, for example to prevent or retard in vivo degradation. Naturally occurring amino acids are normally used and the protein is a cellular protein that is either endogenous or expressed recombinantly. The terms includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 5-50 residues (e.g., 8-20 residues) in length.

As used herein, the term "endogenous," refers to biomolecules that originate within an organism in nature. For example, an endogenous substrate of a protease is a protein that originates from the same organism as the source of the protease and is capable of specifically binding to the protease under physiological conditions and of which a peptidic bond is cleaved by the protease. As another example, an endogenous substrate of a serine protease is a protein that originates from the same organism as the source of the serine protease and is capable of specifically binding to the serine protease under physiological conditions and of which a peptidic bond is cleaved by the serine protease.

As used herein, the term "cleavable," refers to protease substrates, of which one or more peptidic bonds can be hydrolyzed by the protease.

As used herein, the term "orientation," refers to the positional relationship of a protease substrate relative the protease to which it is bound. By convention, the orientation of a substrate to its protease is specified from N-terminus to C-terminus based on sites named Pn, ..., P3, P2, P1, P1', P2', P3', ..., Pn', where P1-P1' denotes the scissile bond to be cleaved by the protease and n is the number of the feature relative to the scissile bond. Their respective binding sites on the protease are named Sn, ..., S3, S2, S1, S1', S2', S3', ..., Sn' and n is the number of the feature relative to the active site. In accordance with this nomenclature, the scissile bond of a cleavable substrate is presented to the active site in an N-terminus to C-terminus orientation relative to sites S1 and S1'. If the scissile bond of a substrate is presented to the active site in a C-terminus to N-terminus orientation relative to sites S1 and S1', the scissile bond is considered to be in the "reversed orientation."

By "nucleic acid" herein is meant either DNA or RNA, or molecules which contain both deoxy- and ribonucleotides. Nucleic acid may be naturally occurring or synthetically made, and as such, includes analogs of naturally occurring polynucleotides in which one or more nucleotides are modified over naturally occurring nucleotides.

The term "analog" or "analogue" refers to without limitation any compound which has structural similarity to the compounds of the present disclosure and would be expected, by one skilled in the art, to exhibit the same or similar utility as the claimed and/or referenced compounds.

The term "carrier" as used in the context of a carrier conjugated to an antibody includes a peptide or protein carrier, a non-peptide or protein carrier (e.g. a non-peptide polymer).

The term "cell surface antigen" (or "cell surface epitope") refers to an antigen (or epitope) on surface of a cell that is extracellularly accessible at any cell cycle stage of the cell, including antigens that are extracellularly accessible during all stages of the cell cycle. "Extracellularly accessible" in this context refers to an antigen that can be bound by an antibody provided outside the cell without need for permeabilization of the cell membrane.

The term "chemotherapy" as used herein refers to use of an agent (e.g., drug, antibody, etc.), particularly an agent(s) that is selectively destructive to a cancerous cell, in treatment of a disease, with treatment of cancer being of particular interest.

A "cancer cell" as used herein refers to a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell" or "cancerous cell", and encompasses cancer cells of a solid tumor, a semi-solid tumor, a primary tumor, a metastatic tumor, and the like.

The term "conjugated" generally refers to a chemical linkage, either covalent or non-covalent, usually covalent, that proximally associates one molecule of interest with second molecule of interest.

The terms "antigen" and "epitope" are well understood in the art and refer to the portion of a macromolecule (e.g., a polypeptide) which is specifically recognized by a component of the immune system, e.g., an antibody or a T-cell antigen receptor. As used herein, the term "antigen" encompasses antigenic epitopes, e.g., fragments of an antigen which are antigenic epitopes. Epitopes can be recognized by antibodies in solution, e.g. free from other molecules. Epitopes can be recognized by T-cell antigen receptor when the epitope is associated with a class I or class II major histocompatibility complex molecule.

The terms "derivative" and "variant" refer to without limitation any compound or antibody which has a structure or sequence derived from the compounds and antibodies of the present disclosure and whose structure/sequence is sufficiently similar to those disclosed herein and based upon that similarity, would be expected, by one skilled in the art, to exhibit the same or similar activities and utilities as the claimed and/or referenced compounds or antibody.

The term "effective amount" of a composition as provided herein is intended to mean a non-lethal but sufficient amount of the composition to provide the desired utility. For instance, for eliciting a favorable response in a subject to treat a disorder or infection, the effective amount is the amount which eliminates or diminishes the symptoms associated with the disorder, e.g., so as to provide for control of cancer metastatis, to eliminate cancer cells, decrease bacterial or viral infection. As will be pointed out below, the exact amount required will vary from subject to subject, depending on the species, age, and general condition of the subject, the severity of the condition or disease that is being treated, the particular composition used, its mode of administration, and the like. Thus, it is not possible to specify an exact "effective amount." However, an appropriate effective amount may be determined by one of ordinary skill in the art using only routine experimentation.

The term "immunotherapy" refers to treatment of disease (e.g., viral or bacterial infection, or cancer) by modulating an immune response to a disease antigen. In the context of the present application, immunotherapy refers to providing an antibacterial and/or anti-cancer immune response in a subject by administration of an antibody (e.g., a monoclonal antibody).

The term "in combination with" as used herein refers to uses where, for example, a first therapy is administered during the entire course of administration of a second therapy; where the first therapy is administered for a period of time that is overlapping with the administration of the second therapy, e.g. where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

The term "isolated" is intended to mean that a compound is separated from all or some of the components that accompany it in nature. "Isolated" also refers to the state of a compound separated from all or some of the components that accompany it during manufacture (e.g., chemical synthesis, recombinant expression, culture medium, and the like).

The term "antibody" (also used interchangeably with "immunoglobulin") encompasses polyclonal and monoclonal antibody preparations where the antibody may be of any class of interest (e.g., IgM, IgG, and subclasses thereof), as well as preparations including hybrid antibodies, altered antibodies, F(ab')$_2$ fragments, F(ab) molecules, Fv fragments, single chain fragment variable displayed on phage (scFv), single chain antibodies, single domain antibodies, diabodies, chimeric antibodies, humanized antibodies, and functional fragments thereof which exhibit immunological binding properties of the parent antibody molecule. In some embodiments, e.g., cancer therapy, antibodies that provide for complement-mediated killing and/or antibody-dependent cellular cytotoxicity (ADCC) are of particular interest. The antibodies described herein may be detectably labeled, e.g., with a radioisotope, an enzyme which generates a detectable product, a fluorescent protein, and the like. The antibodies may be further conjugated to other moieties, such as a cytotoxic molecule or other molecule (e.g., to provide for delivery of an anti-cancer drug to a cancer cell), members of specific binding pairs, e.g., biotin (member of biotin-avidin specific binding pair), and the like. The antibodies may also be bound to a support (e.g., a solid support), such as a polystyrene plate or bead, test strip, and the like.

Immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (usually of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

An immunoglobulin light or heavy chain variable region is composed of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, 1991, and Lefranc et al. IMGT, the international ImMunoGeneTics information System®. Nucl. Acids Res., 2005, 33, D593-D597)). A detailed discussion of the Kabat numbering system is provided on the World Wide Web at kabatdatabase.com/index.html. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

The term "monoclonal antibody" refers to an antibody composition having a homogeneous antibody population. The term is not limited by the manner in which it is made. The term encompasses whole immunoglobulin molecules, as well as Fab molecules, F(ab')2 fragments, Fv fragments, single chain fragment variable displayed on phage (scFv), fusion proteins comprising an antigen-binding portion of an antibody and a non-antibody protein, and other molecules that exhibit immunological binding properties of the parent monoclonal antibody molecule. Methods of making polyclonal and monoclonal antibodies are known in the art and described more fully below.

The term "specific binding of an antibody" or "antigen-specific antibody" in the context of a characteristics of an antibody refers to the ability of an antibody to preferentially bind to a particular antigen that is present in a homogeneous mixture of different antigens. In certain embodiments, a specific binding interaction will discriminate between desirable and undesirable antigens (or "target" and "non-target" antigens) in a sample, in some embodiments more than about 10 to 100-fold or more (e.g., more than about 1000- or 10,000-fold). In certain embodiments, the affinity between an antibody and antigen when they are specifically bound in an antibody-antigen complex is characterized by a $K_D$ (dissociation constant) of less than $10^{-6}$M, less than $10^{-7}$ M, less than $10^{-8}$ M, less than $10^{-9}$ M, less than $10^{-9}$ M, less than $10^{-11}$ M, or less than about $10^{-12}$ M or less.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include substitution within the following groups of amino acid residues: gly, ala; val, ile, leu; asp, glu; asn, gln; ser, thr; lys, arg; and phe, tyr. Conservative amino acid substitutions in the context of an antibody disclosed herein are selected so as to preserve the interaction between the antibody and the protease of interest.

The term "pharmaceutically acceptable" refers to a material that is not biologically or otherwise undesirable, i.e., the material is of a medically acceptable quality and composition that may be administered to an individual along with the selected active pharmaceutical ingredient without causing any undesirable biological effects or interacting in a deleterious manner with any of the other components of the pharmaceutical composition in which it is contained.

The term "pharmaceutically acceptable excipient" as used herein refers to any suitable substance which provides a pharmaceutically acceptable vehicle for administration of a compound(s) of interest to a subject. "Pharmaceutically acceptable excipient" can encompass substances referred to as pharmaceutically acceptable diluents, pharmaceutically acceptable additives and pharmaceutically acceptable carriers.

The term "purified" is intended to mean a compound of interest has been separated from components that accompany it in nature and provided in an enriched form. "Purified" also refers to a compound of interest separated from components that can accompany it during manufacture (e.g., in chemical synthesis, recombinant expression, culture medium, and the like) and provided in an enriched form. Typically, a compound is substantially pure when it is at least 50% to 60%, by weight, free from organic molecules with which it is naturally associated or with which it is associated during manufacture. Generally, the preparation is at least 75%, more usually at least 90%, and generally at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a compound that binds an antibody of interest. Purity can be measured by any appropriate method, e.g., chromatography, mass spectroscopy, HPLC analysis, etc.

The term "subject" is intended to cover humans, mammals and other animals which contain serine proteases in any fashion. The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

In the context of cancer therapies and diagnostics described herein, "subject" or "patient" is used interchangeably herein to refer to a subject having, suspected of having, or at risk of developing a tumor, where the cancer is one associated with cancerous cells expressing an active and/or dysregulated serine protease. Samples obtained from such subject are likewise suitable for use in the methods of the present disclosure.

As used herein, the terms "determining," "measuring," and "assessing," and "assaying" are used interchangeably and include both quantitative and qualitative determinations.

It is further noted that the claims may be drafted to exclude any optional or alternative element. As such, this statement is intended to serve as antecedent basis for use of such exclusive terminology as "solely", "only" and the like in connection with the recitation of claim elements, or the use of a "negative" limitation.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed. To the extent a definition of a term set out in a document incorporated herein by reference conflicts with the definition of a term explicitly defined herein, the definition set out herein controls.

Exemplary methods and compositions employable therein are described first in greater detail, followed by a review of the various specific compositions, formulations, kits and the like that may find use in the methods of the present disclosure, as well as a discussion of representative applications in which the methods and compositions of the present disclosure find use.

Protease Binding Agents

The present disclosure provides a protease binding agent, where protease binding agents include a whole antibody, an antigen-binding fragment thereof, and synthetic protease binding agents that comprises portions of an antibody. A subject protease-binding agent binds a member of a protease family such as the P1 Arg-specific protease family (e.g. trypsin-like serine proteases). An example of a protease family is the chymotrypsin-fold family, which is also called the peptidase family S1. A subject protease binding agent (e.g., antibody) finds use in a variety of applications, including use in various methods of treating a host suffering from a disease or condition, as well as in diagnosis of various diseases and conditions. For example, in some embodiments, a subject antibody is highly specific for active membrane-type serine protease I (MT-SP1), which is often found on cancer cells. More exemplary uses of a subject antibody will be described later.

As noted above, a subject protease-binding agent binds specifically to a member of a protease family such as the P1 Arg-specific protease family (e.g. serine protease family). A subject protease-binding agent exhibits features that allow not only potent inhibition of a specific protease but also specific recognition of the protease. Serine proteases are a group of enzymes that share structural and functional features discussed below. Members of the P1 Arg-specific protease family are also discussed.

Protease Targets

The target of a subject protease-binding agent is a protease that catalyzes the hydrolysis of covalent peptidic bonds.

Serine Proteases

A subject protease-binding agent includes an agent specific for a serine protease. The mechanism of catalysis is based on the nucleophilic attack of the peptidic bond by a serine. Cysteine, threonine or water molecules associated with aspartate or metals can also play the role of a nucleophile. In many cases, the nucleophilic property of the group is improved by the presence of a histidine, held by an aspartate in a basic state, so as to readily accept a proton. The aligned catalytic group of serine, histidine and aspartate is a common feature to most serine proteases. The substrate binding groove containing the active site is shaped as a cleft. In order to better describe the interaction between the polypeptide substrate and its respective serine protease, the polypeptide substrate is labeled from N-terminus to C-terminus as Pn, . . . , P3, P2, P1, P1', P2', P3', . . . , Pn' while their respective binding sites on the protease Sn, . . . , S3, S2, S1, S1', S2', S3', . . . , Sn'. In accordance with this nomenclature, P1-P1' denotes the hydrolyzed peptidic bond of the polypeptide substrate.

Chymotrypsin-Fold Serine Proteases

A subject protease-binding agent includes an agent specific for a chymotrypsin-fold serine protease. There is a large number of serine proteases that catalyze hydrolysis of peptidic bond in the manner described above. Many of them are further grouped together and collectively referred to as the chymotrypsin-fold serine protease. Chymotrypsin-fold serine proteases make up a protease family that has been extensively characterized and studied. They are often synthesized as non-active zymogens in a cell and are activated upon cleavage in a highly conserved activation motif to produce a mature protease. In addition to high degrees of amino acid sequence identity among the family members, they also share identical folds in conserved motifs. Several notable structural and functional features shared among serine proteases of this family were first characterized in the chymotrypsin protease. One prominent feature of this protein family is a structural fold containing two β-barrels, with the catalytic Ser, His, and Asp amino acids found at the interface of the two domains. Another common feature includes five enzyme-substrate hydrogen bonds at positions P1 and P3 that juxtagpose the scissile peptide bond adjacent to the Ser-His catalytic couple, such that the nucleophilic Ser O-γ is accurately positioned for the nucleophilic attack.

While very similar pockets and clefts make up the structure of the active sites of different chymotrypsin-like serine proteases, the members of this family diverge in parts of the protease distal from the active sites. Protein sequences surrounding the active site that differ among proteases within the family provide for diversity in the substrate-binding groove, and hence, the specificity for each respective proteolytic substrate. One way in which specificity is provided is based on surface loops of the protease in the substrate binding groove.

Although the protease-substrate interactions may be characterized by sequence divergence, all the structures responsible for substrate specificity (e.g. surface loops surrounding the active site) are still aligned so as to accurately position the scissile bond of the substrate in the conserved active site. As such, the positions of the catalytic amino acids in the active site, such as Ser, His, and Asp, remain the anchor that defines the common structural framework of chymotrypsin-like serine protease.

Chymotrypsin Fold Serine Protease with a Trypsin-Like S1 Pocket

A subject protease-binding agent includes an agent specific for a member a subfamily of the chomotrypsin-like serine protease. The chymotrypsin-fold serine protease family may be subdivided depending on the sequence of the P1/S1 site. In certain cases, the S1 of the protease specifically binds P1 containing an Arg or Lys so as to provide peptidic cleavage following an Arg or Lys residue (e.g. S1 in trypsin). In other embodiments, the S1 pocket is hydrophobic and specifically binds P1 containing one or more amino acid(s) having hydrophobic side chains (e.g. S1 in chymotrypsin). In this case, the peptidic cleavage occurs after the hydrophobic amino acid residue. In certain cases, the S1 pocket specifically binds P1 containing an Ala and cleaves the peptidic bond after the Ala residue (e.g. S1 in elastase).

Depending on the structural features of the protease-binding agent described in more detail below, the agent may be specific for serine proteases having a S1 pocket similar to trypsin. For simplicity, serine proteases in the chymotrypsin-fold serine protease family with a S1 pocket similar to that of trypsin would be referred herein as trypsin-like serine proteases. In certain cases, the protease target of the antibody of the present disclosure is not a serine protease but has an S1 pocket similar to that of trypsin. The proteases with a similar S1 pocket to that of trypsin regardless of whether the protease is categorically a serine protease would be referred herein as "P1-Arg-specific proteases".

Type II Transmembrane Serine Proteases

A subject protease-binding agent includes an agent specific for a Type II transmembrane serine protease. A protease-binding agent may be specific for a small group proteases within the subfamily of trypsin-like serine proteases. The protease-binding agent can be capable of binding to type II transmembrane serine proteases (TTSPs). Aside from possessing the structural framework, conserved motifs, and the S1 pocket of trypsin-like serine proteases, this group of proteases share additional features. The shared features are described in the following from N-terminus to C-terminus. At the N-terminus, a segment of a length about 12 to about 112 amino acid residues resides intracellularly and plays a putative role in protein sorting and/or intracellular signal transduction comprises. The intracellular segment is followed by a hydrophobic domain that spans the plasma membrane, making up the transmembrane domain. C-terminal to the transmembrane domain are the extracellular domains of the protein. One extracellular domain is the stem regions, which may comprise one or more of the following: low density lipoprotein (LDL) receptor class A domains, Group A scavenger receptor (SR) domains, frizzled domains, Cls/Clr, urchin embryonic growth factor and bone morphogenic protein 1 (CUB) domains, etc. Lastly, the proteolytic domain is presented at or near the C-terminus of the TTSP. See Hooper et al. *J. Biol. Chem.* 2001, 276:857-860 for more detail. There are about 17 members of TTSPs found in mammals, of which seven are found in human. See, e.g., Table 1 below.

TABLE 1

| Name | Organism | Other name | Accession number |
| --- | --- | --- | --- |
| Corin | Human | | AF133845 |
| | Mouse | LRP4 | AB013874 |
| Enteropeptidase | Human | Enterokinase | U09860 |
| | Bovine | | U09859 |
| | Mouse | | U73378 |
| | Rat | | 1589367 |
| | Porcine | | D30799 |
| MT-SP1 | Human | Matriptase | AF133086/AF118224 |
| | Mouse | Epithin | AF042822 |

TABLE 1-continued

| Name | Organism | Other name | Accession number |
|---|---|---|---|
| HAT | Human | | AB002134 |
| Hepsin | Human | | M18930 |
| | Mouse | | AF030065 |
| | Rat | | X70900 |
| Stubble-Stubloid | Drosophila | | L11451 |
| TMPRSS2 | Human | | U75329 |
| | Mouse | Epitheliasin | AF113596 |
| TMPRSS4 | Human | | AF179224 |

Membrane-Type Serine Protease I

A subject protease-binding agent can specifically bind and inhibit membrane-type serine protease I (MT-SP1). MT-SP1 is a serine protease known to facilitate cellular invasiveness and may activate oncogenic pathways. Polypeptide substrates of MT-SP1 have the following preferred residues N-terminal to the cleavage site: either an Arg or Lys residue at P4, a non-basic residue at P3, Ser at P2, and Arg at P1. At P1', the position C-terminal to the cleavage site, the preferred residue is Ala. See Uhland K Cell. Mol. Life. Sci. 2006, 63:2968-2978 for more detail. Based on this profile, a protease-binding agent can be designed to be similar to the substrate with those preferred residues and so would be capable of binding to the substrate binding groove of MT-SP1.

Structural Features of the Protease-Binding Agent

A subject protease-binding agent binds a protease, as described above, by specifically interacting with various parts of the protease, including the substrate binding groove. The agent comprises a feature for inhibiting the protease while maintaining certain level of specificity. The features responsible for inhibition and specificity are described in greater detail below.

Protease Inhibition Feature

A protease-binding agent possesses inhibitory activity against a specific protease. A subject protease-binding agent may inhibit more than one type of proteases. Protease-binding agents of the present disclosure include a structural loop that is provided by a hypervariable loop of a heavy chain variable region, which loop is capable of binding an S1 pocket of a protease so as to inhibit cleavage of a scissile bond in the protease-binding agent by the active site of said protease. Inhibition of cleavage of the scissile bond can be provided by positioning of the scissile bond in the active site of said protease in an orientation opposite to that of a cleavable substrate complexed to said protease or by positioning of the scissile bond away from the active site of said protease, particularly away from the active site nucleophile. For example, an agent, e.g., A11 antibody, can inhibit a protease by binding to a Sn site so as to reverse the orientation of the peptidic bond relative to that of a cleavable substrate when complexed with the protease. In an example of an antibody that is a protease-binding agent, certain amino acid residues or structure of the antibody may be similar to a cleavable substrate except that the scissle bond (hydrolizable peptidic bond) that is normally presented to the active site in a cleavble substrate is in a reversed (opposite) orientation. Such an antibody is described in more detail below in relation to an exemplary endogenous substrate.

As described above, in a cleavable substrate bound to a protease, the segment N-terminal to the scissile bond (Pn, ..., P2, P1) would bind to Sn, ..., S2, and S1 of the protease, while the segment C-terminal to the scissle bond (P1', P2', ..., Pn') would bind to S1', S2', ..., Sn'. The scissile bond is C-terminal to the P1 site and is presented to the active site in an N-terminus to C-terminus orientation relative to S1 and S1'. In this orientation, the scissile bond is in a cleavable conformation. In a complex between the protease and an inhibitory antibody that positions a scissile bond in a reversed orientation, the one or more loops of the antibody C-terminal to a scissile bond may bind in the S1, S2, ..., or Sn pocket, as opposed to the S1', S2', ..., or Sn' pocket. In a related embodiment, one or more loops of the antibody N-terminal to a scissile bond may bind in the S1', S2', ..., or Sn' pocket respectively as opposed to the S1, S2, ..., or Sn pocket. As a result, the scissile bond is presented to the active site in a C-terminus to N-terminus orientation, relative to the positions of S1 and S1' of the protease. This orientation of the scissile bond is opposite to, or reversed relative to the scissile bond of a cleavable substrate in complex with the protease. By presenting a reversed scissile bond in the active site of a protease, a subject protease-binding agent (e.g., an antibody) would inhibit the proteolytic activity of the protease. Utilizing the placement of a reversed scissile bond, a subject protease-binding agent can inhibit one or more members of the protease families described above. See schematic for A11 in FIG. 6B.

An exemplary inhibition feature of a protease-binding agent is a hypervariable region of an antibody comprising a loop acting as a P1 site. When bound to the S1 pocket, the P1-like loop positions a scissile bond N-terminal to the loop in the active site of the protease. As a result, the scissile bond is presented in a reversed orientation (C-terminus to N-terminus relative to the position of S1 and S1' of the protease), and since the protease cannot hydrolyze a reversed scissile bond, the protease is inhibited by the antibody. The hypervariable region comprising the loop may reside in the heavy chain. In other embodiments, the loop may reside in the light chain.

In another example, protease binding agent can also inhibit a protease by binding to a Sn site so as to position the peptidic bond away from the active site, particularly away from the active site nucleophile, at a distance further away than that of a cleavable substrate when complexed with the protease. Stated differently, the cleavable peptidic bond is positioned at distance far enough away from the active site such that the peptidic bond cannot be cleaved. In such an exemplary agent (e.g. E2 antibody), certain amino acid residues or structure of the antibody may be similar to a cleavable substrate except that the scissile bond that is normally presented to the active site in a cleavble substrate is held at a distant position from the active site. Such an antibody is described in more detail below in relation to an exemplary endogenous substrate.

In a complex between the protease and an inhibitory antibody that positions the scissile bond away from the active site, one or more loops (e.g. P2' and P3') of the antibody C-terminal to the scissile bond may bind in the S2, S3 ..., or Sn pocket, as opposed to the S2', S3', ..., or Sn' pocket while the P1 loop stays inserted in the S1 pocket. In another embodiment, one or more loops of the antibody N-terminal to a scissile bond may bind in the S2', S3', ..., or Sn' pocket respectively as opposed to the S1, S2, ..., or Sn pocket, while the P1' loop stays bound in the S1' pocket. In either of these embodiments, the scissile bond is positioned at a distance away from the active site because loops on one side of the scissile bond (either C- or N-terminal) have been flipped to interact with the pockets on the other side of the active site. In any of these two exemplary conformations, the scissile bond ends up being positioned away from the active site of a protease. Utilizing the placement of this distant scissile bond, a subject protease-binding agent can inhibit one or more members of the protease families described above. See schematic for E2 in FIG. 6B. The inhibition feature may include the P1-like loop and the other loops and turns responsible for flipping the loops to interact with pockets on the other side of the active site.

Depending on the type of amino acid residues residing on the P1-like loop, the loop may be engineered such that a subject protease-binding agent specifically inhibits a protease of interest. Since the S1 pocket of a trypsin-like serine protease comprises an Asp of which the side chain is usually negative, a P1-like loop containing amino acid residues that have positive side chains would interact favorably with the Asp residue in the S1 pocket. Accordingly, to be specific for binding to and/or inhibiting trypins-like serine proteases or P1-Arg-specific proteases, an antibody comprising a P1-like loop may contain amino acid residues such as Arg or Lys. The loop that binds to the S1 pocket of the protease of interest may be about 10, 15, 20, 25, 30 or more amino acids in length. A consensus sequence of this P1-like loop that would be specific for binding to a protease with an S1 pocket of a trypsin is RR. Another consensus sequence of this P1-like loop is GIAARRF (SEQ ID NO:9). Yet another consensus sequence of a P1-like loop is PxRRGP, such as PQRRGP (SEQ ID NO:11). Alternatively, these amino acid sequences may be modified such that one or both of the double arginines are substituted with methionines. Where one or more argines are substituted with methionines, the consensus sequence of the P1-like loop may be GIARMF (SEQ ID NO:13), GIAAMRF (SEQ ID NO:14), GIAAMMF (SEQ ID NO:15), PxRMGP, PxMRGP, or PxMMGP, in which x may be any amino acid residue.

For example, antibody A11 comprises a heavy chain variable region, in which there is a P1-like loop (named H3 in the crystal structure presented in Example 9) comprising two Arg residues. The loop binds to the S1 pocket of serine protease MT-SP1 when A11 is bound to MT-SP1 and positions a scissile bond in the reversed orientation in the active site of MT-SP1.

In a similar vein, a protease-binding agent may be specific for other subfamilies other than P1-Arg-specific proteases (e.g. trypsin-like serine protease), such as serine protease with an S1 pocket similar to that of chymotrypsin or of elastase. For example, to specifically bind to and/or inhibit chymotrypsin, the P1-like loop of a subject protease-binding agent (e.g., an antibody) would comprise amino acid(s) of hydrophobic side chains in order to bind to the hydrophobic S1 pocket of chymotrypsin. In view of the above, varying the amino acid(s) of the loop of a subject protease-binding agent that is capable of interacting with the S1 pocket of a specific protease determines whether the agent can bind/inhibit the protease but not a protease with a different S1 pocket.

Protease Specificity Feature

As noted above, a subject protease-binding agent may exhibit potent inhibitory activity against a protease while maintaining protease specificity. In addition to providing the specificity, one or more of the specificity features described below also function to position the inhibitory feature for binding to the protease in the desired orientation. For example, several surface loops on the heavy chain and/or light chains of a subject protease-binding agent can provide specific binding to the binding agent and in the same time, interact with the protease in such a way to place the P1-like loop of a hypervariable region in the desired orientation into the S1 pocket of a serine protease. Accordingly, many features may be engineered as part of a subject protease-binding agent in order to confer specificity while maintaining the inhibitory features described previously.

One way to confer specificity is to engineer one or more CDRs to bind to one or more of the Sn pockets similar to how a cleavable substrate would bind. A protease-binding agent may comprise structural features that mimic one or more Pn sites of a cleavable substrate. One or more structural features may present the same amino acid residues, or conservative substitutions thereof, as one or more of the Pn sites of a cleavable substrate. The specificity of a subject protease-binding agent for a protease would then be determined by the sequence of one or more CDRs in hypervariable regions. For example, a specific CDR of a subject protease-binding agent may present amino acid residues that can form favorable interactions with the Sn sites of one protease but not the same Sn site of a different protease. The specificity of a protease-binding agent for a protease may also be determined by the sequence of CDR that interacts with surface loops surrounding the active site. The surface loops contacted by a subject protease-binding agent may be proximal or distal to the active site. The surface loops contacted by a protease-binding agent may not be the same loops contacted by a respective cleavable substrate. Some of the favorable interaction between an antibody acting as a protease-binding agent and the protease include but not limited to hydrogen bonding, water-mediated bonding, and hydrophobic interactions.

Specificity Feature for Chymotrypsin-Fold Serine Protease

Where a subject protease-binding agent specifically binds to and inhibits a chymotrypsin-fold serine protease but not other serine proteases, the binding agent comprises structural features that would be specific for the structural framework shared by the family members of chymotrypsin-like serine protease. For example, a subject protease-binding agent can comprise hypervariable loops that are capable of binding to the framework shared by chymotrypsin-fold serine protease. The structural framework includes the signature structural fold of two β-barrels with the catalytic Ser, H is, and Asp amino acids in between. Hypervariable regions may be designed or screened for specific binding to that structural fold. A subject protease-binding agent may also contain CDRs that participate in P1 and P3 hydrogen bonding that is common among the chymotrypsin-fold serine proteases, describe previously.

In order to differentiate among chymotrypsin-fold serine proteases, the hypervariable loops in the heavy and light chains are further varied in accordance with sequence variation among the proteases of this family. As discussed previously, although having the same framework, many chymotrypsin-like serine proteases have divergent amino acid sequence away from the active site. As a result, one or more hypervariable loops may comprise different amino acid residues to complement the difference in amino acid sequences so to provide inhibitor specificity. Depending on the type of amino acid residues that are interacting with the protease beyond the active site, the antibody can bind to or inhibit one protease but not another. As noted above for inhibiting serine proteases in general, a protease-binding agent that inhibits chymotrypsin-fold serine protease would also comprise one or more CDRs that are capable of positioning a scissile bond in a reversed orientation in the active site of the chymotrypsine-fold serine protease.

Specificity Feature for Trypsin-Like Serine Protease

A subject protease-binding agent that is specific for the trypsin-like serine protease subfamily (chymotrypsin-fold serine protease that has the same S1 pocket as that of trypsin) would comprise many features discussed above. For example, a protease-binding agent can comprise one or more CDRs that make up a structural feature that is capable of binding to the conserved structural regions, such as the chymotrypsin fold discussed above. The specificity structures are also capable of interacting with the substrate binding cleft so as to position a scissile bond in a reversed orientation relative to that of a cleavable substrate complexed to the protease of interest. A protease-binding agent may comprise CDRs that are capable of fitting in a structural framework shared by this subfamily of trypsin-like serine protease. In the example of the H3 loop of A11 provided above, the inhibitory feature provided by the loop that is capable of binding to the S1 pocket of trypsin can also confer specificity. The loop in the hypervariable region of the antibody may be similar to the P1 site of a cleavable substrate, either in structural features or amino acid sequence. The loop may reside in the heavy chain or the light chain. Varying the sequence of this loop may provide specific binding to one protease but not to another with a different S1 pocket.

Specificity Feature for Type II Transmembrane Serine Protease

A subject protease-binding agent can specifically bind and inhibit a type II transmembrane serine protease (TTSP). For example, a subject protease-binding agent can comprise one or more CDRs that make up a structural feature that is capable of binding to the conserved structural regions in TTSPs, such as the transmembrane region, the stem region, or the proteolytic region. A protease-binding agent may comprise CDRs that are capable of fitting in a structural framework shared by this specific group of serine protease. Like the previous antibodies described above, the CDRs of the hypervariable regions may be changed to conform to a specific TTSP of interest. The CDRs may form surface loops that interact with segments of the TTSP surrounding the active site and beyond. In addition to the specificity features, a protease-binding agent can comprise a loop that is capable of binding to the S1 pocket similar to the S1 pocket of trypsin. This loop of such a protease-binding agent may be similar to the P1 site of their respective cleavable substrate. Like the binding agent described previously, the hypervariable loop is inserted into the S1 pocket such that the scissile bond is presented to the active site in a reversed orientation relative to a cleavable substrate.

Specificity Feature for Membrane-Type Serine Protease I

Where a subject protease-binding agent specifically binds to or inhibits an active MT-SP1, the protease-binding agent does not bind to MT-SP1 bound to its cognate inhibitor (e.g. hepatocyte growth factor activator inhibitor type I, HAI-1) but to an active, mature MT-SP1 not bound to HAI-1. The substrate binding groove of MT-SP1 described above has certain preferred residues identified for the substrate: Arg or Lys at P4, a non-basic residue at P3, Ser at P4, Arg at P1, and Ala at P1'. Based on this profile, a protease-binding agent may be similar to a substrate with respect to these preferred residues and so would be capable of binding to the substrate binding groove of MT-SP1. The preferred residues may be incorporated into hypervariable regions of an antibody engineered to interact with the substrate binding groove. For example, the antibody A11 has an Arg in the H3 loop, which acts like a P1-loop when A11 is bound to MT-SP-1. A11 also inhibits MTSP-1 with high specificity. See Example 9 for details on other loop interactions between A11 and MT-SP1.

Features of a protease-binding agent that are specific for MT-SP1 may also be incorporated into binding agents engineered to bind to or inhibit other proteases having similar substrate binding groove. Some of such serine proteases include protease-activated receptor 2 (PAR-2), the urokinase-type plasminogen activator (active or the inactive zyomogen form, pro-uPA), and the hepatocyte growth factor (active or the inactive form, HGF). PAR-2, pro-uPA, and HGF all have substrates with similar preferred residues at the corresponding locations as the substrates of MT-SP1. These proteases are also implicated in the process of invasive cancerous growth as MT-SP1. An exemplary sequence of a P1-like loop that would be specific for binding to S1 pockets of proteases containing a substrate binding cleft similar to that of MT-SP1 is GIAARRF (SEQ ID NO:9). Variants of protease-binding agent that is specific for MT-SP1 are contemplated herein so that with the same framework containing conserved motifs, protease-binding agents may be generated to specifically bind these different serine proteases that share similarities.

Amino Acid Sequences

A subject protease-binding agent comprises a first polypeptide region (e.g. P1-like loop) that binds the S1 pocket of a protease and inhibits catalytic activity; and at least a second polypeptide region that binds the protease at a site other than the S1 pocket of a protease and provides for binding specificity. The first and second polypeptide regions may or may not be contiguous. For example, the first polypeptide region and the second polypeptide region may be contained within a single polypeptide chain and are separated from one another by one or more amino acids. A protease-binding agent can comprise a first polypeptide region (e.g. P1-like loop) that binds the S1 pocket of a protease and inhibits catalytic activity; and at least one other polypeptide region (e.g., at least a second polypeptide region and a third polypeptide region) that bind the protease at a site other than the S1 pocket of a protease and provides for binding specificity. The first polypeptide region and the second polypeptide region may also be present as separate polypeptide chains.

In some embodiments, the protease-binding agent may be represented by $X_1$-A-$X_2$—B—$X_3$, in which A represents the first polypeptide region, B represents the second polypeptide region, and each of $X_1$, $X_2$, and $X_3$, if present, independently represents optional amino acid residue(s) or linker(s). The first polypeptide region and the second polypeptide region may be contained within a single polypeptide chain, separated from one another by one or more amino acids, as represented by $X_2$. The first polypeptide region and second polypeptide region may be present in the context of a scaffold provided by $X_1$, $X_2$, and $X_3$ where each of $X_1$, $X_2$, and $X_3$ is independently a polymeric form of amino acids, or a polymeric form of moieties other than amino acids (e.g., non-polypeptide polymers), where each of $X_1$, $X_2$, and $X_3$ comprises from 0 to about 100 monomers.

The first polypeptide region may have a length of from about 1 aa to about 100 aa, e.g., from about 7 aa to about 10 aa, from about 10 aa to about 15 aa, from about 15 aa to about 20 aa, from about 20 aa to about 25 aa, from about 25 aa to about 30 aa, from about 30 aa to about 50 aa, from about 50 aa to about 75 aa, or from about 75 aa to about 100 aa. The first polypeptide region comprises an RR (Arg-Arg) sequence. The first polypeptide region may comprise an amino acid sequence having at least about 85% or 100%, amino acid sequence identity to the amino acid sequence GIAARRF (SEQ ID NO:9). The first polypeptide region may comprise an amino acid sequence having at least about 80%, at least about 85%, at least about 90%, or 100% amino acid sequence identity to the amino acid sequence DLGIAARRFVSGAFDI (SEQ ID NO:10). The first polypeptide region may comprise an amino acid sequence having 100% amino acid sequence identity to the amino acid sequence PxRRGP, such as PQRRGP (SEQ ID NO: 11), in which x may be any amino acid sequence. The first polypeptide region may comprise an amino acid sequence having at least about 80%, at least about 85%, at least about 90%, at least about 94%, or 100% amino acid sequence identity to the amino acid sequence PYLTYPQRRGPQNVSPFDN (SEQ ID NO:12). Alternatively, these amino acid sequences may be modified such that one or both of the double arginines are substituted with methionines. For example, GIAARRF (SEQ ID NO:9) or PxRRGP and sequences that contain thereof may be modified to contain GIAARMF, GIAAMRF, GIAAMMF, PxRMGP, PxMRGP, or PxMMGP. Conservative amino acid substitutions may also be contemplated for these amino acid sequences.

Optional linkers of polypeptide region or within polypeptide features may comprise amino acid residues or non-peptide polymers. The linkers may have a length of from about 1 to about 100 monomers, e.g., from about 7 to about 10, from about 10 to about 15, from about 15 to about 20, from about 20 to about 25, from about 25 to about 30, from about 30 to about 50, from about 50 to about 75, or from about 75 to about 100 monomers.

As noted above, in some embodiments, one or more of $X_1$, $X_2$, and $X_3$ is a non-polypeptide polymer, e.g., a synthetic polymer. Exemplary synthetic polymers include, but are not limited to, polymers or copolymers derived from polydioxane, polyphosphazene, polysulphone resins, poly(acrylic acid), poly(acrylic acid)butyl ester, poly(ethylene glycol), poly(propylene), polyurethane resins, poly(methacrylic acid), poly(methacrylic acid)-methyl ester, poly(methacrylic acid)-n butyl ester, poly(methacrylic acid)-t butyl ester, polytetrafluoroethylene, polyperfluoropropylene, poly N-vinyl carbazole, poly(methyl isopropenyl ketone), poly alphamethyl styrene, polyvinylacetate, poly(oxymethylene), poly(ethylene-co-vinyl acetate), a polyurethane, a poly(vinyl alcohol), and polyethylene terephthalate; ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid) (PGA); poly (D,L-lactic acid) (PLA); copolymers of PGA and PLA; poly (glycolic acid-co-trimethylene carbonate); polyphosphoester; polyphosphoester urethane; poly(amino acids); cyanoacrylates; poly(trimethylene carbonate); poly (iminocarbonate); copoly(ether-esters) (e.g., PEO/PLA); polyalkylene oxalates; polyphosphazenes; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; and carboxymethyl cellulose.

The protease-binding agent of the present disclosure includes one or more parts of the agent to be cyclic. Methods of cyclizing a peptide are known in the art, and any of a variety of established methods can be used to cyclize a peptide. For example, a peptide can be synthesized to include a Cys at or near the amino terminus and a Cys at or near the carboxyl terminus, and a disulfide bond can be formed between the two Cys residues.

Where the subject protease-binding agent is an antibody, the subject antibody may comprises a light chain polypeptide having an amino acid sequence having at least about 90%, at least about 95%, at least about 98%, or at least about 99%, amino acid sequence identity to a contiguous stretch of the amino acid sequence set forth in SEQ ID NO: 1.

A subject protease-binding agent may comprise a light chain polypeptide having an amino acid sequence having at least about 85%, at least about 90%, at least about 95%, at least about 98%, or at least about 99%, amino acid sequence identity to a contiguous stretch of the amino acid sequence set forth in SEQ ID NO: 5.

A subject protease-binding agent may comprise a heavy chain polypeptide having an amino acid sequence having at least about 85%, at least about 90%, at least about 95%, at least about 98%, or at least about 99%, amino acid sequence identity to a contiguous stretch of the amino acid sequence set forth in SEQ ID NO: 3.

A subject protease-binding agent may comprise a heavy chain polypeptide having an amino acid sequence having at least about 80%, at least about 85%, at least about 90%, at least about 95%, at least about 98%, or at least about 99%, amino acid sequence identity to a contiguous stretch of the amino acid sequence set forth in SEQ ID NO:7.

For example, a subject protease-binding agent can include the same CDRs and framework regions (FRs) as the sequences depicted in FIG. 2. In another embodiment, a subject antibody has a light or a heavy chain polypeptide sequence as depicted in FIG. 2.

The CDRs and FRs of a subject antibody may be determined by methods routine in the art, as noted previously. In one example, the CDRs and FRs are determined based on the Kabat numbering system and are detailed as the following. For the A11 light chain, CDR1 has amino acid sequence of RASQSVSSSYLA (SEQ ID NO:16). CDR2 of the light chain has amino acid sequence of GASTRAT (SEQ ID NO: 17). CDR3 of the light chain has an amino acid sequence of QQRSNWPPGYT (SEQ ID NO: 18). For the A11 heavy chain, CDR1 has an amino acid sequence of GFTFSSYAMS (SEQ ID NO:19). CDR2 of the heavy chain has an amino acid sequence of AISGSGGSTY (SEQ ID NO:20). CDR3 of the heavy chain has an amino acid sequence of DLGIAAR-RFVSGAFDI (SEQ ID NO:10).

In another example, the CDRs of a subject antibody may be the same as one or more CDRs of E2 light chain and the amino acid sequences of the CDRs are as follows. CDR1 has amino acid sequences of RASQGISSYLA (SEQ ID NO: 21). CDR2 has amino acid sequences of AASSLQS (SEQ ID NO:22). CDR3 has an amino acid sequence of QQHGNLPYT (SEQ ID NO: 23). For the E2 heavy chain, CDR1 has amino acid sequences of GFTFSSYAMS (SEQ ID NO: 24). CDR2 of the light chain has amino acid sequences of AISGSGGSTY (SEQ ID NO:25). In the case of CDR3 of the light chain, the amino acid sequence is PYLTYPQRRGPQNVSPFDN (SEQ ID NO: 12). The CDRs of heavy and light chains of A11 and E2 antibodies are summarized in the table below.

TABLE 2

Complementarity determining regions of A11 and E2 according to the Kabat database.

| | A11 | E2 |
|---|---|---|
| Light Chain | | |
| CDR1 | RASQSVSSSYLA (SEQ ID NO: 16) | RASQGISSYLA (SEQ ID NO: 21) |

TABLE 2-continued

Complementarity determining regions of
A11 and E2 according to the Kabat database.

|  | A11 | E2 |
|---|---|---|
| CDR2 | GASTRAT<br>(SEQ ID NO: 17) | AASSLQS<br>(SEQ ID NO: 22) |
| CDR3 | QQRSNWPPGYT<br>(SEQ ID NO: 18) | QQHGNLPYT<br>(SEQ ID NO: 23) |
| Heavy Chain | | |
| CDR1 | GFTFSSYAMS<br>(SEQ ID NO: 19) | GFTFSSYAMS<br>(SEQ ID NO: 24) |
| CDR2 | AISGSGGSTY<br>(SEQ ID NO: 20) | AISGSGGSTY<br>(SEQ ID NO: 25) |
| CDR3 | DLGIAARRFVSGAFDI<br>(SEQ ID NO: 10); | PYLTYPQRRGPQNVSPFDN<br>(SEQ ID NO: 12) |

Examples of a protease-binding agent include those having a light chain polypeptide comprising one or more CDRs (CDR1, CDR2 or CDR3) of the variable region of an A11 light chain polypeptide described above and a heavy chain polypeptide comprising one or more CDRs (CDR1, CDR2, or CDR3) of the variable region of the A11 heavy chain polypeptide described above. One to five amino acid residues in one or more of the CDRs set forth above may be deleted, inserted, or substituted in the subject protease-binding agent. Conservative substitutions may also be present.

In certain embodiments, the heavy chain hypervariable region of a subject antibody excludes the following sequences: GFTFSSYAMS (SEQ ID NO:26), GVTGSSYAMS (SEQ ID NO:27), AISGSGGSTYYADS-VKG (SEQ ID NO:28), AISSSGVNTHYADSVKG (SEQ ID NO:29), AISSGGNTHYADSVKG (SEQ ID NO:30), IASIALRGYYFDY (SEQ ID NO:31), and IASIATRGY-FFNY (SEQ ID NO:32). In certain embodiments, the light chain hypervariable region of a subject antibody excludes the following sequences: RASQSVSSYLA (SEQ ID NO:33), RASQTFGSSYLA (SEQ ID NO:34), RASQIFSSNSLA (SEQ ID NO:35), GASSRAT (SEQ ID NO:36), and QQYGSSPWT (SEQ ID NO:37).

A subject antibody may be presented as a monoclonal antibody of various subclasses (e.g. IgG or IgM). The antibody may also be a humanized monoclonal antibody. Chimeric antibodies may also be provided, especially if the antibodies are to be used in preventive or therapeutic pharmaceutical preparations. Chimeric antibodies composed of human and non-human amino acid sequences may be formed from the mouse monoclonal antibody molecules to reduce their immunogenicity in humans by standard techniques known in the art. Antibodies of the present disclosure encompass fragments that are capable of exhibiting immunological binding properties of the parent antibody molecule. The fragments include, but are not limited to, Fab, Fab' and F(ab')$_2$, Fd, single-chain Fvs (scFv), single-chain immunoglobulins (e.g., wherein a heavy chain, or portion thereof, and light chain, or portion thereof, are fused), disulfide-linked Fvs (sdFv), diabodies, triabodies, tetrabodies, scFv minibodies, Fab minibodies, and dimeric scFv and any other fragments comprising a $V_L$ and a $V_H$ domain in a conformation such that a specific antigen binding region is formed. Antibody fragments, including single-chain antibodies, may comprise the variable region(s) alone or in combination with the entire or partial of the following: a heavy chain constant domain, or portion thereof, e.g., a CH1, CH2, CH3, transmembrane, and/or cytoplasmic domain, on the heavy chain, and a light chain constant domain, e.g., a $C_{kappa}$ or $C_{lambda}$ domain, or portion thereof on the light chain. Also included in the invention are any combinations of variable region(s) and CH1, CH2, CH3, $C_{kappa}$, $C_{lambda}$, transmembrane and cytoplasmic domains. One or more fragments of the antibody may also be provided as cyclized forms.

The present disclosure provides compositions comprising a subject protease-binding agent. A subject composition can comprise, in addition to a subject protease-binding agent, one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl]-methyl-3-aminopropanesulfonic acid (TAPS), etc.; a solubilizing agent; a detergent, e.g., a non-ionic detergent such as Tween-20, etc.; a protease inhibitor; glycerol; and the like.

The disclosure also provides agents (e.g. antibodies) that are modified by conjugation to a moiety that can provide for a desired characteristic (e.g., increase in serum half-life, anticancer activity, etc.). Such antibody conjugates are exemplified below.

The protease-binding agent, such as an antibody, may be detectably labeled, either directly or indirectly. Labels include radioisotopes (e.g., $^{125}$I; $^{35}$S; $^{111}$In; $^{99m}$Tc, and the like); enzymes whose products generate a signal (e.g., luciferase, (-galactosidase, horse radish peroxidase, alkaline phosphatase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins; and the like. Indirect labels include second antibodies specific for a subject antibody, wherein the second antibody is labeled as described above; and members of specific binding pairs, e.g., biotin-avidin, and the like.

Recombinant Antibody

A protease-binding agent may be recombinant. Where the protease-binding agent is an antibody, the antibody may contain a light or heavy chain that is encoded by a polynucleotide having a nucleotide sequence that is at least 80% identical to (e.g., at least 85%, at least 90%, at least 95%, at least 98%) to a contiguous sequence of an A11 light or heavy chain-encoding nucleic acid, SEQ ID NO:2 and NO:4, respectively, or that of an E2 light or heavy chain-encoding nucleic acid, SEQ ID NO:6 and NO:8, respectively. The percentage identity is based on the shorter of the sequences compared. Well known programs such as BLASTN (2.0.8) (Altschul et al. (1997) Nucl. Acids. Res. 25:3389-3402) using default parameters and no filter may be employed to make a sequence comparison.

Methods for producing recombinant antibodies are known in the art. For example, the nucleic acids encoding the antibody, or at least a CDR of a heavy chain polypeptide or at least a CDR of a light chain polypeptide, are introduced directly into a host cell, and the cell incubated under conditions sufficient to induce expression of the encoded antibody. The recombinant antibody may be glycosylated by the endogenous glycosylase in the host cells, unglycosylated, or may have an altered glycosylation pattern.

Where the antibody is recombinant, the antibody may be chimeric. Chimeric antibodies are immunoglobulin molecules comprising human and non-human portions. More specifically, the antigen combining region (or variable region) of a humanized chimeric antibody is derived from a non-human source (e.g. murine), and the constant region of the chimeric antibody (which confers biological effector function to the immunoglobulin) is derived from a human source. The chimeric antibody can have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431 and 4,975,369). An alternative approach is the generation of humanized antibodies by linking the CDR regions of non-human antibodies to human constant regions by recombinant DNA techniques. See Queen et al., *Proc. Natl. Acad. Sci. USA* 86: 10029-10033 (1989) and WO 90/07861.

The invention contemplates recombinant fusion antibody that is specific for a serine protease, in which the antibody is modified to include a heterologous protein, i.e., is linked to a polypeptide to that is not part of the A11 antibody. For example, an A11 heavy chain polypeptide or A11 light chain polypeptide may be joined to a reporter protein or to a protein having a desired anti-cancer effect. The reporter protein may be a fluorescent protein. The antibody may also be conjugated to a second antibody (or at least an antigen-binding portion thereof), e.g., an antibody that specifically binds an angiogenic or proliferative factor, such as an antibody that is directed against vascular enthothelial growth factor (VEGF), which is key mediator of angiogenesis, where the antibody targets the conjugate to specific cancer cells and the anti-VEGF antibody inactivates VEGF thus inhibiting angiogenesis. Methods for producing a fusion protein of interest when provided a nucleic acid sequence are well known in the art.

Humanized and Human Antibodies

A subject antibody includes humanized antibodies. Amino acids may be substituted in the framework regions of a parent non-human antibody to produce a modified antibody that is less immunogenic in a human than the parent non-human antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 1991, 28:489-498; Studnicka et al., Protein Engineering 1994, 7:805-814; Roguska. et al., 1994, PNAS 91:969-973), and chain shuffling (U.S. Pat. No. 5,565,332). Framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 1988, 332:323). Additional methods for humanizing antibodies contemplated for use in the present disclosure are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. The antibody may also be humanized according to the methods set forth in published U.S. published patent application nos. 20040086979 and 20050033031. In view of the above, a subject antibody may be humanized using methods that are well known in the art.

The protease-binding agent may also be a fully human antibody. Human antibodies are primarily composed of characteristically human polypeptide sequences. A subject human antibody can be produced by a wide variety of methods (see, e.g., Larrick et al., U.S. Pat. No. 5,001,065). Human antibodies can be produced initially in trioma cells (descended from three cells, two human and one mouse). Genes encoding the antibodies are then cloned and expressed in other cells, particularly non-human mammalian cells. The general approach for producing human antibodies by trioma technology has been described by Ostberg et al. *Hybridoma* 1983, 2: 361-367, Ostberg, U.S. Pat. No. 4,634,664, and Engelman et al., U.S. Pat. No. 4,634,666. Triomas have been found to produce antibody more stably than ordinary hybridomas made from human cells.

Accordingly, the present disclosure contemplates a DNA molecule comprising a nucleic acid sequence encoding an antibody that binds to a protease (e.g. a nucleic acid encoding A11). An example of nucleic acid sequence encoding a heavy chain of an antibody that binds to a protease includes SEQ ID NO:4 and NO:8. An example of nucleic acid sequence encoding a light chain of an antibody that binds to a serine protease includes SEQ ID NO:2 and NO:6. The invention further contemplates recombinant host cells containing an exogenous polynucleotide encoding at least a CDR of a heavy chain polypeptide or at least a CDR of a light chain polypeptide of the subject antibody.

Polyethylene Glycol (PEG)-Modified Antibodies

A subject antibody may comprise one or more poly(ethylene glycol) (PEG) moieties. Such antibodies are referred to as "PEGylated antibodies." Antibodies contemplated herein include PEGylated antibodies, e.g., PEGylated recombinant antibodies that bind specifically to a protease. Methods and reagents suitable for PEGylation of an antibody are well known in the art. In general, PEG suitable for conjugation to an antibody is generally soluble in water at room temperature, and has the general formula $R(O-CH_2-CH_2)_nO-R$, where R is hydrogen or a protective group such as an alkyl or an alkanol group, and where n is an integer from 1 to 1000. Where R is a protective group, it generally has from 1 to 8 carbons.

The PEG may have at least one hydroxyl group modified to generate a functional group that is reactive with an amino group, e.g., an epsilon amino group of a lysine residue, a free amino group at the N-terminus of a polypeptide, or any other amino group such as an amino group of asparagine, glutamine, arginine, or histidine.

PEG may also be derivatized so that it is reactive with free carboxyl groups in the antibody polypeptide. Suitable derivatives of PEG that are reactive with the free carboxyl group at the carboxyl-terminus of a heavy chain or light chain polypeptide include, but are not limited to PEG-amine, and hydrazine derivatives of PEG (e.g., PEG-NH—NH$_2$).

Additional derivatives of PEG comprises a terminal thiocarboxylic acid group, —COSH, which selectively reacts with amino groups to generate amide derivatives. In other embodiments, the PEG comprises a reactive ester such as an N-hydroxy succinimidate at the end of the PEG chain. Such an N-hydroxysuccinimidate-containing PEG molecule reacts with select amino groups at particular pH conditions such as neutral 6.5-7.5.

The PEG can be conjugated directly to an amino acid residue of the antibody, or through a linker. In some embodiments, a linker is added to an antibody polypeptide, forming a linker-modified antibody polypeptide. Such linkers provide various functionalities, e.g., reactive groups such sulfhydryl, amino, or carboxyl groups to couple a PEG reagent to the linker-modified antibody polypeptide.

The PEG may be conjugated to the antibody polypeptide is linear. In other embodiments, the PEG conjugated to the antibody polypeptide is branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

Conjugates

The subject antibody may be conjugated to a second (non-antibody) molecule. An antibody conjugated to a second molecule is referred to as an "antibody conjugate." A subject antibody conjugate may be useful for modifying the growth of cells, particularly bacterial and cancer cells. The compositions encompasse aggregates of conjugates, as they are readily taken up by cells.

A subject antibody conjugate retains the desired activity, while exploiting properties of the second molecule of the conjugate to impart an additional desired characteristic. For example, a subject antibody can be conjugated to a second molecule that aids in solubility, storage or other handling properties, cell permeability, half-life, controls release and/or distribution such as by targeting a particular cell (e.g., neurons, leucocytes etc.) or cellular location (e.g., lysosome, endosome, mitochondria etc.), tissue or other bodily location (e.g., blood, neural tissue, particular organs etc.). Other examples include the conjugation of a dye, fluorophore or other detectable labels or reporter molecules for assays, tracking and the like. More specifically, a subject antibody can be conjugated to a second molecule such as a peptide, polypeptide, dye, fluorophore, nucleic acid, carbohydrate, lipid and the like (e.g., at either the reducing or non-reducing end), such as the attachment of a lipid moiety, including N-fatty acyl groups such as N-lauroyl, N-oleoyl, fatty amines such as dodecyl amine, oleoyl amine, and the like (e.g., see U.S. Pat. No. 6,638,513)).

The present disclosure further provides an antibody conjugate that comprises a moiety that modifies cellular uptake relative to unconjugated material. The antibody conjugate may exhibit increased cellular uptake relative to unconjugated material. In alternative embodiments, the conjugate exhibits decreased cellular uptake relative to unconjugated material. In this aspect, the efficiency of cellular uptake can be increased or decreased by linking to peptides or proteins that facilitate endocytosis. For example, a given antibody can be linked to a ligand for a target receptor or large molecule that is more easily engulfed by endocytotic mechanisms, such as another antibody. The antibody or other ligand can then be internalized by endocytosis and the payload released by acid hydrolysis or enzymatic activity when the endocytotic vesicle fuses with lysosomes. As such, the conjugate may be one that increases endocytosis relative to unconjugated antibody. To decrease cellular uptake, the conjugate can include a ligand that retains the antibody on the surface of a cell, which can be useful as a control for cellular uptake, or in some instances decrease uptake in one cell type while increasing it in others.

Other features of a conjugated antibody may include one where the conjugate reduces toxicity relative to unconjugated antibody. Another feature is that the conjugate may target a cancer cell more efficiently than an unconjugated material. Additional examples include an antibody of the present disclosure conjugated with one or more molecules that complement, potentiate, enhance or can otherwise operate synergistically in connection with the antibody of the present disclosure. For instance, the antibody can optionally have attached an anti-cancer drug for delivery to a site of a cancer or bacterial cell to further facilitate cell killing or clearance, e.g., an anti-proliferation moiety (e.g., VEGF antagonist, e.g., an anti-VEGF antibody), a toxin (e.g., an anti-cancer toxin, e.g., ricin, *Pseudomonas* exotoxin A, and the like), radionuclide (e.g. 90Y, 131I, 177L, 10B for boron neutron capture, and the like), anti-cancer drugs (e.g. doxorubicin, calicheamicin, maytansinoid DM1, auristatin caupecitabine, 5-fluorouricil, leucovorin, irinotercan, and the like), and/or can optionally be modified to provide for improved pharmacokinetic profile (e.g., by PEGylation, hyperglycosylation, and the like).

Pharmaceutical Compositions

Also provided herein are pharmaceutical compositions containing a subject protease-binding agent (e.g., a subject antibody). A subject pharmaceutical composition can be provided in a pharmaceutically acceptable excipient, which can be a solution such as an aqueous solution, often a saline solution or they can be provided in powder form. A subject composition may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

A subject protease-binding agent, e.g., in the form of a pharmaceutically acceptable salt, can be formulated for oral, topical or parenteral administration for use in the methods, as described above. In certain embodiments, e.g., where an antibody is administered as a liquid injectable (such as in those embodiments where they are administered intravenously or directly into a tissue), an antibody formulation is provided as a ready-to-use dosage form, or as a reconstitutable storage-stable powder or liquid composed of pharmaceutically acceptable carriers and excipients.

The concentration of a protease-binding agent in the pharmaceutical formulations can vary from less than about 0.1%, usually at or at least about 2% to as much as 20% to 50% or more by weight, and will be selected primarily by fluid volumes, viscosities, etc., in accordance with the particular mode of administration selected and the patient's needs. The resulting compositions may be in the form of a solution, suspension, tablet, pill, capsule, powder, gel, cream, lotion, ointment, aerosol or the like.

Compositions of the present disclosure can include a therapeutically effective amount of a subject protease-binding agent, as well as any other compatible components, as needed. By "therapeutically effective amount" is meant that the administration of that amount to an individual, either in a single dose, as part of a series of the same or different antibody or compositions, is effective to inhibit the growth of a cancerous cell or a bacterial/viral infection in a subject. Such therapeutically effective amount of a protease-binding agent and its impact on cell growth or bacterial infection includes cooperative and/or synergistic inhibition of cell growth in conjunction with one or more other therapies (e.g., immunotherapy, chemotherapy, radiation therapy etc.) As noted below, the therapeutically effective amount can be adjusted in connection with dosing regimen and diagnostic analysis of the subject's condition (e.g., monitoring for the present or absence of a cell surface epitopes using an antibody specific for a serine protease) and the like.

The amount of composition administered to an animal, e.g., a human, in the context of the present disclosure should be sufficient to effect a prophylactic or therapeutic response in the animal over a reasonable time frame, and varies depending upon the goal of the administration, the health and physical condition of the individual to be treated, age, the taxonomic group of individual to be treated (e.g., human, non-human primate, primate, etc.), the degree of resolution desired, the formulation of the antibody composition, the treating clinician's assessment of the medical situation, and other relevant factors. One skilled in the art will also recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Thus it is expected that the amount will fall in a relatively broad range, but can nevertheless be routinely determined through various features of the subject such as note above.

Also, suitable doses and dosage regimens can be determined by comparisons to anticancer or immunosuppressive agents that are known to affect the desired growth inhibitory or immunosuppressive response. Such dosages include dosages which result in the low dose inhibition of cell growth, without significant side effects. In proper doses and with suitable administration of certain compounds, the compounds of the present disclosure can provide for a wide range of intracellular effects, e.g., from partial inhibition to essentially complete inhibition of cell growth. Dosage treatment may be a single dose schedule or a multiple dose schedule (e.g., including ramp and maintenance doses). As indicated below, a subject composition may be administered in conjunction with other agents, and thus doses and regiments can vary in this context as well to suit the needs of the subject.

Any of a wide variety of cancer therapies can be combined in a composition with a subject protease-binding agent. For example, agents used in chemotherapeutic treatment or biological response modifier treatment may be present in the pharmaceutical composition comprising the antibody. Certain agents are discussed in more detail below.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (CYTOXAN™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (TAXOL®), docetaxel (TAXOTERE®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (TAXOL®), TAXOL® derivatives, docetaxel (TAXOTERE®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and ZOLADEX®. Estrogens stimulate proliferation and differentiation; therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); IRESSA® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., TAXOTERE™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Antibody which finds use in the present disclosure is not limited to those with appropriate specificity and antigenicity in order to affect growth of a cancer or bacterial cell. As such, antibody with such specificity aid in achieving the intended end result of modifying cellular proliferation of a cancer cell or a bacterial cell while minimizing unwanted side effects and toxicity in accordance with the methods. Put differently, the antibody employed need not be identical to those disclosed in the Examples section below, so long as the antibody is able to elicit a response against and/or inhibit growth of a cancerous cell or a bacterial cell. Thus, one of skill will recognize that a number of antibody derivatives, can be made without substantially affecting the activity of the antibody. This includes compositions of pharmaceutically acceptable salts (e.g., hydrochloride, sulfate salts), solvates (e.g., mixed ionic salts, water, organics), hydrates (e.g., water).

Methods of Production

As discussed above, the present disclosure provides binding agents (e.g., antibodies) that bind to a protease (e.g. trypsin-like serine protease). A subject protease-binding agent is highly specific for binding and inhibiting a specific protease. Exemplary methods of making a subject protease-binding agent are presented below.

Antibodies can be prepared using a wide variety of techniques known in the art including the use of hybridoma, recombinant, and phage display technologies, or a combination thereof. For example, antibody may be made and isolated using methods of phage display. The antibody may also be isolated from sera of an animal host immunized with an immunogenic composition comprising a serine protease protein, which encompasses whole proteins and fragments thereof. Exemplary antibodies include an isolated antibody capable of binding to an S1 pocket of trypsin-like serine protease (e.g. A11).

The antigen that coats the wells for phage display panning or the immunogenic composition used to elicit the antibody of the present disclosure may comprise an aggregate of one or more antigens. The method may involve exposing antigens to an aggregating condition so as to form an aggregate. Thus the methods of production described above may further include a step of forming an aggregate of the isolated antigens. Examples of the aggregating conditions include heating, addition of an excipient that facilitates aggregation, and the like.

Antigens used to coat the wells for phage panning or to elicit antibodies of the present disclosure may be conjugated to another molecule. For example, the antigen can be conjugated to a second molecule such as a peptide, polypeptide, lipid, carbohydrate and the like that aids in solubility, storage or other handling properties, cell permeability, half-life, controls release and/or distribution such as by targeting a particular cell (e.g., neurons, leucocytes etc.) or cellular location (e.g., lysosome, endosome, mitochondria etc.), tissue or other bodily location (e.g., blood, neural tissue, particular organs etc.).

A particular embodiment of an antigen conjugated to a second molecule is where the second molecule is an immunomodulator. "Immunomodulator" is a molecule that directly or indirectly modifies an immune response. A specific class of immunomodulators includes those that stimulate or aid in the stimulation of an immunological response. Examples include antigens and antigen carriers such as a toxin or derivative thereof, including tetanus toxoid.

Phage Display

Phage display is used for the high-throughput screening of protein interactions. Phages may be utilized to display antigen-binding domains expressed from a repertoire or combinatorial antibody library (e.g., human or murine). Phage expressing an antigen binding domain that binds the protease of interest can be selected or identified with the protease of interest, e.g., using labeled serine protease or serine protease bound or captured to a solid surface or bead. Phage used in these methods are typically filamentous phage including fd and M13 binding domains expressed from phage with Fab, Fv (individual Fv region from light or heavy chains) or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, *Immunol. Today* 2000, 21:371; Nagy et al. Nat. Med. 2002, 8:801; Huie et al., *Proc. Natl. Acad. Sci. USA* 2001, 98:2682; Lui et al., *J. Mol. Biol.* 2002, 315:1063, each of which is incorporated herein by reference. Several publications (e.g., Marks et al., *Bio/Technology* 1992, 10:779-783) have described the production of high affinity human antibodies by chain shuffling, as well as combinatorial infection and in vivo recombination as a strategy for constructing large phage libraries. In another embodiment, ribosomal display can be used to replace bacteriophage as the display platform (see, e.g., Hanes et al., *Nat. Biotechnol.* 2000, 18:1287; Wilson et al., *Proc. Natl. Acad. Sci. USA* 2001, 98:3750; or Irving et al., *J. Immunol. Methods* 2001, 248:31). Cell surface libraries may be screened for antibodies (Boder et al., *Proc. Natl. Acad. Sci. USA* 2000, 97:10701; Daugherty et al., *J. Immunol. Methods* 2000, 243:211). Such procedures provide alternatives to traditional hybridoma techniques for the isolation and subsequent cloning of monoclonal antibodies. See methods and materials in Example section below.

In phage display methods, functional antibody domains are displayed on the surface of phage particles which carry the polynucleotide sequences encoding them. For example, DNA sequences encoding heavy chain variable (VH) and light chain variable (VL) regions are amplified or otherwise isolated from animal cDNA libraries (e.g., human or murine cDNA libraries of lymphoid tissues) or synthetic cDNA libraries. The DNA encoding the VH and VL regions may be joined together by an scFv linker by PCR and cloned into a phagemid vector (e.g., p CANTAB 6 or pComb 3 HSS). The vector is electroporated in *E. coli* and the *E. coli* is infected with helper phage. The VH or VL regions are usually recombinantly fused to either the phage gene III or gene VIII. Phage expressing an antigen binding domain that binds to an antigen of interest (i.e., a serine protease) can be selected or identified with antigen, e.g., using labeled antigen or antigen bound or captured to a solid surface or bead.

Additional examples of phage display methods that can be used to make the antibodies include those disclosed in PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the references listed above, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')$_2$ fragments can also be employed using methods known in the art such as those disclosed in PCT publication WO 92/22324; Mullinax et al., *BioTechniques* 1992, 12:864-869; and Sawai et al., *AJRI* 1995, 34:26-34; and Better et al., *Science* 1988, 240:1041-1043 (said references incorporated by reference in their entireties).

Immunization and Antibody Production

The method of eliciting antibodies in a host animal involves administering an effective amount of serine protease as antigens described above to the host animal (i.e., a suitable mammal such as a mouse, rabbit or guinea pig, or a suitable avian, such as a chicken) to elicit production of an antibody that specifically binds and inhibit a serine protease. Methods of immunizing animal, including the adjuvants used, booster schedules, sites of injection, suitable animals, etc. are well understood in the art, e.g., Harlow et al. (*Antibodies: A Laboratory Manual*, First Edition (1988) Cold spring Harbor, N.Y.), and administration of living cells to animals has been described for several mammals and birds, e.g., McKenzie et al (*Oncogene* 4:543-8, 1989), Scuderi et al (*Med. Oncol. Tumor Pharmacother* 2:233-42, 1985), Roth et al (Surgery 96:264-72, 1984) and Drebin et al (*Nature* 312:545-8, 1984). Next, a population of antibody producing cells is generated. In one embodiment, the population of cells is produced using hybridoma methods that well known to one of skill in the art (see, e.g., Harlow *Antibodies: A Laboratory Manual*, First Edition (1988) Cold Spring Harbor, N.Y.). Cells are fused to immortalized cells, such as myeloma cells or transformed cells, which are capable of replicating indefinitely in cell culture, thereby producing an immortal, immunoglobulin-secreting cell line. The immortal cell line utilized can be selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT). In alternative embodiments, populations of cells expressing monoclonal antibodies may be made using phage display methods.

Anti-protease antibodies, including antigen binding fragments of anti-protease antibodies, may also be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library can be constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell). When antibody gene synthesis is induced in the transfected host, the heavy and light chain proteins self-assemble to produce active antibodies that can be detected by screening with the antigen or immunogen.

Phage Panning and Screening

Once the population of antibody-producing cells or phages is produced, the antibodies are screened using one or a combination of a variety of assays. In general, these assays are functional assays, and may be grouped as follows: assays that detect an antibody's binding affinity or specificity, and assays that detect the ability of an antibody to initialize or inhibit a process.

For example, the antigen is coupled to beads or wells or other solid support and incubated with phage displaying the antibody of interest. After washings, bound phage is then recovered by inoculation of log phase *E. coli* cells. The cells are grown and expanded with helper phage. Steps are repeated for the amplification of tightly bound phages. The phage-infected *E. coli* colonies after several round of enrichment are harvested and Fab antibodies are purified from the periplasmic fractions. The purified antibodies are then analyzed in accordance with methods known in the art. Certain exemplary examples are detailed below.

The population of antibody isolated from phage-infected cells or hybridomas is further analyzed and/or screened for binding to a single antigen (i.e., antigens that are not mixed with other antigens of the plurality of antigens) of the plurality of antigens in vitro or in situ (e.g. on cells). Immunospecific binding may be carried out according to methods routine and known in the art. The immunoassays which can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. See, e.g., Ausubel et al, eds, 1994, Current Protocols in Molecular Biology, Vol. 1, John Wiley & Sons, Inc., New York, which is incorporated by reference herein in its entirety.

In addition to binding assays, the cells and antibodies may be screened based on the ability of the antibody in the supernatant to perform a specific function (e.g., activate complement deposition on cells).

Antibodies of the present disclosure may also be screened in vivo. The method involves administering a subject antibody to an animal model for a disease or condition and determining the effect of the antibody on the disease or condition of the model animal. In vivo assays of the invention include controls, where suitable controls include a sample in the absence of the antibody. Generally, a plurality of assay mixtures is run in parallel with different antibody concentrations to obtain a differential response to the various concentrations. Typically, one of these concentrations serves as a negative control, i.e., at zero concentration or below the level of detection.

A monoclonal antibody of interest is one that modulates, i.e., reduces or increases a symptom of the animal model disease or condition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the antibody. In general, a monoclonal antibody of interest will cause a subject animal to be more similar to an equivalent animal that is not suffering from the disease or condition. Antibodies that have therapeutic value that have been identified using the methods and compositions of the invention are termed "therapeutic" antibodies.

Selected monoclonal antibodies of interest can be expanded in vitro, using routine tissue culture methods, or in vivo, using mammalian subjects. For example, pristane-primed mice can be inoculated with log phase hybridoma cells in PBS for ascites production. Ascites fluid can be stored at −70° C. prior to further purification.

Production of Isolated Antibodies

Once obtained, the antibody can be isolated and, where desired, purified, for use in the assays and therapies disclosed herein. Examples of techniques which can be used to produce single-chain Fvs and antibodies include those described in U.S. Pat. Nos. 4,946,778 and 5,258,498; Huston et al., *Methods in Enzymology* 1991, 203:46-88; and Skerra et al., *Science* 1988, 240:1038-1040 (1988). Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 1991, 28:489-498; Studnicka et al., *Protein Engineering* 1994, 7:805-814; Roguska. et al., *PNAS* 1994, 91:969-973), and chain shuffling (U.S. Pat. No. 5,565,332). Isolation and purification of antibodies can be accomplished using these and other techniques known in the art, and can provide for antibody-containing preparations at least 50% to 60%, by weight, free from organic molecules with which the antibody is naturally associated or with which it is associated during manufacture. Antibody preparations include those that contain antibody in an amount of at least 75%, more usually at least 90%, and generally at least 99%, by weight. See methods and material in Example section below.

According to the methods described above, in one embodiment, the isolated antibody of the present disclosure is produced by a phage display method where MT-SP1 is the antigen used in phage panning. Given the know amino acid sequence, nucleic acid coding sequence may be inferred. The antibody may then be produced using recombinant methods in a bacteria or mammalian tissue culture directed toward high level of protein production. See Example 2 for detail.

Nucleic Acid Encoding the Antibody

Cell expressing a monoclonal antibody of interest contains the immunoglobulin heavy and light chain-encoding expression cassettes. As such, the nucleic acids encoding the monoclonal antibody of interest may be identified. Accordingly, the subject nucleic acids may be identified by a variety of methods known to one of skill in the art. Similar methods are used to identify host cell cultures in monoclonal antibody production using hybridoma technology (Harlow et al., *Antibodies: A Laboratory Manual*, First Edition (1988) Cold spring Harbor, N.Y.), and rely on an "addressable" host cell and an "addressable" monoclonal antibody, such that once a monoclonal antibody of interest is identified, a host cell address may be determined and the nucleic acid encoding the antibody of interested isolated from the cell.

The nucleic acids encoding a monoclonal antibody of interest may be recovered, characterized and manipulated from a cell expressing the antibody using techniques familiar to one of skill in the art (Ausubel, et al, Short Protocols in Molecular Biology, 3rd ed., Wiley & Sons, (1995) and Sambrook, et al, Molecular Cloning: A Laboratory Manual, Third Edition, (2001) Cold Spring Harbor, N.Y.).

For example, a monoclonal antibody produced in the method described above has a CDR polypeptide sequence selected from a CDR polypeptide sequence depicted in FIG. 2. In another embodiment, the monoclonal antibody has a light and heavy chain complementarity determining region (CDR) polypeptide sequence as depicted in FIG. 2.

Methods of Screening

A screening method provided by the present disclosure may involve the use of a phage library to screen for a protease-binding agent. The binding agent may be selected for its potent inhibition of a protease of interest and/or its specific binding affinity. The method may be executed according to the phage display method described above.

Briefly, the protease of interest (e.g. a P1-Arg-specific protease) may be immobilized on an ELISA plate or on beads through a covalent or non-covalent interaction, such as hydrophobic adsorption, biotin-avidin interaction, and $Ni^{2+}$-6×His interaction. The phage library is then incubated with the immobilized antigen/protease, washed, and recovered. During panning and selection, the bound phage is recovered and amplified in *E. coli*. Multiple successive selection rounds ensure a selection of a phage displaying a polypeptide that acts as a binding agent or inhibiting agent specific for the protease of interest. The stringency of the washes increases over a number of rounds (e.g. three). Many techniques well known in the art may be employed to increase the specificity of the recovered phage. Examples include increased wash times, increased detergent concentrations, increased salt concentrations, and inclusion of known macromolecular inhibitors (e.g. BPTI, Ecotin, and/or previously identified antibody inhibitors). Identification of inhibitory antibodies may include ELISAs and inhibition assays. Details on the assays to be performed in the method for selecting and isolating a polypeptide that can act as a protease-binding agent are discussed above.

Proteases of interest that may be used to screen for potential protease-binding agent include the protease targets described previously. Exemplary proteases include but not limited to chymotrypsin-fold serine proteases or P1-Arg-specific proteases (e.g. Kallikrein-2, Kallikrein-6, HGFA, transmembrane protein serine 2 (TMPRSS2), urokinase-type plasminogen activator (uPA), tissue kinase plasminogen activator (tPA), etc.).

A population candidate protease binding agents that are used in the screening methods may be engineered so that each contains the inhibitor and specificity features described above. For example, certain parts of the protease binding agent may be held constant (e.g. P1-like loop, CDR3 of the heavychain hypervariable region) while others may be randomized (specificity features) for specificity. The P1-like loop found in the heavy chain hypervariable region may also be maintained or modified according to the type of protease for which the candidate agent is designed.

Also contemplated by the present disclosure is a library of nucleic acid constructs encoding the candidate protease binding agents described herein. The library encodes a plurality of candidate protease binding agents that may have one or more polypeptide regions in common (e.g. a heavy chain CDR3) and at least one other polypeptide region that varies among the population. One variation may be the length of the hypervariable loop for a desired orientation to allow for surface loop contacts. The length of the loop may be varied by no more than 5, 3, 2, or 1 residue relative to the P1-like loop of the A11 antibody. The length may be changed by adding or deleting amino acid residues starting at the N-terminus, C-terminus or at both terminus of the loop. The candidate binding agents may be engineered to have a hypervariable loop comprising one of the amino acid sequences discussed above for the P1-like loop that is inserted into the S1-pocket of a protease when complexed with the protease, such as GIAARRF (SEQ ID NO: 9), DLGIAARRFVSGAFDI (SEQ ID NO: 10), PQRRGP (SEQ ID NO: 11), PxRRGP, in which x stands for any amino acid residue, or PYLTYPQRRGPQNVSPFDN (SEQ ID NO: 12). Candidates containing these exemplary hypervariable regions may be encoded by the library of nucleic acid constructs. These amino acid sequences encoded by the nucleic acids may be modified such that the double arginines are substituted with double methionines. The amino acid sequences listed here can also contain conservative amino acid substitutions for one or more of the amino acid residues.

Diagnostics Methods

The present disclosure provides a method of detecting a protease in a biological sample in situ or isolated from a subject. The methods are useful to both diagnostic and prognostic purposes. A subject method generally involves contacting a sample comprising a cell with a subject protease binding agent; and detecting binding of a subject protease-binding agent to a cell in the sample. The cell can be in vitro, where the cell is in a biological sample obtained from a subject suspected for having cancer cells, a subject suspected of having cells infected with a pathogen, a subject undergoing treatment, or a subject being tested for susceptibility to treatment. The cell can be in vivo, e.g., the cell is in a subject suspected for having cancer cells, a subject suspected of having cells infected with a pathogen, a subject undergoing treatment, or a subject being tested for susceptibility to treatment.

Antibodies reactive with a specific protease (e.g. a serine protease) can be used to detect the protease in a biological sample of a subject having or suspected of having cancerous cells or pathogens using anti-protease antibodies in immunodiagnostic techniques. The present disclosure provides additional antibodies suitable for the purpose of detection of cancer cells given their ability to recognize and bind an active protease commonly found on both cancer cells (e.g. active MT-SP1). Such diagnostics can be useful to identify patients amenable to the therapies disclosed herein, and/or to monitor response to therapy. Further, such antibodies can have or be selected to have antigen-binding properties such that the antibodies exhibit little or no detectable binding to non-active serine proteases or different types of serine proteases, thereby providing for decreased risk of false positive results.

Suitable immunodiagnostic techniques include, but are not necessarily limited to, both in vitro and in vivo (imaging) methods. The phrase "in vivo imaging" as used herein refers to methods of detecting the presence of a protein (e.g. detectably labeled A11) in whole, live mammal. Optically detectable proteins such as fluorescent antibodies and luciferases-conjugated antibodies may be detected by in vivo imaging. Methods for using luciferases for real-time imaging of luciferase expression in live animals can be readily adapted for use in the subject methods disclosed herein (e.g., Greer L F et al., *Luminescence* 2002, 17: 43-74). In vivo imaging of fluorescent proteins in live animals is described in, e.g., Hoffman, *Cell Death and Differentiation* 2002, 9:786-789. See Example 13 for details. In vivo imaging may be used to provide 2-D as well as 3-D images of a mammal. Radiolabeled antibodies, for example, may be administered to a subject and the subject imaged with a gamma camera. Charge-coupled device cameras, CMOS, or 3D tomographers may used to carry out in vivo imaging. For example, Burdette J E *Journal of Mol. Endocrin.*, 40: 253-261, 2008, reviews utilizing computed tomography, magnetic resonance imaging, ultrasonography, positron emission tomography, single-photon emission computed tomography (SPECT), etc., for in vivo imaging. SPECT can also be used with an integrated x-ray CAT (CT) scanner (SPECT/CT) in the subject methods. The information from many in vivo imaging methods as those described above can provide 3D distribution of the antibodies in the subject. See Example 16 for more detail.

Where the methods are in vitro, the biological sample can be any sample in which an active protease may be present, including but not limited to, blood samples (including whole blood, serum, etc.), tissues, whole cells (e.g., intact cells), and tissue or cell extracts. For example, the assay can involve detection of a protease on cells in a histological tissue sample. For example, the tissue sample may be fixed (e.g., by formalin treatment) and may be provided embedded in a support (e.g., in paraffin) or frozen unfixed tissue.

Assays can take a wide variety of forms, such as competition, direct reaction, or sandwich type assays. Exemplary assays include Western blots; agglutination tests; enzyme-labeled and mediated immunoassays, such as enzyme-linked immunosorbent assays (ELISAs); biotin/avidin type assays; radioimmunoassays; immunoelectrophoresis; immunoprecipitation, and the like. The reactions generally include detectable labels such as fluorescent, chemiluminescent, radioactive, enzymatic labels or dye molecules, or other methods for detecting the formation of a complex between antigen in the sample and the antibody or antibodies reacted therewith.

The assays can involve separation of unbound antibody in a liquid phase from a solid phase support to which antigen-antibody complexes are bound. Solid supports which can be used include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Where a solid support is used, the solid support is usually first reacted with a solid phase component (e.g., an anti-serine protease antibody) under suitable binding conditions such that the component is sufficiently immobilized to the support. Sometimes, immobilization to the support can be enhanced by first coupling the antibody to a protein with better binding properties, or that provides for immobilization of the antibody on the support with out significant loss of antibody binding activity or specificity. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind antibodies to a support include polysaccharides, polylactic acids, polyglycolic acids, polymeric amino acids, amino acid copolymers, and the like, with the proviso that the molecule used to immobilize the antibody does not adversely impact the ability of the antibody to specifically bind antigen. Such molecules and methods of coupling these molecules to the antibodies, are well known to those of ordinary skill in the art. See, e.g., Brinkley, M. A. Bioconjugate Chem. (1992) 3:2-13; Hashida et al., J. Appl. Biochem. (1984) 6:56-63; and Anjaneyulu and Staros, International J. of Peptide and Protein Res. (1987) 30:117-124.

After reacting the solid support with the solid phase component, any non-immobilized solid-phase components are removed from the support by washing, and the support-bound component is then contacted with a biological sample suspected of containing a serin protease under suitable binding conditions. After washing to remove any non-bound ligand, a secondary binder moiety is added under suitable binding conditions, wherein the secondary binder is capable of associating selectively with the bound ligand. The presence or absence of the secondary binder can then be detected using techniques well known in the art.

An ELISA method can be used, wherein the wells of a microtiter plate are coated with a subject anti-protease antibody. A biological sample containing or suspected of containing a protease (e.g., a tumor cell expressing active MT-SP1), is then added to the coated wells. After a period of incubation sufficient to allow antibody binding, the plate(s) can be washed to remove unbound moieties and a detectably labeled secondary binding molecule added. The secondary binding molecule is allowed to react with any captured antigen, the plate washed and the presence or absence of the secondary binding molecule detected using methods well known in the art.

Where desired, the presence or absence of bound serine protease from a biological sample can be readily detected using a secondary binder comprising an antibody directed against the antibody ligands. For example, a number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antibodies and serine protease form complexes under precipitating conditions. For example, the antibody can be attached to a solid phase particle (e.g., an agarose bead or the like) using coupling techniques known in the art, such as by direct chemical or indirect coupling. The antibody-coated particle is then contacted under suitable binding conditions with a biological sample suspected of containing a serine protease to provide for formation of particle-antibody-serine protease complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

The test sample used in the diagnostics assays can be any sample in which a serine protease may be present, including but not limited to, blood samples (including whole blood, serum, etc.), tissues, whole cells (e.g., intact cells), and tissue or cell extracts containing cells (e.g., tissue, isolated cells, etc.), a cell lysate (i.e., a sample containing non-intact cells), where each type of sample can contain elements of both types (e.g., a sample of cells can contain cell lysates, and vice versa). In some embodiments, particularly as in embodiments involving detection of cancer cells, it may be desirable to conduct the assay using a sample from the subject to be diagnosed that contains intact, living cells. Serine protease detection can then be assessed on an extracellular surface of the cells, and can further be assessed during cell division.

Diagnostic assays can also be conducted in situ. For example, anti-serine protease antibodies can be detectably labeled, administered to a subject suspected of having a cancer characterized by cell surface expression of a serine protease, and bound detectably labeled antibody detected using imaging methods available in the art.

The diagnostic assays described herein can be used to determine whether a subject has a cancer that is more or less amenable to therapy using antibody-based therapy, as well as monitor the progress of treatment in a subject. It also may be used to assess the course of other combination therapies (e.g., anti-serine protease antibody therapy as described in (U.S. Ser. No. 11/645,255 and PCT Application No. US2006/048850; incorporated herein by reference). Thus, the diagnostic assays can inform selection of therapy and treatment regimen by a clinician.

The protease of interest can be detected by detection of specific binding of an antibody, e.g., a monoclonal antibody (mAb) that has the antigen-binding specificity of A11 or E2. In this embodiment, the A11-reactive antigen or E2-reactive antigen may be present on the cell surface at any stage of the cell cycle, including during cell division. Of note is that in some instances, cancers that present the antigen during cell division may present a lower or no detectable level of the antigen when the cell is quiescent (i.e., not undergoing cell division). The antigen can also be detected in a permeabilized test cell. For example, a test cancer cell that exhibits a pattern of staining with an A11 antibody (or an antibody having the antigen binding specificity of A11) that is distinct from a pattern of antibody staining in a normal cell is identified as a cancerous cell that exhibits an A11-reactive antigen. Such cancers are thus amenable to therapy with an antibody that specifically binds the A11-reactive antigen (e.g., the mAb A11).

The above-described assay reagents, including the antibodies generated by immunization with a serine protease according to the methods described previously, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Therapeutic Methods

A subject protease-binding agent finds therapeutic use in a variety of diseases. For example, a subject protease-binding agent may be used in therapies for cancer or for pathogen infections (including prevention (e.g., vaccine) and post-diagnosis therapy) or diagnostics for cancers/infectious pathogen having a protease. Subjects having, suspected of having, or at risk of developing a tumor or contracting an infection are contemplated for therapy and diagnosis described herein. Samples obtained from such subject are likewise suitable for use in the methods of the invention.

By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease, e.g., so as to decrease tumor load, which decrease can include elimination of detectable cancerous cells, or so as to protect against disease caused by bacterial infection, which protection can include elimination of detectable bacterial cells; and/or (iii) relief, that is, causing the regression of clinical symptoms.

A variety of hosts are treatable according to the methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

In the context of anti-bacterial/viral methods, of interest are hosts that are susceptible to disease that can be caused by infection by a pathogen containing a serine protease, such as coronavirus or *Staphylococcus aureus*. In the methods of treatment of cancer, administering of the antibody specific for the serine protease, or an immunogenic composition that including the antibody facilitates a reduction in viability or metastatis of cancerous cells exposed to the antibody. The method involves administering to the subject an effective amount of a pharmaceutically acceptable formulation that comprises an antibody specific for a serine protease. Advantages of these methods are that the antibody can be directly or indirectly cytotoxic to cancer cells or pathogen expressing the serine protease of interest. Thus, the antibody can have the effect of retarding or otherwise arresting cell growth, and even inducing apoptosis, leading to cell death. Another advantage is that the cytotoxicity of the antibody can be dose dependent, and thus adjustable.

In a related embodiment, the subject being treated possesses an overly active serine protease. The serine protease can be present inside a cell or expressed on the cell surface, such as a cancer cell or a pathogen. This aspect can be beneficial in the context of the methods of the present disclosure in that cells expressing or presenting serine protease can be more amenable to treatment with an antibody of the present disclosure. The antibody can be administered to a subject, for example, where therapy is initiated at a point where presence of the serine protease is not detectable, and thus is not intended to be limiting. It is also possible to initiate antibody therapy prior to the first sign of disease symptoms, at the first sign of possible disease, or prior to or after diagnosis of a disease.

Prodrugs of the antibody composition of the present disclosure are also contemplated in the methods described herein. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

Cancer

More particularly, antibody compositions described herein can be administered to a subject (e.g. a human patient) to, for example, facilitate reduction of viability of cancerous cells, e.g., to reduce tumor size, reduce tumor load, and/or improve the clinical outcome in patients. In particular, antibody compositions can be used to disrupt the cell cycle of the cancer cell, and facilitate entry of the cell into apoptosis, e.g., by inducing cancerous cells to enter the pre-G0 cell cycle phase. The methods relating to cancer contemplated herein include, for example, use of antibody therapy alone or in combination with anti-cancer vaccine or therapy, as well as use of antibodies generated using serine protease antigens in anti-cancer vaccines (e.g., by passive immunization) or therapies. In certain cases, the method involves administering to a subject an antibody that specifically binds a serine protease. The methods are useful in the context of treating or preventing a wide variety of cancers, including carcinomas, sarcomas, leukemias, and lymphomas.

In certain embodiments, the antibody compositions may be advantageously used in an anti-cancer therapy, particularly where the cancerous cells present an active serine protease on an extracellularly accessible cell surface (e.g., an active MT-SP1). One example is a cancer that presents an A11-reactive antigen. Cancers that present an A11-reactive antigen can be identified by methods known in the art. Exemplary methods of detection and diagnosis will be described later below.

Cancers particularly amenable to antibody therapy can be identified by examining markers of cellular proliferation (e.g., Ki-67 antigen) and/or by examining the presence/accessibility of the active serine protease bound by A11 or by other antibodies specific for the serine protease (e.g., as in an in vitro assay).

For example, the presence of an active membrane-type serine protease type I (MTSP-1) in normal human tissue appears to be transient and low abundance. It is prevalent only in abnormal cells, such as metastasing cancer cells of epithelial origin. Since expression of high levels of active MTSP-1 exists predominantly in cancer cells, treatment with antibody compositions can be used to detect the presence and localize cancer growth, induce cytotoxicity, and can block tumor growth. In addition, antibody compositions can be used therapeutically to effect/prevent adhesion and invasion of cancer cells in other tissues.

Types of Cancer

Where the anti-cancer therapy comprises administration of an antibody composition described previously, the anti-cancer therapy can be particularly directed to dividing (replicating, proliferating) cancerous cells. For example, antibodies generated using a phage display library, such as A11, may bind an active serine protease associated with a cancerous cell with an improved binding affinity. As illustrated in the examples, A11 was highly effective in binding as well as inhibiting the activity of MTSP-1.

Exemplary cancers presenting an active serine protease include but not limited to cancer cells of epithelial origin.

Some examples are squamous carcinomas, gastric cancer, lymph node, colorectal cancer, and prostate cancer.

Antibody compositions can be used to treat cancers that present an A11-reactive antigen on a cell surface, including cancers that exhibit an extracellularly accessible A11-reactive antigen during cell division or during cell rest.

It should be noted that while active serine proteases and/or A11-reactive antigens may be expressed at higher levels on a cancer cell compared to a non-cancerous cell, this is not a limitation of the therapies disclosed herein. For example, where the cancer involves a cell type that can be replenished (e.g., B cell, T cell, or other cell of hematopoietic origin, as in leukemias and lymphomas), inhibition of normal cell growth can be acceptable since damage to a subject by depleting such cells can be treated (e.g., with drugs to stimulate repopulation of normal cells, e.g., GM-CSF, EPO, and the like).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be amenable to therapy by a method disclosed herein include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a method include, but are not limited to, B-cell lymphomas (e.g., Burkitt's lymphoma); Hodgkin's lymphoma; non-Hodgkin's lymphoma, and the like.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Further exemplary cancers that can be amenable to treatment using a methods disclosed herein include, but are not limited to, cancers of epithelial and neuroectodermal origin. Examples of epithelial origin include, but are not limited to, small cell lung cancer, cancers of the breast, eye lens, colon, pancreas, kidney, liver, ovary, and bronchial epithelium. In some embodiments, the methods do not include treatment of melanoma (i.e., the cancer is other than melanoma). In other embodiments, the methods do not include treatment of lymphoma (i.e., the cancer is other than lymphoma). The methods of the present disclosure may be used to treat cancer cells known to overexpress MTSP-1 or have dysregulated, active MTSP-1

Examples of cancers of neuroectodermal origin include, but are not limited to, Ewings sarcoma, spinal tumors, brain tumors, supratenbrial primative neuroectodermal tumors of infancy, tubulocystic carcinoma, mucinous tubular and spindle cell carcinoma, renal tumors, mediastinum tumors, neurogliomas, neuroblastomas, and sarcomas in adolescents and young adults.

Combinations with Other Cancer Therapies

As noted above, another feature of the methods is that a subject protease-binding agent can be administered to the subject in combination with one or more other therapies. For example, a therapy or treatment other than administration of antibody composition can be administered anywhere from simultaneously to up to 5 hours or more, e.g., 10 hours, 15 hours, 20 hours or more, prior to or after administration of a subject protease-binding agent. In certain embodiments, a subject protease-binding agent and other therapeutic intervention are administered or applied sequentially, e.g., where a subject protease-binding agent is administered before or after another therapeutic treatment. In yet other embodiments, a subject protease-binding agent and other therapy are administered simultaneously, e.g., where a subject protease-binding agent and a second therapy are administered at the same time, e.g., when the second therapy is a drug it can be administered along with a subject protease-binding agent as two separate formulations or combined into a single composition that is administered to the subject. Regardless of whether administered sequentially or simultaneously, as illustrated above, the treatments are considered to be administered together or in combination for purposes of the present disclosure.

Additional standard anti-cancer therapeutics that may or may not be administered in conjunction with a subject protease-binding agent, include but not limited to immunotherapy, chemotherapeutic agents and surgery (e.g., as those described further below). In addition, therapeutic administration of a subject protease-binding agent can also be post-therapeutic treatment of the subject with an anti-cancer therapy, where the anti-cancer therapy can be, for example, surgery, radiation therapy, administration of chemotherapeutic agents, and the like. Use of monoclonal antibodies, particularly monoclonal antibodies that can provide for complement-mediated killing, and/or antibody-dependent cellular cytotoxicity-mediated killing, of a target cell are of particular interest (e.g., treatment with an anti-serine protease antibody (e.g., A11 or an antibody specific for a serine protease of the present disclosure) after identification of a primary tumor composed of cells expressing an active serine protease (e.g., MT-SP1). Cancer therapy using a subject protease-binding agent in combination with immunotherapy that employs anti-serine protease antibodies is of particular interest.

For example, a subject protease-binding agent can be administered in combination with one or more chemotherapeutic agents (e.g., cyclophosphamide, doxorubicin, vincristine and prednisone (CHOP)), and/or in combination with radiation treatment and/or in combination with surgical intervention (e.g., pre- or post-surgery to remove a tumor), radiation therapy, bone marrow transplantation, biological response modifier treatment, and certain combinations of the foregoing. Radiation therapy includes, but is not limited to, X-rays or gamma rays that are delivered from either an externally applied source such as a beam, or by implantation of small radioactive sources.

Particular applications in which the methods and compositions find use include those described in U.S. Pat. Nos. 2,512,572; 3,892,801; 3,989,703; 4,057,548; 4,067,867; 4,079,056; 4,080,325; 4,136,101; 4,224,446; 4,306,064; 4,374,987; 4,421,913; 4,767,859; 3,981,983; 4,043,759; 4,093,607; 4,279,992; 4,376,767; 4,401,592; 4,489,065; 4,622,218; 4,625,014; 4,638,045; 4,671,958; 4,699,784; 4,785,080; 4,816,395; 4,886,780; 4,918,165; 4,925,662; 4,939,240; 4,983,586; 4,997,913; 5,024,998; 5,028,697; 5,030,719; 5,057,313; 5,059,413; 5,082,928; 5,106,950; 5,108,987; 4,106,488; 4,558,690; 4,662,359; 4,396,601; 4,497,796; 5,043,270; 5,166,149; 5,292,731; 5,354,753; 5,382,582; 5,698,556; 5,728,692; and 5,958,928; the disclosures of which are herein incorporated by reference.

Pathogen Infection

In the context of anti-pathogen methods, the treatment involves administering an effective amount of a protease-binding agent (e.g. antibodies) to a subject in order to decrease symptoms associated with an infection caused by bacteria or viruses that bear active proteases. The administering of the antibody to a subject can be directly or indirectly cytotoxic to the pathogen containing the protease. Thus, the method can have the effect of retarding or otherwise arresting pathogen growth, and even leading to pathogen death.

Exemplary pathogens include bacteria in the *Achromobacter* genus (e.g. *Burkholderia* and *Bordetella*), *Staphylococcus aureus* bacteria, *Mycobacterium tuberculosis*, plasmodium, retrovirus (e.g., HIV), herpesvirus (e.g., KSHV), coxsackievirus, coronavirus (e.g., SARS), and piconarvirus.

In addition, a subject protease-binding agent can be used to provide for passive immunotherapy in mammalian subjects. For example, a subject protease-binding agent can be provided in a pharmaceutical composition suitable for administration to a subject, so as to provide for passive protection of the subject against diseases or as a therapy to improve the clinical outcome in patients with established disease caused by the pathogen (e.g. decreased complication rate such as shock, decreased mortality rate, or decreased morbidity)

Dosage

In the methods, an effective amount of a subject protease-binding agent is administered to a subject in need thereof. For example, in some embodiments, a subject protease-binding agent inhibits growth of a cancer cell in a host when the subject protease-binding agent is administered in an effective amount. The amount administered varies depending upon the goal of the administration, the health and physical condition of the individual to be treated, age, the taxonomic group of individual to be treated (e.g., human, non-human primate, primate, etc.), the degree of resolution desired, the formulation of a subject protease-binding agent, the treating clinician's assessment of the medical situation, and other relevant factors. It is expected that the amount will fall in a relatively broad range that can be determined through routine trials. For example, the amount of subject protease-binding agent employed to inhibit cancer cell growth is not more than about the amount that could otherwise be irreversibly toxic to the subject (i.e., maximum tolerated dose). In other cases the amount is around or even well below the toxic threshold, but still in an immunoeffective concentration range, or even as low as threshold dose.

Individual doses are typically not less than an amount required to produce a measurable effect on the subject, and may be determined based on the pharmacokinetics and pharmacology for absorption, distribution, metabolism, and excretion ("ADME") of the antibody, and thus based on the disposition of the composition within the subject. This includes consideration of the route of administration as well as dosage amount, which can be adjusted for topical (applied directly where action is desired for mainly a local effect), enteral (applied via digestive tract for systemic or local effects when retained in part of the digestive tract), or parenteral (applied by routes other than the digestive tract for systemic or local effects) applications. For instance, administration of a subject protease-binding agent is typically via injection and often intravenous, intramuscular, intratumoral, or a combination thereof.

A subject protease-binding agent may be administered by infusion or by local injection, e.g. by infusion at a rate of about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 m g/m$^2$/day, about 3 m g/m$^2$/day to about 7 mg/m$^2$/day, about 4 mg/m$^2$/day to about 6 mg/m$^2$/day, about 4.5 mg/m$^2$/day to about 5.5 mg/m$^2$/day. Administration (e.g, by infusion) can be repeated over a desired period, e.g., repeated over a period of about 1 day to about 5 days or once every several days, for example, about five days, over about 1 month, about 2 months, etc. It also can be administered prior, at the time of, or after other therapeutic interventions, such as surgical intervention to remove cancerous cells. The antibody can also be administered as part of a combination therapy, in which at least one of an immunotherapy, a cancer chemotherapy or a radiation therapy is administered to the subject (as described in greater detail below).

Disposition of the antibody and its corresponding biological activity within a subject is typically gauged against the fraction of antibody present at a target of interest. For example, an antibody once administered can accumulate with a glycoconjugate or other biological target that concentrates the material in cancer cells and cancerous tissue. Thus dosing regimens in which the antibody is administered so as to accumulate in a target of interest over time can be part of a strategy to allow for lower individual doses. This can also mean that, for example, the dose of antibody that are cleared more slowly in vivo can be lowered relative to the effective concentration calculated from in vitro assays (e.g., effective amount in vitro approximates mM concentration, versus less than mM concentrations in vivo).

As an example, the effective amount of a dose or dosing regimen can be gauged from the IC50 of a given antibody for inhibiting or binding a serine protease. By "IC50" is intended the concentration of a drug required for 50% inhibition in vitro. Alternatively, the effective amount can be gauged from the EC50 of a given antibody concentration. By "EC50" is intended the plasma concentration required for obtaining 50% of a maximum effect in vivo.

In general, with respect to the antibody of the present disclosure, an effective amount is usually not more than 200× the calculated IC50. Typically, the amount of an antibody that is administered is less than about 200×, less than about 150×, less then about 100× and many embodiments less than about 75×, less than about 60×, 50×, 45×, 40×, 35×, 30×, 25×, 20×, 15×, 10× and even less than about 8× or 2× than the calculated IC50. In one embodiment, the effective amount is about 1× to 50× of the calculated IC50, and sometimes about 2× to 40×, about 3× to 30× or about 4× to 20× of the calculated IC50. In other embodiments, the effective amount is the same as the calculated IC50, and in certain embodiments the effective amount is an amount that is more than the calculated IC50.

An effective amount may not be more than 100× the calculated EC50. For instance, the amount of antibody that is administered is less than about 100×, less than about 50×, less than about 40×, 35×, 30×, or 25× and many embodiments less than about 20×, less than about 15× and even less than about 10×, 9×, 9×, 7×, 6×, 5×, 4×, 3×, 2× or 1× than the calculated EC50. In one embodiment, the effective amount is about 1× to 30× of the calculated EC50, and sometimes about 1× to 20×, or about 1× to 10× of the calculated EC50. In other embodiments, the effective amount is the same as the calculated EC50, and in certain embodiments the effective amount is an amount that is more than the calculated EC50.

Effective amounts can readily be determined empirically from assays, from safety and escalation and dose range trials, individual clinician-patient relationships, as well as in vitro and in vivo assays such as those described herein and illustrated in the Experimental section, below.

The IC50 may be calculated by inhibiting antibody binding in vitro. This aspect can be carried out by assessing the ability of the antibody of interest to inhibit A11 antibody binding to a serine protease (e.g. MT-SP1). In general, the procedure is carried out by standard ELISA in which the plates are coated with a serine protease as described in the examples at a concentration of about 10 μg/ml, and then processed and employed as described in the experimental examples to determine inhibition of antibody binding and the IC50. These antibodies and others suitable for various aspects of this purpose can be employed.

Routes of Administration

In practicing the methods, routes of administration (path by which a subject protease-binding agent is brought into a subject) may vary, where representative routes of administration for a subject protease-binding agent are described in greater detail below. A subject protease-binding agent alone or in combinations described above can be administered systemically (e.g., by parenteral administration, e.g., by an intravenous route) or locally (e.g., at a local tumor site, e.g., by intratumoral administration (e.g., into a solid tumor, into an involved lymph node in a lymphoma or leukemia), administration into a blood vessel supplying a solid tumor, etc.).

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The formulations of the present disclosure can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as transdermal compositions or transdermal delivery devices ("patches"), creams, gels, pastes, or foams, containing, in addition to the active ingredient, such carriers as are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing the antibody compositions. Similarly, unit dosage forms for injection or intravenous administration may comprise the antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms depend on the particular compound employed and the effect to be achieved, and the pharmacodynamics associated with each compound in the host.

Kits & Systems

Also provided are kits and systems that find use in practicing the methods, as described above. For example, kits and systems may include one or more of the compositions described herein, such as an anti-serine protease antibody (e.g. A11 or E2), a nucleic acid encoding the same (especially a nucleic acid encoding a CDR of a heavy and/or light chain of A11 or E2), or a recombinant cell containing the same. Other optional components of the kit include: buffers, etc., for administering the anti-serine protease antibody, and/or for performing a diagnostic assay. The recombinant nucleic acids of the kit may also have restrictions sites, multiple cloning sites, primer sites, etc to facilitate their ligation to constant regions of non-A11 encoding nucleic acids. The various components of the kit may be present in separate containers or certain compatible components may be precombined into a single container, as desired.

The kits and systems for practicing the methods may include one or more pharmaceutical formulations that include the antibody compositions described herein. As such, the kits may include a single pharmaceutical composition present as one or more unit dosages. In yet other embodiments, the kits may include two or more separate pharmaceutical compositions.

In addition to the above components, the kits may further include instructions for practicing the methods. These instructions may be present in the kits in a variety of forms, one or more of which may be present in or on the kit. One form in which these instructions may be present is as printed information on a suitable medium or substrate, e.g., a piece or pieces of paper on which the information is printed, in or on the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

A kit may be provided for use in treating a host suffering from a cellular proliferative disease or pathogenic infection. This kit includes a pharmaceutical composition comprising antibody specific for an active serine protease, and instructions for the effective use of the pharmaceutical composition in a method of treating a host suffering from a cancerous condition by inhibiting the growth of a cancer cell in a subject. Such instructions may include not only the appropriate handling properties, dosing regiment and method of administration, and the like, but can further include instructions to optionally screen the subject for an active serine protease associated with the disease. This aspect can assist the practitioner of the kit in gauging the potential responsiveness of the subject to treatment with an antibody of the present disclosure, including timing and duration of treatment relative to the type and growth stage of the cancer. Thus in another embodiment, the kit may further include an antibody or other reagent for detecting an active serine protease on an extracellularly accessible surface of a cancer cell, such as A11. In another embodiment, the kit includes antibody that comprises a conjugate with a detectable label, such as a fluorophore.

A kit may also be provided for use in treating a host at risk of, or having, a disease or disease symptom of infection by bacteria or virus bearing a protease (e.g. P1-Arg-specific protease). This kit includes a pharmaceutical composition comprising an antibody specific thereto, and instructions for the effective use in treatment of a host having, or at risk of, bacterial/viral infection. Such instructions may include not only the appropriate handling properties, dosing regiment and method of administration, and the like, but can further include instructions to optionally screen the subject for the bacterial/viral specific protease. This aspect assists the practitioner of the kit in gauging the potential responsiveness of the subject to treatment with an antibody of the present disclosure. The kit may further include an antibody or other reagent, such as A11 or E2, for detecting a serine protease on an extracellularly accessible surface of a bacterial cell.

The term "system" as employed herein refers to a collection of antibodies described herein and one or more second therapeutic agents, present in single or disparate compositions that are brought together for the purpose of practicing the methods. For example, separately obtained antibody specific to serine proteases and chemotherapy dosage forms brought together and coadministered to a subject are a system according to the present disclosure.

The following examples further illustrate the present invention and should not be construed as in any way limiting its scope.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Materials and Methods

The following methods and materials were used in the Examples below.

Phage Display Library Construction.

A Fab library was used to identify inhibitory antibodies against the human MT-SP1 protease domain (hMT-SP1). A fully human naïve Fab phage display was constructed using methods described in de Haard H J et al. (*J Biol Chem* 1999, 274: 18218-30). Peripheral blood lymphocyte RNA was converted to cDNA by reverse transcriptase primed with random hexa-nucleotides. cDNA encoding the heavy or light chains of the Fabs were amplified by PCR using the primers of Haard H J et al., supra. The resulting library was cloned into a phagemid vector which fuses a C-terminal hexa-histidine and c-myc tag to the heavy chain. Large scale phage rescue was performed using M13K07 helper phage. The library was stored at −80° C.

Phage Display Panning and Identification of Inhibitory Fab.

Active MT-SP1 was bound to wells of a 96-well ELISA plate. The panning was accomplished in three rounds with increasing stringency against hMT-SP1 adsorbed to wells. ELISAs were performed to verify binding of the identified Fabs to hMT-SP1. ELISA positive clones were expressed, purified and tested for inhibition of MT-SP1. Individual clones were sequenced to verify their uniqueness.

Protein Expression and Purification from *E. coli*.

MT-SP1 and MT-SP1 mutants were expressed in *Escherichia coli* and purified as previously described (Farady C J et al. *J Mol Biol* 2007, 369: 1041-51, Takeuchi et al. *Proc Natl Acad Sci USA* 1999, 96: 11054-611999). A11 was expressed in *E. coli* BL21 DE3 cells. Cultures were grown in 1 L of 2×YT containing 100 µg/ml ampicillin and 0.1% glucose at 37° C. and 250 rpm to an $OD_{600}$ of 0.6-0.8. The temperature was then reduced to 25° C. and the cultures were induced with the addition of 0.5 mM IPTG. After 18 hours of growth, the bacteria was harvested and pelleted by centrifugation. The cells were resuspended in 25 mL of buffer containing 0.2 M Tris pH 8.0, 0.5 mM EDTA and 0.5 M sucrose. The resuspended solution was left on ice for 1 hour. The solution was then pelleted and the periplasmic fraction was run over a $Ni^{2+}$ column prewashed with wash buffer (50 mM Tris pH 8.0, 250 mM NaCl). The Ni column was then washed with 10 column volumes of the wash buffer and the Fab was eluted with 250 mM imidazole in 50 mM Tris pH8.0, 100 mM NaCl. Size exclusion chromatography was carried out on the eluted A11 using a Superdex S75 26/60 with a 50 mM Tris pH 8.0, 100 mM KCl, 5% glycerol buffer.

Mutagenesis of A11.

A11 mutants ArgH100aAla, ArgH100bAla, and ArgH115bLys were all created using the Quikchange kit from Stratagene. Sequences were verified by DNA sequencing. Expression and purification of A11 mutants was carried out as described above.

Trichoderma reesei Expression Vector Construction.

Two independent expression vectors were constructed, one for expression of the Fab heavy chain (pCBHIxFabA11 H1) and one for the light chain (pCBHIxFabA11 L1). In each case, the Fab chains were produced as fusion proteins with the *T. reesei* CBHI (cellobiohydrolase I, cel7a) catalytic core and linker region. A Kex2 cleavage site (Val Ala Val Tyr Lys Arg) was positioned between the CBHI and the Fab chain to allow cleavage of the fusion protein after the Arg residue and release of the Fab chain during secretion.

The following segments of DNA were assembled in the construction of pCBHIxFabA11 H1 and pCBHIxFabA11 L1. The *T. reesei* cbh1 promoter and coding region, starting at a naturally occurring XbaI site approximately 1500 bp upstream of the coding region. The synthetic, codon optimized coding region for each Fab chain was fused to the end of the CBHI linker region at a created Spa restriction site (see below). Immediately after the Fab stop codon was an AscI restriction site followed by the *T. reesei* cbh1 terminator region (356 bp). This was followed by a 2.75 kb fragment of *Aspergillus nidulans* genomic DNA, including the promoter, coding region and terminator of the amdS (acetamidase) gene. The above DNA fragments were inserted in pNEB193 (New England Biolabs, Inc., USA) between the XbaI and KpnI sites of the multiple cloning site.

The following changes were made within the cbh1 open reading frame. The codon for amino acid 212 of the mature CBHI protein was changed from GAG (Glutamic acid) to CAG (Glutamine) resulting in production of an inactive form of CBHI. Within the coding region for the CBHI linker a change was made to create a Spa restriction site. This altered the DNA sequence from ACCCAG to ACTAGT, changing the amino acid sequence at the end of the CBHI linker region from Thr Gln to Thr Ser. The Gln in this sequence represents the first amino acid of the cellulose binding domain of CBHI.

*T. reesei* transformation.

*Trichoderma reesei* GICC20000150 was derived from strain RL-P37 (Sheir-Neiss et al. *Applied Microbiology and Biotechnology* 1984, 20:46) by sequential deletion of the genes encoding the four major secreted cellulases (cel7a, cel6a, cel7b and cel5a). Transformation was performed using a Bio-Rad Laboratories, Inc. (Hercules, Calif.) model PDS-1000/He biolistic particle delivery system according to the manufacturer's instructions. Transformants were selected on solid medium containing acetamide as the sole nitrogen source. For antibody production, transformants were cultured in a liquid minimal medium containing lactose as carbon source as described previously (Ilmen et al. *Appl Environ Microbial* 1997, 63: 1298-306), except that 100 mM piperazine-N,N-bis(3-propanesulfonic acid) (Calbiochem) was included to maintain the pH at 5.5. In order to produce Fab it was necessary for transformants to have taken up both the heavy and light chain expression vectors. However, both expression vectors had the same amdS selectable marker so it was not immediately possible to recognize co-transformants. Culture supernatants were analyzed by SDS-PAGE under reducing conditions and those that contained the highest level of a 25 kDa band (representing heavy and/or light chain) and an apparent 60 kDa band (representing the CBHI core and linker) were selected for further analysis.

Purification of A11 from *T. reesei* Expression.

Media from the *Trichoderma* expression was adjusted to pH 5.5. For an initial crude purification, the media was run over an SP sepharose column equilibrated with Wash Buffer 1 (100 mM MES pH 5.5, 50 mM NaCl). The column was then washed with 5 column volumes of Wash Buffer 1, followed by 5 column volumes of Wash Buffer 2 (50 mM Tricine pH 8.0). A11 was eluted with 3 column volumes of 50 mM Tricine pH 8.0, 500 mM NaCl. The elution was buffer exchanged into 100 mM MES pH 5.5, 50 mM NaCl and loaded onto a MonoS HR 5/5 column. The column was washed with Wash Buffer 1 followed by Wash Buffer 2. Elution was then carried out in a 0-100% gradient of Wash Buffer 2 to Wash buffer 2 containing 500 mM NaCl. Further purification was carried out on a Superdex 75 26/60 size exclusion column with a 50 mM Tris pH 8.0, 100 mM KCl, 5% glycerol buffer.

Steady State Kinetics.

Kinetics were carried out as previously described (Farady C J et al. *J Mol Biol* 2007, 369: 1041-51). Briefly, all reactions were carried out in 50 mM Tris, pH 8.8, 50 mM NaCl, 0.01% Tween-20 in 96-well, medium binding, flat-bottomed plate (Corning), and cleavage of substrate (Spectrazyme-tPA (hexahydrotyrosyl-Gly-Arg-pNA), American Diagnostica, Greenwich, Conn.) was monitored in a UVmax Microplate Reader (Molecular Devices Corporation, Palo Alto, Calif.). $K_I$'s were measured using the tight-binding inhibition equations of Williams and Morrison (Methods Enzymol 1979, 63: 437-67). When measuring the effect mutations to MT-SP1 had on the strength of the interaction between the protease and inhibitor, $IC_{50}$ values were used instead of $K_I$'s. Reactions to determine the $IC_{50}$'s were carried out by incubating 0.2 nM enzyme with inhibitor for >5 hours to assure steady-state behavior of the system. Relative $K_I$'s were then calculated from $IC_{50}$ values as shown previously in order to normalize the $IC_{50}$ with respect to the strength of the protease/substrate interaction (Chou T et al. Mol Pharmacol 1974, 10: 235-47). Inhibitory activity against related proteases was measured using a similar assay monitoring the cleavage of a p-nitroanilide substrate. 10 nM Thrombin, fXa, and plasmin (Haematologic Technologies, Inc., Essex Junction, VT.) were incubated with 1 µM Fab, and the reaction was monitored using 1 mM of the substrate T1637 (Sigma, St. Louis, Mo.). 10 nM tPA and uPA (American Diagnostica) were incubated with 1 µM Fab, and the reaction was monitored using 1 mM Spectrazyme-tPA and 400 mM Spectrazyme-UK (American Diagnostica), respectively. Inhibitor activity was also measured using the chromogenic substrate Spectrafluor tPA (American diagnostica, Inc.). In that experiment, A11 antibody, of which concentration was varied from 0-250 nM, was incubated with recombinant MT-SP1 for five hours and proteolysis measured through activation of Spectrafluor tPA (America Diagnostica Inc). Kaleidagraph 3.6 was used to fit all graphs and equations (Synergy Software, Reading, Pa.).

MT-SP1/A11 Digestion.

The digestion of A11 by MT-SP1 was carried out as previously described (Farady C J et al. *J Mol Biol* 2007, 369: 1041-51). A11 was incubated at 2 µM with 0.1 nM MT-SP1 in either 100 mM MES pH 6.0, 100 mM NaCl buffer or 50 mM Tris pH 8.0, 100 mM NaCl. After 120 hours, the samples were run on a 4-20% Tris-Glycine SDS-PAGE gel (Invitrogen) to visualize.

Crystallization and Data Collection.

A11 was incubated with MT-SP1 at 1:1 molar ratio and the complex was purified by gel filtration using a Superdex S75 26/60 column in a buffer containing 50 mM Tris pH8.0, 100 mM NaCl, 5% glycerol. The purified complex was then concentrated to ~15 mg/ml. Initial crystallization conditions were discovered using a nanoliter-scale Mosquito robot (TTP Labtech). The A11/MT-SP1 complex was crystallized in 16% PEG 3350, 0.23 M $MgSO_4$, 0.4% isopropanol, 3% glycerol and 0.12 M $AmSO_4$ in hanging drop by vapor diffusion. Crystals belonging to the hexagonal space group $P6_4$ (a=b=130.6 Å and c=96.94 Å) grew in three days and were cryoprotected in the mother liquor supplemented with 30% sucrose. Diffraction data were collected at beamline 8.3.1 at the Advanced Light Source at LBNL. A11/MT-SP1 data were reduced and scaled using MOSFLM and scala in the CCP4 suite of programs (*Acta Crystallogr D Biol Crystallogr* 1994, 50: 760-3).

Structure Determination and Refinement.

The structure of A11/MT-SP1 was solved by molecular replacement using Phaser (Read R J *Acta Crystallogr D Biol Crystallogr* 2001, 57: 1373-82) in CCP4 (*Acta Crystallogr D Biol Crystallogr*, supra), first searching for MT-SP1 (using 1EAX as search model), then searching for the Fab fragment with its H3 loop truncated (using 2HFF as search model). Following molecular replacement, automatic building in ARP/wARP (Evrard G X et al. *Acta Crystallogr D Biol Crystallogr* 2007, 63: 108-17) and manual building yielded the final structures. Restrained refinements cycles were done using REFMAC5 (Murshudov G N et al. *Acta Crystallogr D Biol Crystallogr* 1999, 55: 247-55) for the A11/MT-SP1 structure. TLS refinement was applied at the last stage of the refinement. In the final structure there was no density for the heavy chain residues 129-133, 213-215, or protease Ala204. There was no side chain density for A11 light chain residues Glu1, Glu143, Lys188, and Glu213, or heavy chain residues Glu1, Lys201, and Lys210, so the side chains were not modeled. These regions are often disordered in Fab structures, and make no interactions with the protease. The quality of the final structures was assessed using Molprobity (Lovell S C et al. *Proteins* 2003, 50: 437-50). Buried surface area calculations were performed using PISA (Krissinel E et a *J Mol Biol* 2007, 372: 774-97).

Fluorescent Labeling.

scFv, diabody, Fab and IgG were labeled with AlexaFluor 594 (for microscopy) and Alexafluor 680 (in vivo imaging) (Invitrogen) according to the manufacturer's protocol. Proteins were purified from unreacted dye on a Superdex 75 FPLC column (GE Healthcare). Degree of labeling was determined using UV/VIS spectrometry as directed in manufacturer's protocol. In fluorescent experiments, concentrations refer to dye molecules rather than the labeled protein.

Surface Plasmon Resonance.

The association and dissociation curves for MT-SP1 and the inactive zymogen MT-SP1 R15A were obtained by surface plasmon resonance using a BIAcore Biosensor T100 (GE Healthcare). The A11 Fab (ligand), in 25 mM sodium acetate buffer, pH=5.0, was covalently immobilized onto a CM5 chip according to the manufacturer's protocol with a final immobilization level of ~70 RU. The reference channel was treated using the same chemistry as the ligand coupled surface. Enzymes (analytes) were washed in HBS-EP buffer (10 mM HEPES pH=7.4, 150 mM NaCl, 3 mM EDTA and 0.005% [v/v] Tween 20) and injected in concentrations varying from 50 nM to 1 µM across the chip surface at 20 µl/min to minimize mass transfer effects. Surface regenerations were performed with 100 mM Glycine pH=2.2, allowing a complete return to baseline. The sensorgram of the reference surface was subtracted from the ligand conjugated surface for each injection. No binding was observed for MT-SP1 R15A at concentrations up to 1 µM.

Cell Culture.

Human cancer cell lines HT29, PC3, MDA-MB-231, MCF7, MDA-MB-468, and LNCaP were obtained from the American Type Culture Collection (www.atcc.org) and maintained in the recommended media. Activity Assays: 70-90% confluent adherent cells were rinsed in PBS and lifted using Enzyme-Free Cell Dissociation Buffer (Invitrogen). Cells were washed twice in serum-free media and counted, then resuspended in serum-free media and aliquoted into round-bottomed 96-well plates, ranging from 30,000-60,000 cells per well, depending on the cell line. E2 Fab and serum-free media were added for a final volume of 95 µl and final inhibitor concentration of 200 nM. For total inhibition, 5 µl of 25× Complete Inhibitor Cocktail (Roche) in water was added along with 90 µl of serum-free media. After 1 hour incubation at 37° C., 5% $CO_2$, Spectrofluor tPA (American Diagnostica Inc.) was added to a final concentration of 500 µM. Fluorescence was measured on a SpectraMax Gemini EM plate reader (MDS Inc.) with an excitation/emission wavelengths of 380/460 nm. Fluorescence was measured for one hour or until proteolysis ceased to be linear. Fluorescence was also measured in media only to correct for non-proteolytically-mediated substrate hydrolysis. The prostate cancer cell line PC3 showed the largest amount of $P_1$-Arg specific proteolysis, but very little of it was attributable to MT-SP1, so this data was not included. Prior to inhibition assays, these experiments were carried out with 10,000-100,000 cells per well to ensure that we were working in the range where fluorescence increased linearly with cell number. Activity assays were conducted in sextuplicate.

Fluorescent Imaging of Cells.

Round glass microscope cover slips (Fisher Scientific) were flame-sterilized and placed in 12 well plates. Cells were passaged into these wells and grown to a confluency of 40-90%. 12-16 hours prior to imaging, cells were switched to serum-free media. One hour prior to imaging, fresh serum—free media was added with enough Alexa Fluor 594-labeled E2 scFv to obtain a final fluorphore concentration of 300 nM. Cells were returned to the incubator for 1-2 hours after which slides were removed, rinsed in PBS, and immediately imaged on a Nikon Eclipse E800 fluorescent microscope outfitted with a G-2E/C filter combination. All cells were imaged within 10 minutes of removal from incubator. For the HAI-1 blocking experiment, recombinant human HAI-1 (R&D Systems) was diluted to 1 µM in PBS and added along with fresh serum-free media to a final concentration of 200 nM and cells incubated under normal conditions for three hours. At this time, fluorescently labeled E2 scFv was added to the blocked cells, as well as to unblocked cells, for a final dye concentration of 100 nM. Cells were incubated for another hour and then rinsed in PBS and imaged.

Fluorescent Imaging of Mice.

Mice were fed an alfalfa-free diet of Harlan Teklad Global 2018 rodent feed to minimize background fluorescence. Mice were anesthetized with 1.5-2% isofluorane and imaged prior to injection. Alexa Fluor 680-labeled A11 IgG, E2 Fab, and E2 diabody were injected to the tail veins with total amount of injected dye ranging from 0.5-2 nanomoles. Images were collected on an IVIS 50 (Caliper Life Sciences) at set intervals depending on the antibody construct injected. For the IgG studies, two MCF7 mice were injected with approximately 2 nanomoles of dye and anesthetized and imaged periodically for 50 hours. Two MDA-MB-231/Luc+ tumor-bearing mice were injected with approximately 0.7-1 nanomoles of dye and imaged in the same manner. In the images presented, ROI analysis of the entire mouse using Living Image 2.50.2 software (Caliper Life Sciences) indicated the relative signal coming from each mouse four hours after injection. Intensity minima and maxima were adjusted to compensate for the difference in total signal from the mice. A11 in vivo studies were performed as directed under institutional approval (IACUC approval #AN077922-02).

Example 1

Identification of A11 Fab

A phage-displayed Fab library created from human naïve B-cells was used to identify inhibitory antibodies against human MT-SP1 protease domain (de Haard H J et al. *J Biol Chem* 1999, 274: 18218-30). Seven unique antibodies were identified that exhibited inhibitory activity against MT-SP1 in preliminary activity assays with purified protein (FIG. 1). Of these, the Fab A11 demonstrated the most potent inhibition of MT-SP1. Analysis of the amino acid sequence shows that A11 has a $V_H3$ heavy chain template and a $V_\kappa3$ light chain. The amino acid sequences of the hypervariable regions are shown in FIG. 2. A11 has a 17 residue H3 loop, which is longer than the average 12-14 residue H3 loop found in human antibodies (Zemlin M et al. *J Mol Biol* 2003, 334: 733-49; Wu T T et al. *Proteins* 1993, 16: 1-7).

Example 2

Expression and Purification of A11

The recombinant A11 Fab was periplasmically expressed in *E. coli* BL21(DE3) cells utilizing the original phagemid vector (de Haard H J et al. *J Biol Chem* 1999, 274: 18218-30). The periplasmic fraction was initially passed over a $Ni^{2+}$ column, followed by a Superdex S75 26/60 size exclusion column to yield ~3 mg/L protein which was determined to be >98% pure by SDS-PAGE analysis. This expression level was sufficient to perform the biochemical assays.

To boost the production levels of the Fab, a *Trichoderma reesei* system was used for A11 expression. The A11 light and heavy chains were cloned into individual expression vectors and expressed as CBH1 fusion proteins with a Kex2 cleavage site between the domains. Expression as the fusion protein allowed for secretion of the expressed protein with cleavage from the CBH1 domain upon secretion. This expression system significantly increased the yield of A11 compared to the *E. coli* system, resulting in the purification of ~200 mg/L of culture from the growth media. Purification of the secreted protein from the media was accomplished with a simple three step purification and yielded protein that was >98% pure by SDS-PAGE analysis. This expression level is higher than the majority of expression levels reported for Fabs and at the high end of Fab expression in *T. reesei*, affirming that *T. reesei* offers a simple system for high expression of Fab antibodies (Arbabi-Ghahroudi M et al. *Cancer Metastasis Rev* 2005, 24: 501-19; Keranen S et al. *Curr Opin Biotechnol* 1995, 6: 534-7). The expression system produced a sufficient quantity of antibody to simplify crystallization of the A11/MT-SP1 complex and is useful for in vivo applications.

Example 3

Steady State Kinetics

Steady state kinetics experiments were performed to investigate the inhibition of MT-SP1 by A11. A11 Fab binds tightly to MT-SP1 and competitively inhibits small-molecule substrate turnover (Spectrazyme tPA) with a $K_I$ of 720 µM (Table 3) or ~50 µM when converted to IgG. E2, another anti-MT-SP1 Fab antibody has a $K_I$ of 12 µM. To determine the specificity of A11, assays were performed with the related serine proteases factor Xa (fXa), thrombin, plasmin, tissue plasminogen activator (tPA), urokinase plasminogen activator (uPA) and hepatocyte growth factor activator (HGFA). A11 showed no inhibition of these proteases at a concentration of 1 µM. Additionally, the $K_I$ measured against epithin, the mouse homologue of MT-SP1 that shares 86% sequence homology in the protease domain, was nearly 1000-fold higher. These results demonstrate that A11 inhibition of MT-SP1 is potent and selective.

Example 4

MT-SP1 Point Mutants

Figure 3:
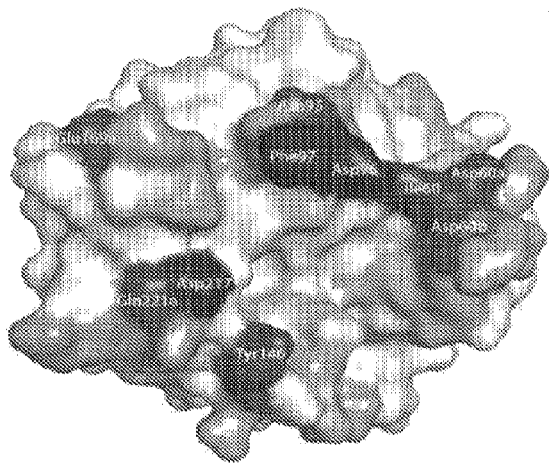
FIG. 3 shows the various MT-SP1 alanine scanning mutants.

A11 inhibition of a library of MT-SP1 alanine mutants was tested in this example. The $K_I$ values of A11 against the MT-SP1 point mutants were determined to locate residues critical for the protease/antibody interaction. The results indicate that side chains from four of the six MT-SP1 surface loops are important to binding (FIG. 3). The change in $K_I$ values upon mutation of the residue to alanine is indicated on the surface of the MT-SP1 structure. Red indicates an increase in $K_I$ of >100 fold; pink 3-10 fold; and gray <3 fold change. The mutation of Asp96 and Phe97 had the largest effect on $K_I$, increasing to >1 µM in both cases, more than $10^4$ fold over wild-type. The high selectivity of A11 for MT-SP1 over the other related serine proteases tested may be imparted by Phe97. Of the seven other proteases tested, only HGFA and epithin (the mouse homologue of MT-SP1) have a Phe residue at position 97. Mutation of Asp217 also showed a large increase in $K_I$ to 99 nM, a ~250 fold increase, appearing to have a large role in A11 binding. In addition, the point mutants identified contacts between A11 and MT-SP1 residues 160, D60a, D60b, N95, Y146, E169, and K224. These residues resulted in a change in $K_I$ of between 5— and 6-fold. This binding footpint indicates the overall importance of the MT-SP1 surface loops in A11 binding. While these point mutants indicate that binding to the surface loops of MT-SP1 is critical for the antibody inhibitor, this is not the case for the canonical serine protease inhibitor BPTI (Farady C J et al. *J Mol Biol* 2007, 369: 1041-51). Mutations to the MT-SP1 surface loops minimally affected the inhibitory activity of BPTI, lending to the broad specificity of these Kunitz-type inhibitors against serine proteases. In contrast, the protease surface loops for A11 binding provides highly specific interactions with MT-SP1.

Example 6

A11 H3 Loop Mutations

In this example, ArgH100a and ArgH100b in A11 H3 loop are found to play a role in the binding of MT-SP1, interacting directly with the protease S1 pocket (Farady C J et al. *J Mol Biol* 2008, 380: 351-60). Mutations were made to the double Arg motif to investigate the possible role of these residues in MT-SP1 active site binding. The mutations ArgH100aAla, ArgH100bAla and ArgH100bLys were made and the $K_I$'s were measured. See table 3 below.

TABLE 3

The $K_I$ values of A11 and various point mutants.

| Antibody | $K_I$ (nM) |
| --- | --- |
| A11 | 0.72 |
| A11 H R100bA | 180 |
| A11 H R100bK | 180 |
| A11 H R100aA | 1.5 |
| A11 (Epithin) | 87 |

For ArgH100aAla, the $K_I$ was determined to be 1.5 nM, about 2-fold greater than the wild-type inhibitor, indicating that the mutant made fewer contacts with MT-SP1 than the wild-type A11. Both of the point mutants ArgH100bAla and ArgH100bLys had $K_I$'s of 180 nM against MT-SP1. These $K_I$ values were 250-fold higher than for the wild-type A11, indicating that ArgH100b was important in MT-SP1 binding. Since the residue binds in the S1 pocket, the mutation ArgH100bAla caused a big change in $K_I$. A conservative mutation of ArgH100bLys also resulted in a big change in $K_I$. As such, the loop does not bind the active site in a canonical fashion. The lysine mutation could place the side chain in a position that destabilized the interacting with the S1 pocket. In contrast, the similar mutation of Lys to Arg at the P1 position of the standard mechanism inhibitor BTPI had a very minimal effect on the $K_I$ against trypsin (Krowarsch D et al. *J Mol Biol* 1999, 289: 175-86).

Example 8

MT-SP1 Digestion of A11

Based on Example 7, the H3 loop of A11 was found to interact with the substrate binding pocket in MT-SP1 in a noncanonical orientation. To further investigate this interaction, the Fab was incubated with MT-SP1 at both pH 8.0 and pH 6.0. Previous experiments had shown that incubation of standard mechanism inhibitors with the target protease at low pH resulted in cleavage (Farady C J et al. *J Mol Biol* 2007, 369: 1041-51; Ozawa K et al. *J Biol Chem* 1966, 241: 3955-61; McGrath M E et al. *J Biol Chem* 1991, 266: 6620-5). Different from the standard mechanism inhibitors, MT-SP1 was unable to cleave A11 at both the standard reaction pH (8.0) and a more acidic pH (6.0). This indicated that A11 either did not insert a loop into the active site of MT-SP1 or that it was not bound in a substrate-like manner. Based on these results and the previous examples, the H3 loop of A11 may bind to the active site in a non-canonical fashion, thereby avoiding cleavage.

Example 9

Structure of the MT-SP1-Inhibitor Complex

The crystal structure of A11 in complex with MT-SP1 was also determined. Details are shown in table 4 below.

TABLE 4

Data collection and refinement statistics (molecular replacement) for A11 complexed with MT-SP1.

| Data collection | | Refinement | |
| --- | --- | --- | --- |
| Space group | $P6_4$ | Resolution (Å) | 20-2.1 |
| Cell dimensions | | | (2.155-2.1) |
| a, b, c (Å) | 130.6, 130.6, 96.9 | No. reflections | 51,934 (3,815) |
| $\alpha, \beta, \gamma$ (°) | 90, 90, 120 | $R_{work}/R_{free}$ | 16.1/19.5 |
| Resolution (Å) | 113-2.10 (2.21-2.1) | No. atoms Protein | 5,108 |
| $R_{sym}$ or $R_{merge}$ | 0.087 (0.349[1]) | Ligand/ion | 36 (1 sucrose, 2 glycerols) |
| I/σI | 11.7 (2.2) | Water | 462 |
| Completeness (%) | 100% (100%) | B-factors | |
| Redundancy | 7.3 (6.7) | Protein | 59.5 |
| | | Ligand/ion | 53.7 |
| | | Water | 63.3 |
| | | R.m.s. deviations | |
| | | Bond lengths (Å) | 0.017 |
| | | Bond angles (°) | 1.64 |

Values in parentheses are for highest-resolution shell.
Test set was 5% of total reflections for A11 dataset.
[1]Rpim value reported for high resolution shell.

Figure 4:
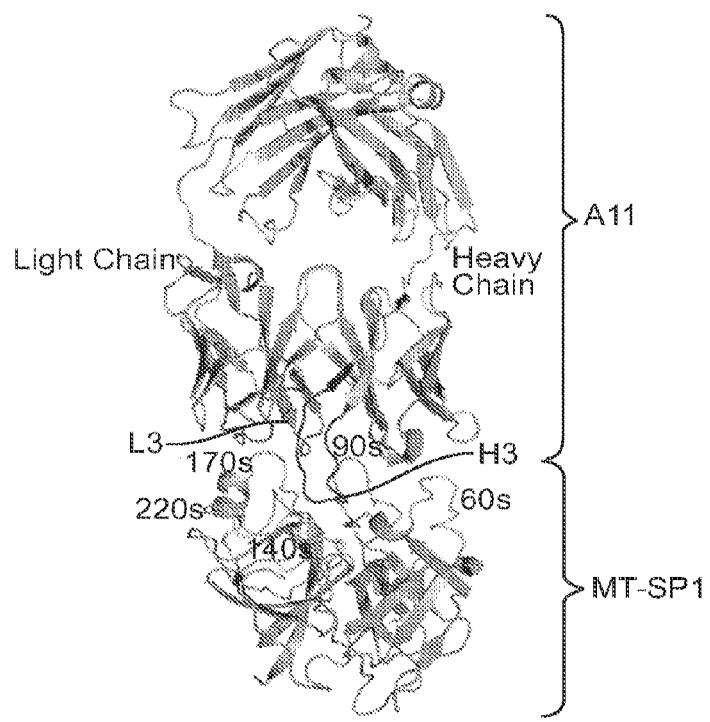
FIG. 4 depicts the structure of the A11/MT-SP1 complex.
Figure 5:
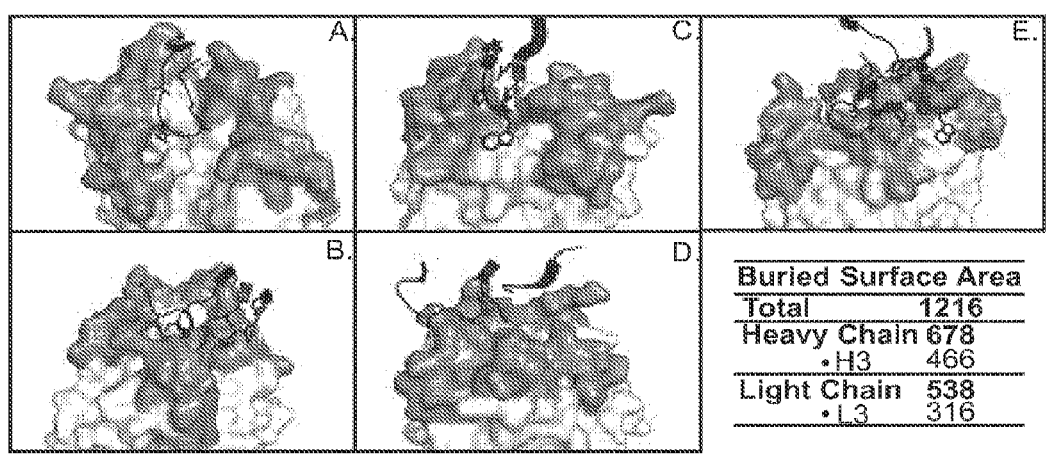
FIG. 5 shows Interaction of the A11 variable loops with MT-SP1. Panel A, The A11 H3 loop interacting with the MT-SP1 surface accounts for the majority of the buried surface area contributed by the heavy chain variable loops. The loop inserts Arg 100b into the active site while making very few additional contacts. Panel B, The H1 and H2 loops contact residues in the 60s and 90s loops of MT-SP1. Panel C, The long L3 loop of A11 makes a number of contacts with the surface of MT-SP1, burying nearly as much surface area as the H3 loop. Panel D, The L1 loop contacts both the 170s and 220s loops while the L2 loop makes no contacts with MT-SP1. Panel E, Together the H2, H3 and L3 loops of A11 utilize Phe97 of MT-SP1 as an anchor point for binding and recognition, an interaction that is crucial to formation of the complex. The heavy and light chains loops are shown as ribbons and the MT-SP1 side chains that interact with each variable loop are shaded gray in the space-filled model.

The A11/MT-SP1 complex crystallized with only one copy of the complex in the asymmetric unit, and the structure was determined by molecular replacement to 2.1 Å. Consistent with the alanine scanning results presented in Example 4, the inhibitor A11 bound to MT-SP1 and capped the active site through numerous interactions with the protease surface loops (FIG. 4). These loops surrounded the substrate-binding groove of the protease and modulated macromolecular substrate recognition. The protease surface loops are sites of high diversity among the well-conserved family of trypsin-like serine proteases (Perona J J et al. *J Biol Chem* 1997, 272: 29987-90). The heavy chain of A11 bound to the protease at the 60's and 90's loops while the light chain interacted with the 90's, 170's and 220's loops (FIG. 5). The H3 loop (dark ribbon) inserts ArgH100b into the active site while making very few additional contacts while E2 H3 loop (lower panel, dark ribbon) by comparison makes more interaction with the substrate binding cleft (FIG. 5, panel A). In total, A11 buried 1,216 Å$^2$ of surface area. Both the light chain and heavy chain loops made significant contacts with the protease surface. The light chain buried 538 Å$^2$ of surface area (44% of total), while the heavy chain a similar 678 Å$^2$ of surface area (56% of total). Of this, the long H3 loop is responsible for the majority of contacts that the heavy chain had with MT-SP1, burying 466 Å$^2$ of surface area (69% buried surface attributed to the heavy chain).

The structure agreed well with the alanine scanning data and confirmed Asp96 and Phe97 of the MT-SP1 are important for inhibitor binding. The long L3 loop (dark ribbon in FIG. 5, panel C) of A11 makes a number of contacts with the surface of MT-SP1, burying nearly as much surface area as the H3 loop, while the L3 loop of E2 (dark ribbon in FIG. 5, panel D) is much shorter and makes very little contact with the surface of MT-SP1. The hypervariable loops L3 and H2 combined to grab the 90's loop, with the Phe97 side chain of MT-SP1 binding in a hydrophobic cavity formed by TyrH58 of H2 and L3 residue ProL95a. The ArgL91 of L3 side chain and its phenyl ring formed a pi-stacking interaction. The H2, H3, and L3 loops of A11 utilize Phe97 of MT-SP1 as an anchor point for binding and recognition (FIG. 5, panel E). Furthermore, Asp96 was rotated 180° from its position in the apo MT-SP1 structure, where it formed the bottom of the S4 pocket. Asp96 also forms hydrogen bonds between SerH52, SerH54, and SerH56. As for the second important residue revealed by the MT-SP1 alanine scanning mutations, Asp217 formed a hydrogen bond with the SerL31. A mutation of Asp217 might cause structural changes to the entire 220s loop, thereby interrupting additional interactions with A11.

The $V_\kappa 3$ architecture of the A11 light chain allows for an extended L3 loop, which bound in a groove between the 90's and 170's loop on the protease (FIG. 5, panel C). In particular, TrpL94 made significant interactions with the protease 170's loop. The indole side chain stacked on the side chains of Thr177 and Pro178, while the backbone amide made a strong hydrogen bond with the backbone carbonyl of Gln175 (2.9 Å). In addition, Tyr96 made a hydrophobic interaction with Phe97. The L1 loop also made several contacts with the protease 170's and 220's loop. The Oγ of SerL31 hydrogen bound to Asp217 Oδ2 (2.7 Å) and made a water mediated hydrogen bond to Lys224 on the protease 220's loop. SerL27a formed a 2.8 Å hydrogen bond with NE of the protease Gln174. The L2 loop was positioned so that it made no interactions with MT-SP1.

The heavy chain loops of A11 made contacts with the 60s and 90s loops while inserting the H3 loop into the S1 binding pocket (FIG. 5, panels A and E). The H1 loop interacted mainly with Asp60b, with the Oγ of Ser30 and Ser31 forming hydrogen bonds with the Asp60b side chain. The side chain of Ala33 was involved in a hydrophobic interaction with Phe97. The H2 loop also made hydrophobic interactions with Phe97 through Ala50 and Tyr58. In addition, hydrogen bonds were made to the side chains of Asn95 and Asp96 through the Oγ of Ser52, Ser53 and Ser56 as well as the side chain of Tyr58.

Figure 6:
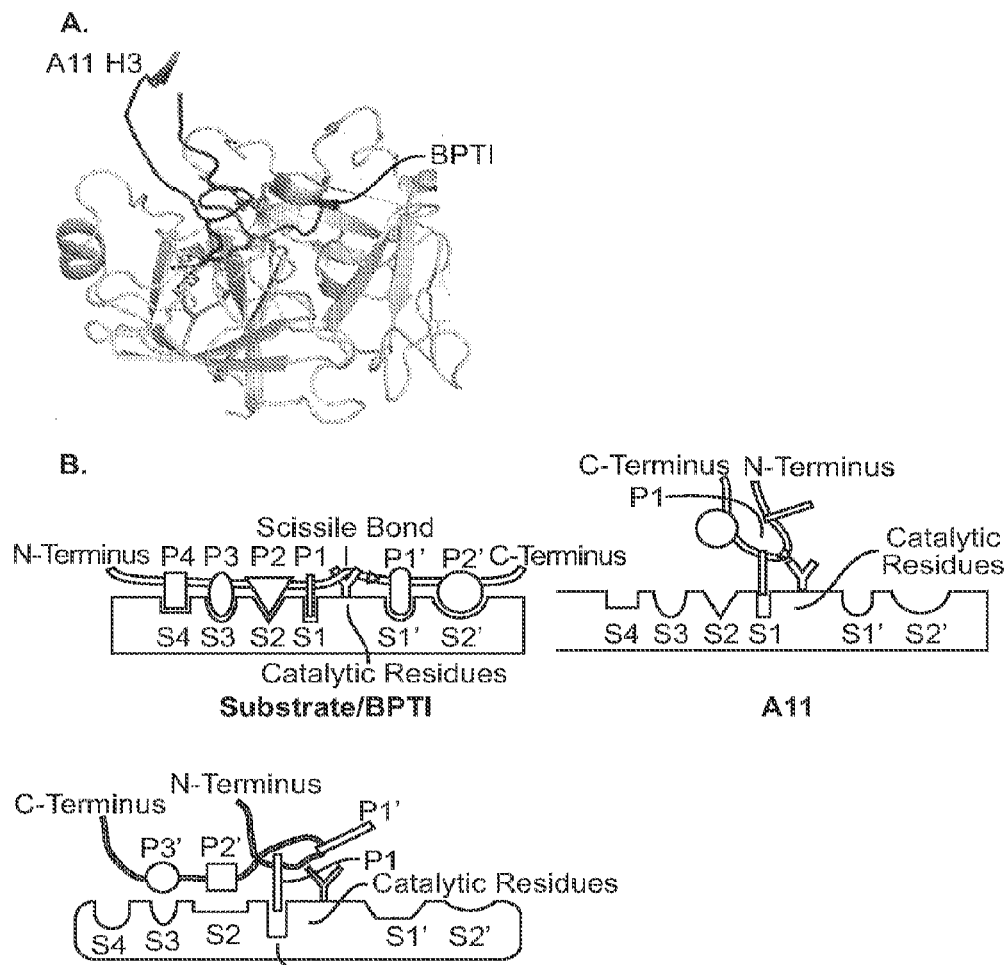
FIG. 6 shows the insertion of A11 H3 loop into the MT-SP1 active site. Panel A shows that the H3 hypervairable loop of A11 inserts an arginine (ArgH100b) into the active site of MT-SP1. Panel B compares the binding of A11 to MT-SP1 (right) with the binding of the bovine pancreatic trypsin inhibitor (BPTI) on the left. Binding of the E2 antibody to MT-SP1 is also shown below in Panel B.

The H3 loop of A11 (dark ribbon in FIG. 5, panel A) adopted a unique conformation in the protease active site (FIG. 6). It formed a β-hairpin turn that reaches into the protease active site while inserting an arginine residue (ArgH100b) into the active site of MT-SP1, but made few other contacts with the protease. AlaH99, AlaH100, and ValH100d combined to bury 174 Å$^2$ of surface area in hydrophobic interactions with the protease as the beta-hairpin strand extended into the active site. At the apex of the turn, A11 has two arginines. The C-terminal arginine was bound in the S1 specificity pocket, while the first (N-terminal) arginine extended towards the prime side of the protease active site. This conformation resulted in the putative scissile bond binding in a reverse orientation in the active site, rendering the protease incapable of cleavage at this position. Comparison with the BPTI demonstrates that A11 H3 loop is presented in the opposite direction to standard binding substrates, as highlighted by the model in FIG. 6, panel B. The H3 loop is 4.0 Å away from Asp189 at the bottom of the S1 pocket. This distance forces ArgH100b to make a 2.8 Å water-mediated hydrogen bond with Asp189 of MT-SP1. This conformation is different from the preferred salt bridge with Asp189 formed by P1 arginine substrates and mimics, but similar to the binding of a shorter P1 Lys. As shown in Example 6, ArgH100bLys mutation was deleterious to A11 binding to MT-SP1. This is because lysine side chain is one carbon shorter than an arginine side chain, and thus cannot make a similar water mediated hydrogen bond to the Asp residue at the bottom of the S1 pocket.

Example 10

Antibodies Specific for the Active Form of MT-SP1

Figure 7:
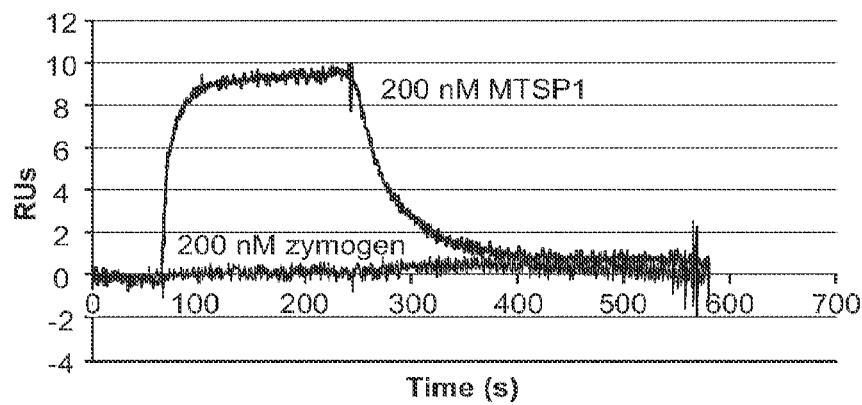
FIG. 7 depicts the result of a surface plasmon resonance experiment. Binding curves of A11 Fab to MT-SP1 is black and the binding curve of A11 Fab to the inactive mutant zymogen R15A is gray.

In order to evaluate MT-SP1 activity as a biomarker, probes were developed which exclusively targeted the active form of the enzyme. The probes are referred herein as E2 and A11. E2 and A11 are also the antibody inhibitors of MT-SP1 disclosed herein. E2 Fab was shown to be selective of the active form of the enzyme based on data from surface plasmon resonance (Farady C J et al. *J Mol Biol* 2008, 380: 351-60). A11 Fab was also found to selectively bind to the active form of MT-SP1 (FIG. 7). While binding of the catalytically active MT-SP1 can be clearly seen at 200 nM, no binding was observed for the inactive zymogen at concentrations up to 1 μM. That antibody binding is reliant on the activation-dependent stabilization of the active site is consistent with structural data (Farady C J et al. *J Mol Biol* 2008, 380: 351-60). Because they share similar mechanisms of inhibition and potencies against MT-SP1, we use both E2 and A11 interchangeably in these examples below.

Example 11

Inhibition of MT-SP1 in Cell Culture

Figure 8:
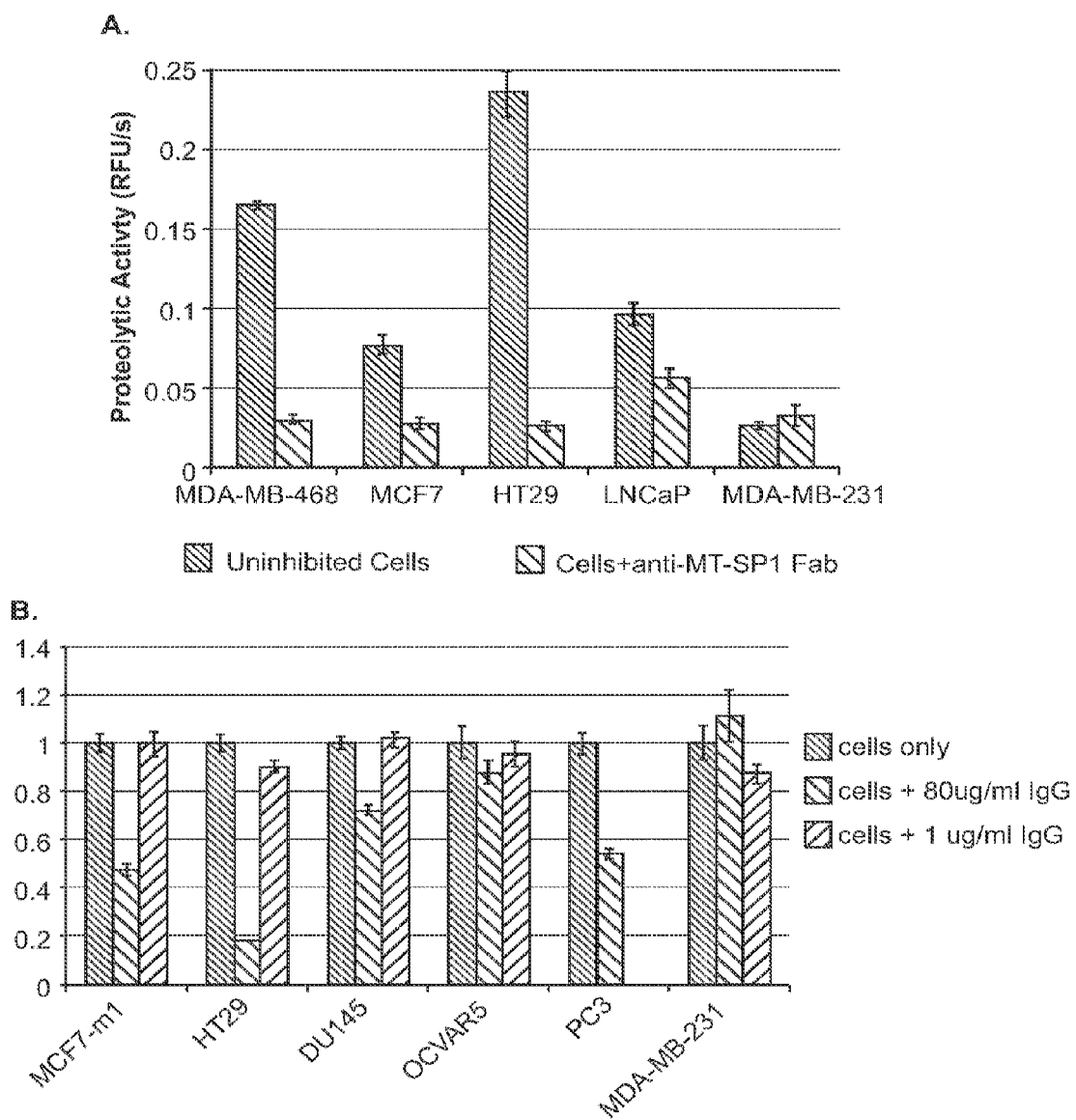
FIG. 8, panel A shows the inhibition of E2 on MT-SP1 activity in various cell lines. Panel B shows the inhibition of A11 on MT-SP1 activity in various cell lines.

The in vivo utility of inhibitor antibodies against MT-SP1MT-SP1 was explored in this and the following examples. MT-SP1 is a mosaic protein with several domains N-terminal to the protease domain that regulate protein-protein interactions. In this example, the ability of antibodies to bind to and inhibit full-length MT-SP1 was investigated. To look for inhibition of native MT-SP1 in a number of human cancer cell lines, an assay was created to measure proteolysis with and without E2 antibody inhibitors. To monitor cell-associated proteolysis, a substrate that fluoresces upon cleavage by any $P_1$-arginine specific protease named Spectrofluor tPA was added to human cancer cells in 96-well plates. Proteolysis was measured over time in a fluorescent plate reader. A decrease in the rate of proteolysis upon preincubation with MT-SP1-specific inhibitory antibodies confirms that not only was MT-SP1 active on these cells, but the antibodies were capable of inhibiting the native form of the protease. FIG. 8, panel A shows the results of this assay as performed with five different human cancer cells. Black bars represent total $P_1$-arginine proteolytic activity of uninhibited cells, while the gray bars represent the activity after cells have been incubated with E2 Fabs. All lines, with the exception of the breast cancer cell line MDA-MB-231, express measurable amounts of MT-SP1 mRNA (Bhatt A S et al. *Biol Chem* 2003, 384: 257-266). The MT-SP1-positive cells showed a decrease in proteolysis upon the addition of MT-SP1-specific antibody-based inhibitors, while the MT-SP1-negative line MDA-MB-231 showed no significant decrease in activity. Additionally, the cells showed complete or near complete inhibition of proteolysis in the presence of a broad spectrum inhibitor cocktail. The colon cancer cell line HT29, which expresses the most MT-SP1 mRNA of all of the cell lines examined, also showed the largest change in activity specific to the enzyme.

The experiment was repeated with A11 IgG antibody in 5 different cells line: MCF7 (breast cancer), HT29 (colon cancer), DU145 (prostate cancer), OVCAR5 (ovarian cancer) and PC3 (prostate). The results are shown in FIG. 8, panel B. In terms of percentage of P1-Arg proteolytic activity that can be inhibited, HT29 and MCF7-ml showed the largest difference. For raw numbers, PC3 shows the greatest quantitative change in activity (though there remains a significant amount of P1-Arg proteolysis even when MTSP1 was inhibited). MCF7-m1 and HT29 were later picked to be potential targets for further study in the later examples.

The results of these assays demonstrated that MT-SP1 is active on the surface of these cancer cells and that the inhibitor antibodies were able to bind to and inhibit the full-length protease.

Example 12

Ex Vivo Labeling of MT-SP1

Figure 9:
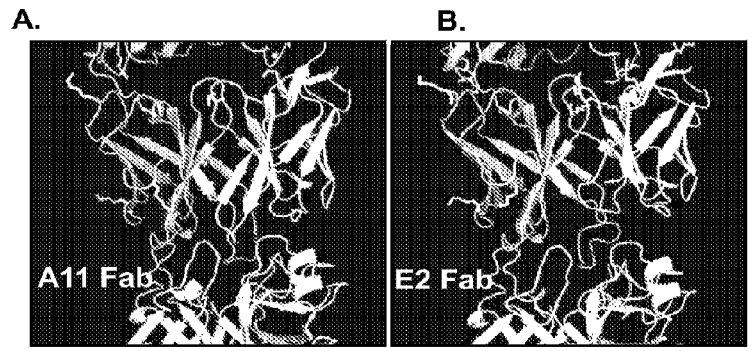
FIG. 9 shows A11 (panel A) and E2 (panel B) Fabs bound to the recombinant catalytic domain of MT-SP1.
Figure 10:
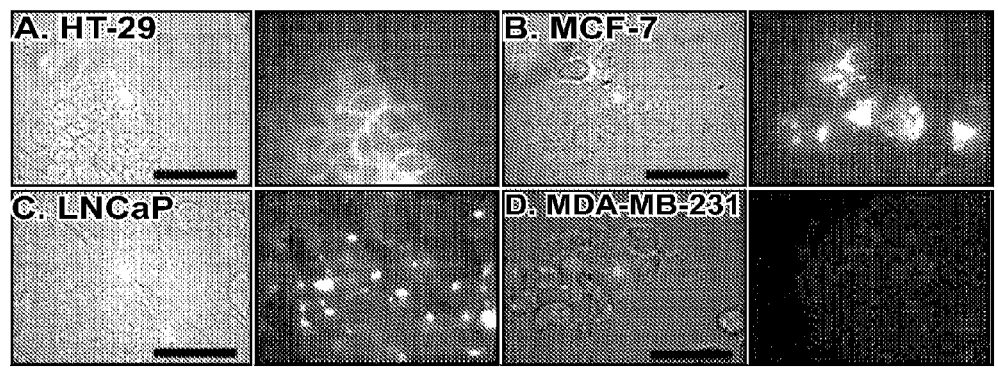
FIG. 10 shows the fluorescent micrographs of E2 scFv incubated with MT-SP1-positive cells and a negative control cell in culture. HT29 (panel A), MCF7 (panel B), and LNCaP (panel C). MDA-MD-231 express little to no MT-SP1 (panel D).

For the purposes of molecular imaging of MT-SP1 activity, the antibody probes were labeled while maintaining the probe-enzyme interaction. For fluorescent detection, commercially available dye-succinimidyl ester conjugates were used to nonspecifically label the antibody inhibitors via accessible lysines. Based on structural data of both A11 and E2 Fabs bound to recombinant MT-SP1, the labeling of free lysines (yellow) should not greatly interfere with enzyme binding (FIG. 9). Heavy chains of antibody are labeled magenta and light chains cyan in FIG. 9. Lysine residues are equite distal from the binding interface and labeling of the protein via non-specific succinimidyl ester conjugation to these sides chains resulted in small decreases in inhibition. Depending on the construct—scFv, diabody, Fab or IgG—an average of 1-6 dye molecules were conjugated per protein. Inhibition assays using conjugated antibody probes showed minor (0-5 fold) increases in $IC_{50}$ values, and given the high potency of these inhibitors, such a decrease was not a barrier to probe binding. To test the functionality of the scFv against full length protein, human cancer cells were incubated with labeled inhibitor antibody E2 and fluorescently imaged to look for probe association with the membranes of these cells. The results of these experiments are shown in FIG. 10. Three MT-SP1-positive cell lines—HT29, MCF7, and LNCaP—were visibly labeled with the fluorescent probes, while the negative control line MDA-MB-231 was not. The labeling also had the following difference: the HT29 signal appeared to be distributed evenly on the membrane of the cell while the signal on PC3 and MCF7 cells was more punctate. These results showed that the inhibitors (e.g. E2) were successful in selectively targeting MT-SP1-positive cells.

Figure 11:
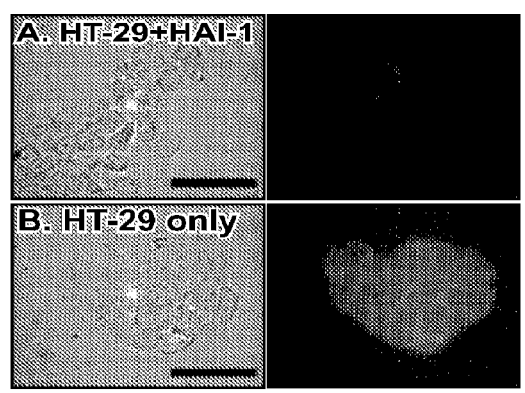
FIG. 11 shows the fluorescent micrographs of E2 scFv incubated with HT29 cells incubated with recombinant hepatocyte growth factor activator inhibitor-1 (HAI-1) (panel A) or HT29 cells alone (panel B).

MT-SP1 is putatively present on the surface of epithelial cells in at least three different isoforms—the inactive zymogen, active protease, and HAI-1-inactivated protease. To confirm whether the antibodies are binding to only active proteases and if the antibodies are capable of displacing HAI-1, the immunofluorescent cell labeling was carried out after HT29 cells were pre-incubated with recombinant HAI-1 (FIG. 11). Cells which were incubated with HAI-1 before the addition of fluorescently labeled E2 scFv showed much lower labeling than those which were not. The result of this experiment demonstrated that the antibodies do not displace HAI-1 bound to active protease, indicating that the signal from the bound antibodies derived from free active MT-SP1.

Example 13

Targeting MT-SP1 In Vivo

Figure 12:
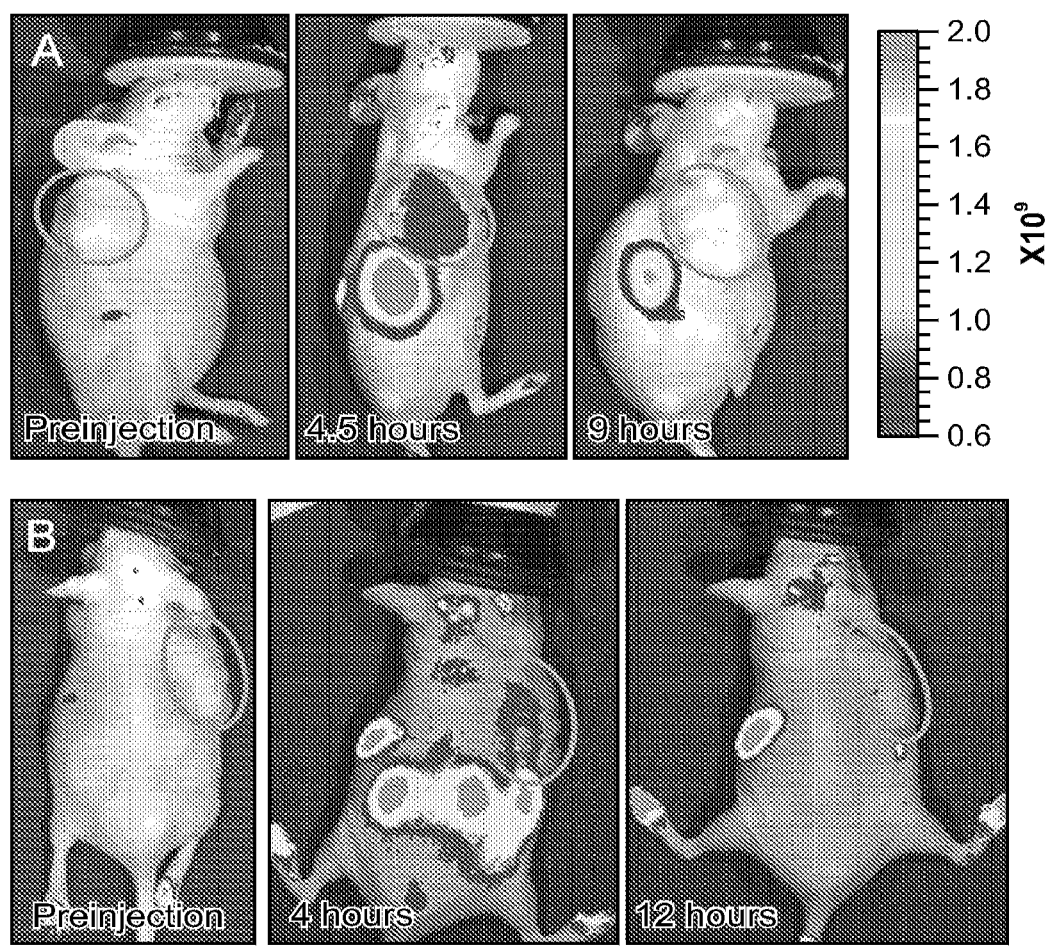
FIG. 12 shows E2 diabody (panel A) and E2 Fab (panel B) inhibitors in MCF7 xenograph mice with tumor cells circled. Black stains indicate boundaries around the presence of luciferase or alexa flour.
Figure 13:
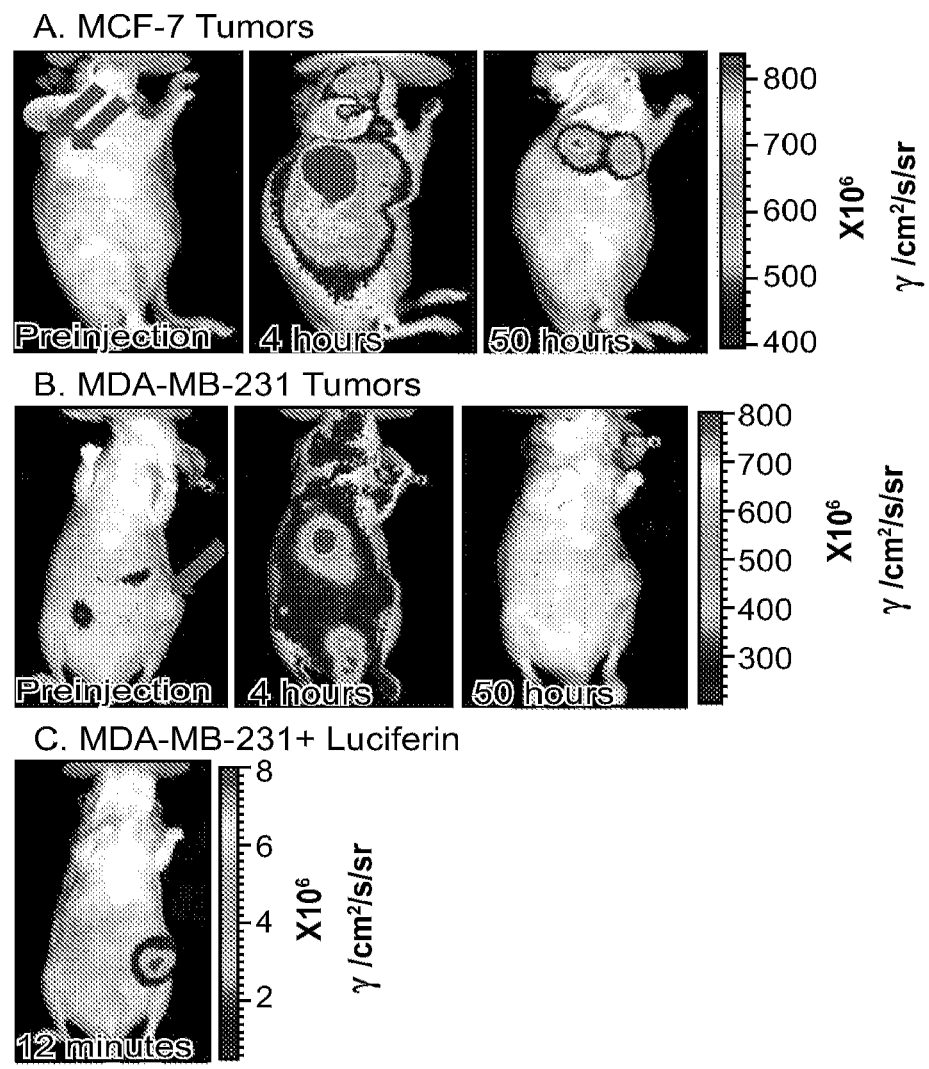
FIG. 13 shows that A11 IgG antibodies selectively target MT-SP1 positive tumors in vivo. Panel A shows a MCF7 xenograph mouse with tumor indicated by double arrows. Panel B shows a MDA-MB-231 (MT-SP1-negative) xenograph mouse as a negative control. Panel C shows the signal of active luciferase expressed by MDA-MB-231 cells after luciferin was injected. Black stains indicate boundaries around the presence of luciferase or alexa flour.

The probes were evaluated in vivo in this example. Using cell lines validated in the cell culture experiments in Example 11, xenograft mouse models were generated using MCF7 and MDA-MB-231-luc breast cancer cell lines. MDA-MB-231-luc cells are MDA-MB-231 cells which were modified to stably express luciferase, so that the tumor can also be imaged via bioluminescent detection of injected luciferin. These mouse models were injected with fluorescently labeled E2 diabody, E2 Fab or A11 IgG, and imaged for up to 50 hours to assess biodistribution of antibodies and any tumor localization. A11 IgG was labeled with AlexaFlour 680 and the mouse was imaged using a 2-D fluorescent imager. The α-MT-SP1 E2 diabody and E2 Fab showed tumor localization in MCF7 xenograft mice, but failed to achieve high tumor/background contrast due to high levels of signal retained in the excretory system (FIG. 12) Tumors are indicated by arrows. The A11 IgG, however, localized to the tumor and remained so until free protein was cleared, achieving excellent tumor to background contrast by 50 hours (FIG. 13, panel A). Similar injections in to MDA-MB-231 tumor-bearing mice showed no tumor associated signal over the same time period (FIG. 13, panel B). Approximately 2 mg of luciferin injected into these mice generated a tumor-specific signal (FIG. 13, panel C), validating both the presence of the MDA-MB-231 cells at this location and sufficient vasculature to deliver probe to the tumor. These results indicated that MT-SP1 were active in the tumors which were positive for MT-SP1 expression, and that this activity can be targeted in vivo for non-invasive imaging of cancer using these antibody-based inhibitors.

Figure 14:
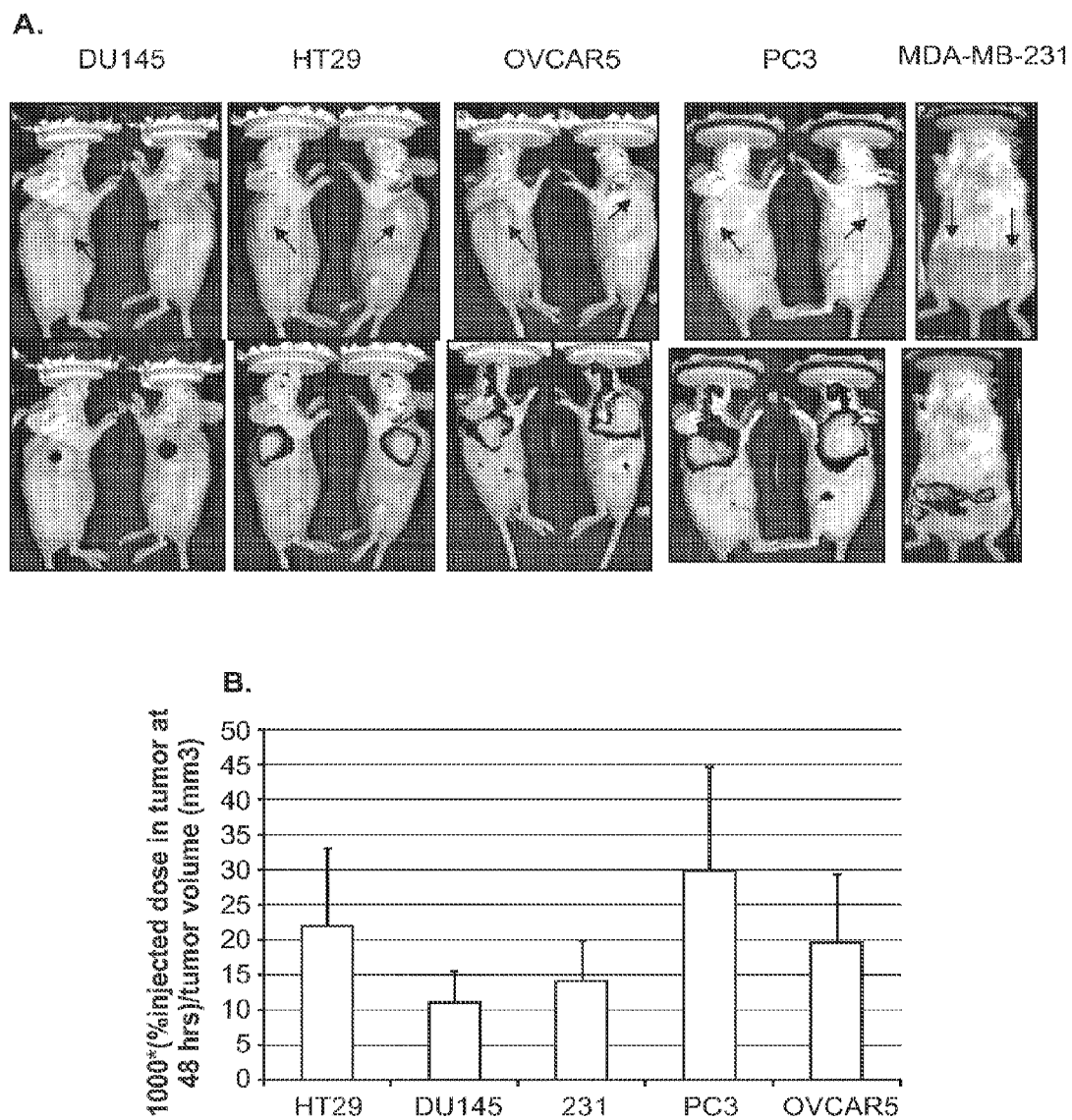
FIG. 14, panel A shows that A11 IgG antibodies selectively target MT-SP1 positive tumors in vivo. The first row shows xenograph mice with tumors (arrows) derived from various cell lines. Second row shows the signal of active luciferase, presence of which is indicated by surrounding black stains, after luciferin was injected. Panel B compares the tumor signal using percentages of injected dose in tumor at 48 hours divided by tumor volume (mm$^3$).

The same experiment was repeated with additional xenographs shown in FIG. 14, in which the models are generated using cell lines derived from DU145, HT29, OVCAR5, PC3, and MDA-MB-231. Various mouse xenografts were imaged with AlexaFluor 680 labeled A11 on a Xenogen IVIS-50 bioluminescence/fluorescence optical imager. In panel A of FIG. 14, the arrows point to location of tumors in the mice in the first row. The concentric black circles in the second row are the signals indicating the localization of the A11 antibody. To compare tumor signals the percentage of initial dose that remains in the tumor at 48 hours were measured and then divided by the volume of the tumor. Data from multiple tumors in multiple mice are collected and shown in Panel B. Signals were the most robust in xenograph models containing tumor cells from HT29 and PC3 tumor is slow growing while HT29 was the cell line that showed a large inhibition of MT-SP1 in cell culture by A11 antibody.

Example 14

Study of Anti-Tumor Efficacy Activity In Vivo

The first step in the efficacy trial of A11 in vivo was to determine the appropriate mouse xenograft model to be used. Since MT-SP1 was implicated in a myriad of cancers of epithelial origin, a diverse array of cell lines were surveyed in the examples above in order to find cell lines that are suitable for MT-SP1 targeting. Out of the candidate cell lines, PC3 and HT29 displayed the good localization of fluorescence signal in the area of the tumors so PC3 and HT29 were selected for the in vivo efficacy study in this Example.

Five nude/SCID mice were implanted per cell line with two tumors per mouse. When the tumors were around 300 mm³ in size, each mouse was injected with 2 nmoles of AlexaFluor labeled A11 and imaged with out to 48 hr.

To evaluate the anti-tumor efficacy of A11 in PC3 and HT29, a four arm study approach was used for each cell line. In each xenograft study the four arms consisted of one arm dosed with A11, another with a control antibody (Palivizumab), a third with a standard of care therapeutic (Docetaxel or Cisplatin) and the fourth arm a vehicle control. Each arm enrolled ten mice for a total of forty mice per xenograft study. The mice were weighed and their tumor volumes were measured twice a week for three weeks. At the end of the study, the tumors and lungs of five mice per group were collected and fixed for further analysis.

For the PC3 study the dosing regimen was Group 1: vehicle (PBS buffer 100 µl, iv, q7d×3), Group 2: Palivizumab (30 mg/kg, iv, q7d×3) Group 3: A11 (30 mg/kg, iv, q3d×3), and Group 4: Docetaxel (4 mg/kg, iv, q7d×3). The results from the PC3 study (FIG. 15, panel A) showed a miniscule therapeutic effect in the A11 treated arm compared to vehicle. The control antibody, Palivizumab, was slightly more efficacious than A11, but it was not statistically significant. As expected, the arm treated with Docetaxel showed the highest lack of tumor growth and the most significant loss in body weight.

Figure 15:
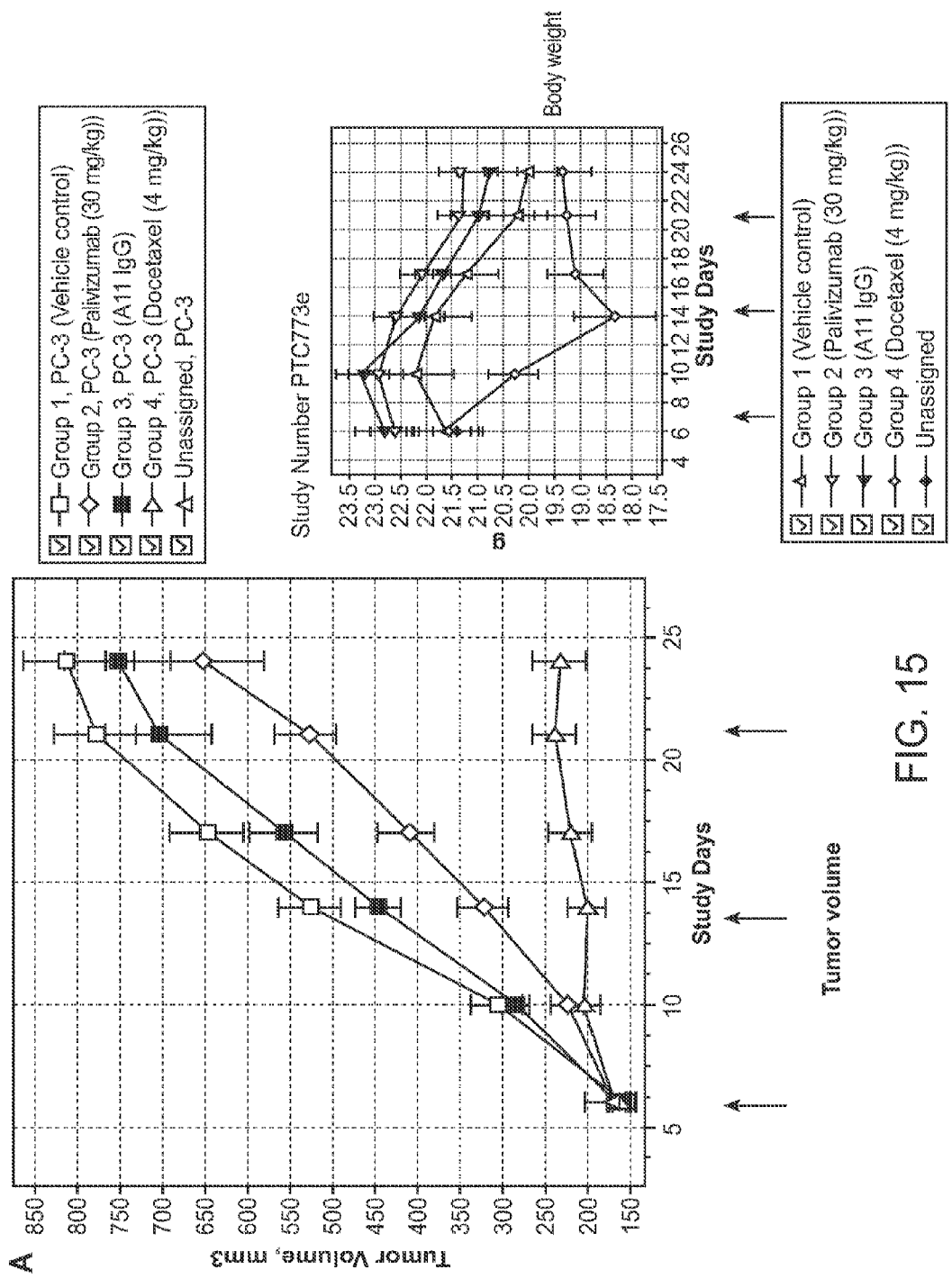
FIG. 15, panel A shows the tumor volume over time for various groups of mice having PC-3 tumor xenographs. The body weights of the mice are shown as a small inset. Panel B shows the tumor volume over time for various groups of mice having H29 tumor xenographs. The body weights of the mice are shown as a small inset. Panel C shows a pilot study using a smaller group of mice than the experiment shown in Panel B.

The regimen for HT29 was Group 1: vehicle (PBS buffer 100 µl, iv, q7d×3), Group 2: Palivizumab (30 mg/kg, iv, q7d×3), Group 3: A11 (30 mg/kg, iv, q3d×3), and Group 4: Cisplatin (4 mg/kg, iv, q7d×3). In the HT29 study (FIG. 15, panel B), the results were similar in that A11 did not show significant therapeutic benefit and the growth curve for that arm was similar to the curve for the control antibody. The results of a pilot study of only 5 mice per group for H29 are shown in FIG. 15, panel C.

Example 15

Labeling A11 with 1,4,7,10-tetraazacyclododecane-1,4,7,10-tetraacetic acid (DOTA)

In order to use the A11 IgG for nuclear imaging, the macrocyclic transition metal-chelate group DOTA had to be introduced to the structure of the antibody. This was accomplished by modifying exposed lysine side chain groups on the surface of the IgG with an activated ester form of DOTA. Briefly, a 35 µM aliquot of A11 IgG, in a conjugation buffer of 0.1M $NaHCO_3$, 1M NaCl, pH 8.3, was reacted with a twenty-five fold molar excess of DOTA-NHS ester. The DOTA-NHS ester (Macrocyclics) in DMSO, was added to the A11 IgG aliquot and incubated at room temperature on a shaker in the dark for 90 minutes. The final total volume for the reaction was 500 µl. On completion, the sample was diluted with 2 ml of 1×PBS and the excess unreacted DOTA-NHS ester was removed by size-exclusion chromatography. Concentrating the sample down to 500 µl with a 50 kDa spin filter yielded an A11 IgG sample of 29 µM. According to similar labeling protocol from Invitrogen, it is estimated that four lysines per IgG will be labeled with DOTA molecules. The labeled IgG was stored at 4° C. until further use.

Example 16

Radiolabeling DOTA-A11 IgG with $^{111}$In and In Vivo SPECT/CT Imaging

Figure 16:
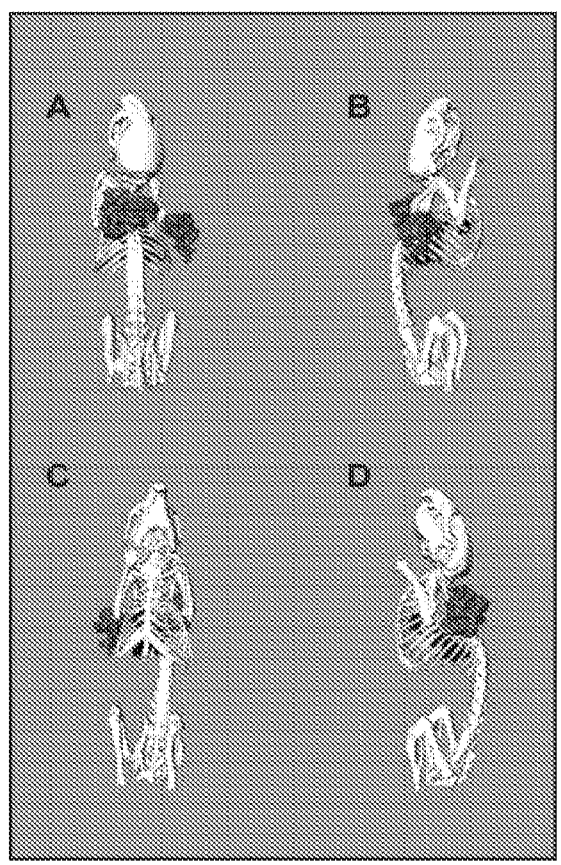
FIG. 16 is an Amira processed representation of an HT29 xenograft mouse imaged with $^{111}$In-DOTA-A11 at 48 hr post-injection. Injected dose: 15 µg IgG, 250 µCi. The CT skeletal image can be seen in white. For SPECT, dark gray represents the bilateral HT29 tumors and non-specific uptake can be seen in the chest cavity in black. A) coronal view at 0°; B) sagittal view at 90°; C) coronal view at 180°; D) sagittal view at 270°.
Figure 17:
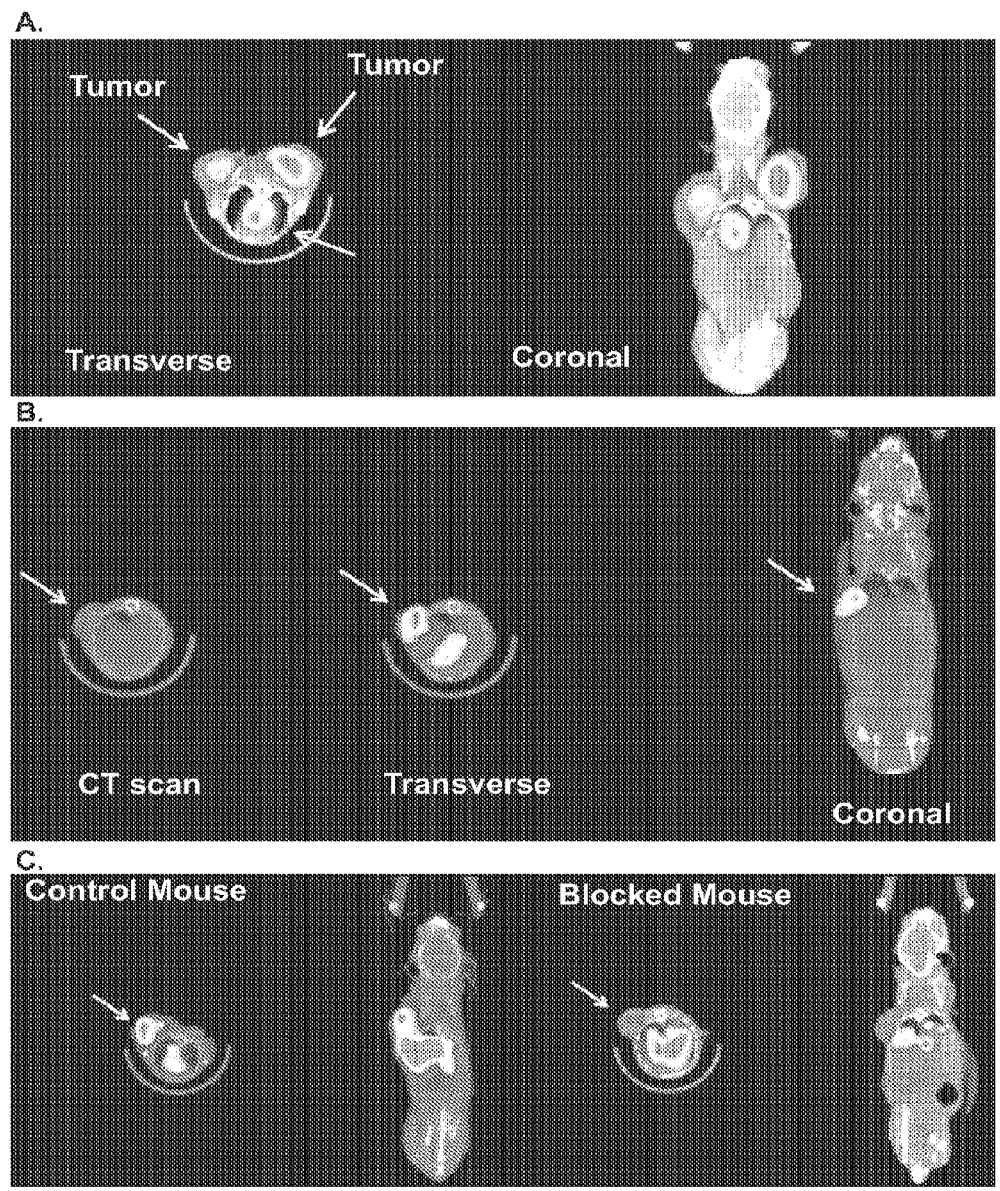
FIG. 17, panel A is an $^{111}$In-DOTA-A11 SPECT/CT image of a HT29 bilateral xenograph at 48 hour post injection. Signals are represented by regions with gray topographic boundaries. Injection was done with 15 µg of A11 IgG (250 µCi). Panel B is an $^{111}$In-DOTA-Palivizumab SPECT/CT image of a PC3 xenograph at 48 hour post injection. Panel C is an $^{111}$In-DOTA-A11 SPECT/CT image of a HT29 bilateral xenograph without (left) or with Ecotin blocking (right) at 48 hour post injection. Panel D is $^{111}$In-DOTA-A11 SPECT/CT image of a MT-SP1 negative MDA-MB-231 xenograph.
Figure 17:
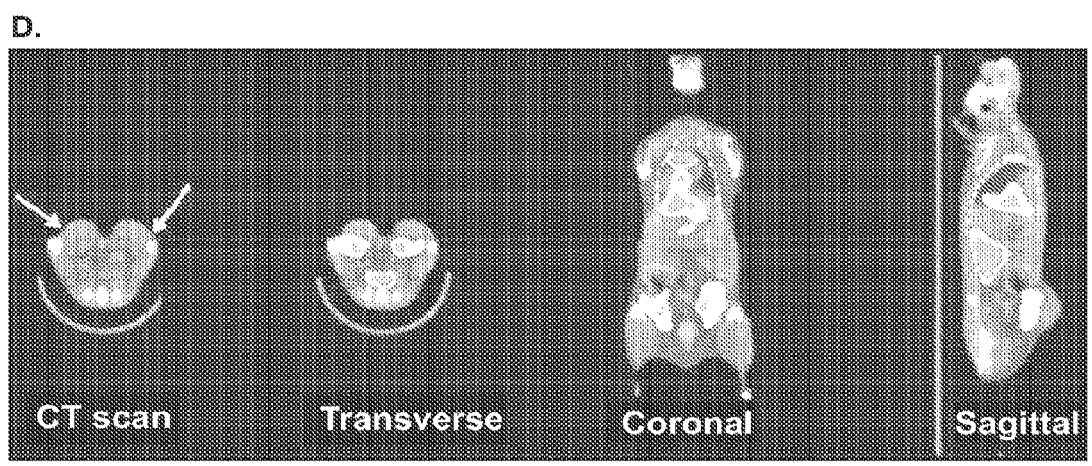

For radiolabeling, the DOTA-A11 IgG was diluted to 2 µM with 1×PBS. This corresponds to a weight by volume concentration of around 250 µg/ml. A 200 µl DOTA-A11 IgG aliqout (50 µg of IgG) was incubated with 12 µl of $^{111}InCl_3$ (2.59 mCi) in 0.01N HCl for 50 minutes at 37° C. Using radio TLC, the labeling efficiency of the $^{111}$In with the DOTA chelate was determined to be 90%. The radiolabeled antibody was separated from unreacted by size-exclusion chromatography using a PD-10 column pre-equilibrated with 1×PBS buffer. 0.5 ml fractions were collected from the column and were assayed for the presence of radiolabeled IgG by radio TLC. Fractions with high radioactive purity were then injected into the tail vein of six-week old nude mice bearing HT29 human colon cancer xenografts of approximately 400 mm³ in size. Normally for each injection, around 10 µg of IgG is administered corresponding to an $^{111}$In activity of 200 µCi to 450 µCi. The mice were then imaged serially at 24 hr, 48 hr and 72 hr using a Gamma Medica Ideas X-SPECT SPECT/CT scanner. The CT was acquired using S12 slices per scan at 75 keV. The SPECT imaging consisted of 64×64 matrix images at 120 stops (images obtained at 3° intervals), 30 seconds per stop with a region of interest of 4.5 cm. A pinhole collimator (0.5 mm) was used to provide high resolution SPECT images. CT and SPECT images were reconstructed and fused together using the software provided by the manufacturer. The data were then analyzed using Visage Imaging Amira software. A processed image of the HT29 xenograph labeled with $^{111}$In-DOTA-A11 is shown in FIG. 16 with four different views. As indicated by regions that are dark gray, A11 specifically labeled HT29 tumors while the non-specific uptake was seen in the chest cavity shown in black. Transverse and coronal images of the HT29 bilateral xenograph are also shown in FIG. 17, panel A. Injection was done with 15 µg of A11 IgG (250 µCi).

The experiments were repeated for Palivizumab in PC3 tumor xenographs and for other controls. As shown in FIG. 17, panel B, $^{111}$In-DOTA-Palivizumab was found to localize to tumors in a PC3 xenograph at 48 hour post injection.

Ecotin is a serine protease inhibitor known to block binding of A11 to MT-SP1. Ecotin was then used in the experiment shown in FIG. 17, panel C to test for the specificity of A11's localization to tumors. Control mouse on the left received 15 µg of $^{111}$In-DOTA-A11 (201 µCi) while the mouse blocked with ecotin was dosed with 200 µg of ecotin 24 hour i.p. prior to injection of 18 µg of $^{111}$In-DOTA-A11 (220 µCi). As seen in the figure, the blocked mouse failed to show localization of $^{111}$In-DOTA-A11 signal at the tumor site while the control has the expected localization of A11 at the tumor site.

Lastly, in a mouse that is negative for MT-SP1, there was also no localization of A11 signals, further demonstrating the specificity of A11 for HT29 tumors. FIG. 17, Panel D shows several views of the MT-SP1 negative MDA-MB-231 xenograph mouse.

Example 17

Screening for Specific Antibody Inhibitor of Candidate Protease

Phage display libraries may be used to screen candidate protein-binding agents that could act as inhibitors for a specific protease of interest.

The protease of interest is immobilized on an ELISA plate or on beads through a number of possible interactions including hydrophobic adsorption, biotin-avidin interaction and $Ni^{2+}$-6×His interaction. The phage library is the incubated with the immobilized antigen/protease, washed, and recovered. The recovered phage is amplified in *E. coli* and used in successive selection rounds. The stringency of the washes increases with subsequent selections (e.g. three total selection rounds). Selection techniques include increased wash times, increased detergent concentrations, increased salt concentrations, and inclusion of known macromolecular inhibitors, such as BPTI, Ecotin, and/or previously identified antibody inhibitors. Various assays described above, such as binding and inhibition assays, are used to identify inhibitory antibodies.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A protease-binding antibody, comprising:
   a) a VLCDR1 comprising the amino acid sequence of SEQ ID NO: 16;
   b) a VLCDR2 comprising the amino acid sequence of SEQ ID NO: 17;
   c) a VLCDR3 comprising the amino acid sequence of SEQ ID NO: 18;
   d) a VHCDR1 comprising the amino acid sequence of SEQ ID NO: 19;
   e) a VHCDR2 comprising the amino acid sequence of SEQ ID NO: 20; and
   f) a VHCDR3 comprising the amino acid sequence of SEQ ID NO: 10.

2. The protease-binding antibody of claim 1, wherein said antibody comprises:
   a) a light chain of at least 90% amino acid sequence identity to SEQ ID NO: 1; and
   b) a heavy chain of at least 85% amino acid sequence identity to SEQ ID NO: 3.

3. The protease-binding antibody of claim 1, wherein said protease is P1-Arg-specific protease.

4. The protease-binding antibody of claim 3, wherein said P1-Arg- specific protease is a type II transmembrane serine protease.

5. The protease-binding antibody of claim 4, wherein said type II transmembrane serine protease is membrane-type serine protease I.

6. The protease-binding antibody of claim 1, wherein said protease-binding antibody is detectably labeled.

7. The protease-binding antibody of claim 1, wherein said antibody is radiolabeled.

8. A pharmaceutical composition comprising the protease-binding antibody of claim 1 and a pharmaceutical acceptable excipient.

9. The pharmaceutical composition of claim 8, wherein said composition further comprises an anti-cancer agent.

10. A method of detecting a cancer cell comprising a cell surface serine protease in a subject comprising:
    contacting the protease-binding antibody of claim 1 with a cell of said subject suspected of being cancerous;
    detecting said protease-binding antibody bound to said cell.

11. The method of claim 10, wherein said detecting comprises imaging tissues of said subject.

12. The method of claim 10, wherein said protease-binding antibody is radiolabeled.

13. The method of claim 10, wherein said detecting comprises single photon emission computed tomography.

14. A method of inhibiting a serine protease comprising:
    contacting the protease-binding antibody of claim 1 to said protease.

15. A kit for detecting cancer cells in a subject comprising: the protease binding antibody of claim 1.

16. The kit of claim 15, wherein said protease binding antibody is radiolabeled.

* * * * *